(12) United States Patent
Zhu et al.

(10) Patent No.: US 10,208,290 B2
(45) Date of Patent: Feb. 19, 2019

(54) VIRION DISPLAY ARRAY FOR PROFILING FUNCTIONS AND INTERACTIONS OF HUMAN MEMBRANE PROTEINS

(71) Applicant: THE JOHNS HOPKINS UNIVERSITY, Baltimore, MD (US)

(72) Inventors: Heng Zhu, Towson, MD (US); Prashant Desai, Owings Mills, MD (US); Min Li, Lutherville-Timonium, MD (US); Shaohui Hu, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/900,314

(22) PCT Filed: Jun. 20, 2014

(86) PCT No.: PCT/US2014/043404
§ 371 (c)(1),
(2) Date: Dec. 21, 2015

(87) PCT Pub. No.: WO2014/205344
PCT Pub. Date: Dec. 24, 2014

(65) Prior Publication Data
US 2016/0355789 A1 Dec. 8, 2016

Related U.S. Application Data

(60) Provisional application No. 61/837,929, filed on Jun. 21, 2013.

(51) Int. Cl.
| | | |
|---|---|---|
| *C12N 7/00* | (2006.01) | |
| *G01N 33/543* | (2006.01) | |
| *G01N 33/566* | (2006.01) | |
| *G01N 33/58* | (2006.01) | |
| *C07K 1/04* | (2006.01) | |
| *G01N 33/68* | (2006.01) | |
| *A61B 17/34* | (2006.01) | |
| *A61B 18/02* | (2006.01) | |
| *G01N 33/74* | (2006.01) | |
| *A61B 18/00* | (2006.01) | |

(52) U.S. Cl.
CPC ............ *C12N 7/00* (2013.01); *A61B 17/3478* (2013.01); *A61B 18/02* (2013.01); *A61B 18/0218* (2013.01); *C07K 1/047* (2013.01); *G01N 33/566* (2013.01); *G01N 33/6854* (2013.01); *G01N 33/74* (2013.01); *A61B 2018/0038* (2013.01); *A61B 2018/0212* (2013.01); *A61B 2018/0275* (2013.01); *A61B 2217/005* (2013.01); *C07K 2319/03* (2013.01); *C07K 2319/735* (2013.01); *C12N 2710/16621* (2013.01); *C12N 2710/16645* (2013.01); *C12N 2810/855* (2013.01); *G01N 2333/70514* (2013.01); *G01N 2333/726* (2013.01)

(58) Field of Classification Search
None
See application file for complete search history.

(56) References Cited

U.S. PATENT DOCUMENTS

| | | |
|---|---|---|
| 5,082,767 A | 1/1992 | Hatfield et al. |
| 5,601,980 A | 2/1997 | Gordon et al. |
| 5,677,196 A | 10/1997 | Herron et al. |
| 5,731,152 A | 5/1998 | Maracas et al. |
| 5,807,522 A | 9/1998 | Brown et al. |
| 2003/0124572 A1 | 7/2003 | Umek et al. |
| 2005/0123563 A1 | 6/2005 | Doranz et al. |
| 2008/0274988 A1 | 11/2008 | Brandon et al. |

FOREIGN PATENT DOCUMENTS

| | | |
|---|---|---|
| WO | 84/03506 A1 | 9/1984 |
| WO | 84/03564 A1 | 9/1984 |
| WO | 96/26432 A1 | 8/1996 |

OTHER PUBLICATIONS

Dolter et al. Incorporation of CD4 into Virions by a Recombinant Herpes Simplex Virus. J. of Virol. 1993, 67:189-195.*
Kouvatsis et al. Characterization of herpes simplex virus type 1 recombinants that express and incorporate high levels of HCV E2-gC chimeric proteins. Virus Research 2007, 123:40-49.*
International Search Report and Written Opinion dated Jan. 2, 2015, from related PCT Patent Application No. PCT/US14/043404.
Woodruff et al., "Inhibiting the C5-C5a receptor axis," Molecular Immunology, Aug. 1, 2011 (Aug. 1, 2011) vol. 48, No. 14, p. 1631-1642.
Espina et al., "Protein microarrays: Molecular profiling technologies for clinical specimens," Proteomics, Nov. 1, 2003 (Nov. 1, 2003), vol. 3, No. 11, p. 2091-2100.
Hu et al., "VirD: A Virion Display Array for Profiling Functional Membrane Proteins," Analytical Chemistry, Aug. 13, 2013 (Aug. 13, 2013), vol. 85, p. 8046-8054.

(Continued)

*Primary Examiner* — Nianxiang Zou
(74) *Attorney, Agent, or Firm* — Casimir Jones, S.C.; Jeffrey W. Childers

(57) ABSTRACT

Provided herein are recombinant virion arrays comprising human membrane bound proteins that retain their native conformations and/or interactions, recombinant HSV-1 virions, and methods of use including high-content, high-throughput assays for screening for ligands and/or drugs that bind human membrane bound proteins, diagnostic assays, proteomic assays, and biosensor assays. Also provided are recombinant HSV-1 virions comprising an envelope comprising a plurality of heterologous membrane bound proteins that retain their native conformations and/or interactions as well as recombinant HSV-1 bacterial artificial chromosome (BAC) clones encoding heterologous membrane polypeptides.

25 Claims, 13 Drawing Sheets
Specification includes a Sequence Listing.

(56) References Cited

OTHER PUBLICATIONS

Fang, Y., Frutos, A. G. & Lahiri, J. Membrane protein microarrays. J Am Chem Soc 124, 2394-5 (2002).

Tang, C. S. et al. Dynamic, electronically switchable surfaces for membrane protein microarrays. Anal Chem 78, 711-7 (2006).

Dolter, K. E., King, S. R. & Holland, T. C. Incorporation of CD4 into virions by a recombinant herpes simplex virus. J Virol 67, 189-95 (1993).

Kouvatsis, V. et al. Characterization of herpes simplex virus type 1 recombinants that express and incorporate high levels of HCV E2-gC chimeric proteins. Virus Res 123, 40-9 (2007).

Cai, W. Z., Person, S., Warner, S. C., Zhou, J. H. & DeLuca, N. A. Linker-insertion nonsense and restriction-site deletion mutations of the gB glycoprotein gene of herpes simplex virus type 1. J Virol 61, 714-21 (1987).

Holland, T. C., Homa, F. L., Marlin, S. D., Levine, M. & Glorioso, J. Herpes simplex virus type 1 glycoprotein C-negative mutants exhibit multiple phenotypes, including secretion of truncated glycoproteins. J Virol 52, 566-74 (1984).

Homa, F. L., Purifoy, D. J., Glorioso, J. C. & Levine, M. Molecular basis of the glycoprotein C-negative phenotypes of herpes simplex virus type 1 mutants selected with a virus-neutralizing monoclonal antibody. J Virol 58, 281-9 (1986).

Carr, S. A. et al. Protein and carbohydrate structural analysis of a recombinant soluble CD4 receptor by mass spectrometry. J Biol Chem 264, 21286-95 (1989).

Cain, S. A. & Monk, P. N. The orphan receptor C5L2 has high affinity binding sites for complement fragments C5a and C5a des-Arg(74). J Biol Chem 277, 7165-9 (2002).

Tao, S. C. et al. Lectin microarrays identify cell-specific and functionally significant cell surface glycan markers. Glycobiology 18, 761-9 (2008).

Kung, L. A. et al. Global analysis of the glycoproteome in *Saccharomyces cerevisiae* reveals new roles for protein glycosylation in eukaryotes. Mol Syst Biol 5, 308 (2009).

Li, M. Applications of display technology in protein analysis. Nat Biotechnol 18, 1251-6 (2000).

Desai, P., DeLuca, N. A. & Person, S. Herpes simplex virus type 1 VP26 is not essential for replication in cell culture but influences production of infectious virus in the nervous system of infected mice. Virology 247, 115-24 (1998).

Hahn, W. C. et al. Creation of human tumour cells with defined genetic elements. Nature 400, 464-8 (1999).

Tengelsen, L. A., Pederson, N. E., Shaver, P. R., Wathen, M. W. & Homa, F. L Herpes simplex virus type 1 DNA cleavage and encapsidation require the product of the UL28 gene: isolation and characterization of two UL28 deletion mutants. J Virol 67, 3470-80 (1993).

Desai, P., Homa, F. L., Person, S. & Glorioso, J. C. A genetic selection method for the transfer of HSV-1 glycoprotein B mutations from plasmid to the viral genome: preliminary characterization of transdominance and entry kinetics of mutant viruses. Virology 204, 312-22 (1994).

Cai, W. Z., Person, S., DebRoy, C. & Gu, B. H. Functional regions and structural features of the gB glycoprotein of herpes simplex virus type 1. An analysis of linker insertion mutants. J Mol Biol 201, 575-88 (1988).

Gierasch, W. W. et al. Construction and characterization of bacterial artificial chromosomes containing HSV-1 strains 17 and KOS. J Virol Methods 135, 197-206 (2006).

Zhang, Y., Muyrers, J. P., Testa, G. & Stewart, A. F. DNA cloning by homologous recombination in *Escherichia coli*. Nat Biotechnol 18, 1314-7 (2000).

Angers et al. (2000) Proc. Natl. Acad. Sci. USA, 97:3684-3689.

Abbondanzo et al. (1993) Methods in Enzymology, Academic Press, New York. pp. 803-823.

Higgins and Sharp (1989) CABIOS. 5:151-151.

Altschul et al. (1990) J. Mol. Biol. 215:403-410.

Stadel et al. (1997) Trends in Pharmocological Review 18:430-437.

Hovis et al. (2000) Langmuir 16:894-897.

Geysen et al. (1984) Proc. Natl. Acad. Sci. U.S.A. 81:3998-4002.

\* cited by examiner

VIRION DISPLAY ARRAY FOR PROFILING FUNCTIONS AND INTERACTIONS OF HUMAN MEMBRANE PROTEINS

CROSS-REFERENCE

This application is a 35 U.S.C. § 371 National Stage Entry of International Application No. PCT/US14/043404 having an international filing date of Jun. 20, 2014, which claims the benefit of U.S. Provisional Application No. 61/837,929, filed on Jun. 21, 2013, which applications are incorporated herein by reference in their entirety.

FEDERALLY SPONSORED RESEARCH OR DEVELOPMENT

This invention was made with government support under grant no. GM076102, AI063182, and RR020839 awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00293_ST25.txt". The sequence listing is 4,676 bytes in size, and was created on Dec. 16, 2015. It is hereby incorporated by reference in its entirety.

BACKGROUND

Approximately one-third of the human proteome is comprised of membrane proteins that belong to protein families with a variety of biochemical activities, such as transporters, channels, receptors, recognition molecules, and adhesion molecules. Membrane proteins are critically important molecules for cell survival, maintenance of cell homeostasis, cell signaling, immune surveillance, molecular transport, and cell-cell communication. This class of proteins represents up to 70% of therapeutic targets for all prescribed drugs. Therefore, development of a high-throughput platform that enables profiling membrane proteins in an active conformation for their biochemical activities would have an important impact on drug discovery by streamlining small molecule screening methods. However, membrane proteins, especially those carrying multi-pass transmembrane (TM) domains, are notoriously difficult to study because they have to be embedded in a membrane to maintain a native conformation and many require proper posttranslational modifications (PTMs), such as glycosylation, which occurs during transport in the cellular secretory pathway. Although membrane protein microarrays have been reported previously, biochemical purification using detergents limits the throughput and subsequent manipulation. (Fang et al. (2002) *J. Am. Chem. Soc.* 124:2394-5; Tang et al. (2006) *Anal. Chem.* 78:711-7 (2006)).

There is also an important need in the biomedical community for a reliable technology that produces the highest possible quality, reproducible antibody reagents to membrane proteins. Ongoing improvement of this technology pipeline will directly benefit both the health research community and the larger biomedical community.

The use of antibodies to detect single and multipass membrane bound proteins can be used to identify new biomarkers and perform many assays. For example, antibodies are also widely used in diagnostic applications, such as for clinical medicine (e.g., ELISA and radioimmunoassay systems). Analysis of cells and tissues in pathology laboratories includes the use of antibodies on tissue sections and in flow cytometry analyses. Antibodies are also useful as therapeutics.

The production of antibodies can be costly and time-consuming, thus methods for the high throughput production of antibodies, in particular, highly specific antibodies to membrane proteins, that is more cost-effective and less time-consuming is desirable. The present disclosure meets these needs, and provides related advantages.

SUMMARY

In some aspects, the presently disclosed subject matter provides an array comprising a plurality of recombinant virion microspots stably associated with a surface of a substrate, wherein the recombinant virion microspots comprise a plurality of recombinant virions, wherein the recombinant virions comprise envelopes comprising a plurality of heterologous membrane bound proteins that retain their native conformations and/or interactions. In certain aspects, the recombinant virions are recombinant Herpes simplex virus (HSV) virions, for example, Herpes simplex virus 1 (HSV-1) virions. In other aspects, the plurality of heterologous membrane bound proteins are human membrane bound proteins, including classical type I membrane proteins with a single transmembrane domain (e.g. CD4) or multi-spanning, G-protein coupled receptor (GPCR) membrane proteins (e.g. GPR77). In other aspects, the membrane bound protein is selected from the group consisting of an ion channel, a receptor tyrosine kinase, a receptor serine/threonine kinase, a receptor guanylate cyclase, a growth factor receptor, and a hormone receptor.

In other aspects, the substrate of the array comprises a substance selected from the group consisting of a ceramic substance, a glass, a metal, a crystalline material, a plastic, a polymer or co-polymer, and combinations thereof. In further aspects, the substrate can be configured as a chip, a slide or a microplate. In still further aspects, the surface of the substrate can be coated, e.g., wherein the coating can be a material that enhances the affinity of the recombinant virion microspot or the membrane bound protein for the substrate. In some aspects the coating can be selected from the group consisting of nitrocellulose, a silane, thiol, disulfide, a polymer, and a derivatized monolayer or multilayer comprising covalently bonded linker moieties. In a particular aspect, the substrate of the array comprises a glass, wherein the substrate can be configured as a slide, and wherein the surface of the substrate can be coated with nitrocellulose.

In some aspects, the recombinant virions in at least one or each microspot of the array comprise only one type of heterologous membrane bound protein. In other aspects, the recombinant virion array comprises a plurality of different membrane bound proteins present at separate locations of the recombinant virion array. In further aspects, at least one or each of the microspots of the array comprises a different heterologous membrane bound protein. In still further aspects, the recombinant virions in at least one or each microspot of the array comprise recombinant virions comprising envelopes comprising two or more different heterologous membrane bound proteins, including wherein the two or more different heterologous membrane bound proteins comprise two different membrane bound proteins involved in a heterodimer pair. In other aspects, the envelope of one or more recombinant virions in one microspot of the recombinant virion array comprises membrane bound proteins that differ from one or more membrane bound proteins comprised by the envelopes of recombinant virions in one or more separate microspots of the recombinant virion array. In further aspects, the type of heterologous membrane bound proteins comprised by the recombinant virions in one microspot of the array differs from the heterologous membrane bound proteins comprised by the recombinant virions in one or more different microspots of the same array. In another aspect, at least one or each of the microspots of the array comprises a different variant of the same heterologous membrane bound protein. In still further aspects, the array comprises subarrays of microspots, wherein at least one or each microspot comprises a different membrane bound protein, and wherein the subarray can be repeated multiple times as part of the larger array. In other aspects the heterologous membrane bound protein of one microspot can be related to the heterologous membrane bound protein of at least one different microspot, for example, wherein the related heterologous membrane bound proteins are members of the same protein family and/or are functionally related. In some aspects, the membrane bound protein comprises two or more subunits. In some aspects, the recombinant virion can be produced from a host cell coinfected with one or more viruses expressing the two or more subunits. In some aspects, the recombinant virion displays the two or more subunit as a complex. In some aspects, the membrane bound protein can be an engineered membrane bound protein comprising a reversed topology such that a cytosolic domain of the engineered membrane bound protein can be displayed on the outside of the recombinant virion.

In some aspects, methods for producing arrays comprising a plurality of recombinant virion microspots stably associated with a surface of a substrate, an array is provided, the method comprising: (a) providing a substrate having a surface; (b) providing a solution comprising recombinant virions comprising a plurality of recombinant virions, wherein the recombinant virions comprise envelopes comprising a plurality of heterologous membrane bound proteins that retain their native conformations and/or interactions, for example, HSV virions, for example, HSV-1 virions; (c) immersing the tip of a pin into the solution; (d) removing the tip from the solution to provide a solution adhered to the tip; (e) contacting the solution with the surface to thereby transfer the solution from the tip to the surface; and (f) repeating the contacting step a plurality of times to provide recombinant virion microspots patterned in an array on the surface.

In other aspects, a method for detecting a binding event between a heterologous membrane bound protein and a target is provided, the method comprising contacting a sample comprising a solution comprising the target with a recombinant virion array, and detecting a binding event between at least one or more of the heterologous membrane bound protein and the target. The target may be labeled and the detection step may comprise detecting the presence of the label by optical detection methods. In another aspect, the array of microspots can be incubated with a cognate labeled target for a heterologous membrane bound protein in the recombinant virion microspots of the array and an unlabeled target, and the binding event between the unlabeled target and the heterologous membrane bound protein in the recombinant virion microspots can be determined by measuring a decrease in the signal of the label due to competition between the cognate labeled target and the unlabeled target. Where the target can be unlabeled, the binding event may be determined by a change in physical properties at the interface or by mass spectroscopy.

In some aspects, the methods for detecting a binding event between a heterologous membrane bound protein and a target with the recombinant virion arrays comprise screening for ligands and/or drugs when a potential ligand and/or drug candidate can be screened directly for its ability to bind or otherwise interact with the plurality of heterologous membrane bound proteins on the array. The plurality of potential ligand and/or drug candidates may be screened in parallel for their ability to bind or otherwise interact with one or more types of heterologous membrane bound proteins on the array. In other aspects, the methods for detecting a binding event comprise:

(a) Screening a plurality of proteins for their ability to bind a particular component of a target sample, comprising detecting, either directly or indirectly, for the presence or amount of the particular component retained at at least one or each microspot, optionally further comprising the additional step of characterizing the particular component retained on at least one microspot;

(b) Detecting a binding event comprises assaying for protein-protein binding interactions comprising delivering a sample comprising at least one protein to be assayed for binding to the recombinant virion array, and detecting, either directly, or indirectly, for the presence or amount of the protein from the sample that can be retained at at least one or each microspot;

(c) Assaying in parallel for the presence of a plurality of targets in a sample which can react with one or more of the heterologous membrane bound proteins on the recombinant virion array, comprising delivering the sample to the array and detecting the interaction of the target with the heterologous membrane bound proteins at at least one or each recombinant virion microspot;

(d) Assaying in parallel for the presence of a plurality of targets in a sample which can bind one or more of the heterologous membrane bound proteins on the recombinant virion array, comprising detecting, either directly or indirectly, for the presence or amount of target retained at at least one or each microspot;

(e) Diagnostic methods, wherein the plurality of targets being assayed are indicative of a disease condition or the presence of a pathogen in a subject, for example, wherein the sample delivered to the array comprises a biological sample; and/or (f) Detecting antibodies that specifically bind heterologous membrane bound proteins in the recombinant virion microspots of the array.

Within any of the methods listed above, delivery of samples comprising solutions comprising targets to be bound by the heterologous membrane bound proteins in the recombinant virion microspots of the array may be preceded, followed, and/or accompanied by delivery of a blocking solution.

In other aspects, a recombinant virion is provided, wherein the recombinant virion comprises an envelope comprising a plurality of heterologous membrane bound proteins that retain their native conformations and/or interactions, for example, wherein the recombinant virion can be a recombinant HSV virion, for example, wherein the HSV virion can be an HSV-1 virion. In other aspects, the plurality of heterologous membrane bound proteins are human membrane bound proteins, including classical type I membrane proteins with a single transmembrane domain (e.g. CD4) or multi-spanning, G-protein coupled receptor (GPCR) membrane proteins (e.g. GPR77). In other aspects, the membrane bound protein is selected from the group consisting of an ion channel, a receptor tyrosine kinase, a receptor serine/threonine kinase, a receptor guanylate cyclase, a growth factor receptor, and a hormone receptor.

In further aspects, a recombinant HSV-1 bacterial artificial chromosome (BAC) clone encoding a heterologous membrane polypeptide is provided. In a particular aspect, the heterologous membrane bound protein of the HSV-1 BAC clone can be a human membrane bound protein, including classical type I membrane proteins with a single transmembrane domain (e.g. CD4) or multi-spanning, G-protein coupled receptor (GPCR) membrane proteins (e.g. GPR77). In other aspects, the membrane bound protein is selected from the group consisting of an ion channel, a receptor tyrosine kinase, a receptor serine/threonine kinase, a receptor guanylate cyclase, a growth factor receptor, and a hormone receptor.

In some aspects, a library of antibodies comprising: a plurality of different antibodies, wherein at least 10% of the plurality are antibodies to membrane bound proteins is provided. In some aspects, at least 20%, 30%, 40%, 50%, 60%, 70%, 80%, 90%, 95%, 99% or 100% of the plurality are antibodies to membrane bound proteins. In some aspects, at least one or each antibody of the plurality of antibodies to membrane bound proteins can be a monospecific antibody. In some aspects, at least one or each antibody of the plurality of antibodies to membrane bound proteins has a binding affinity of at least $10^{-7}$M ($K_D$) for its target membrane bound protein. In some aspects, the binding affinity can be at least $10^{-8}$M, $10^{-9}$M, $10^{-10}$M, $10^{-11}$M, $10^{-12}$M, $10^{-13}$M, $10^{-14}$M, $10^{-15}$M, or $10^{-16}$M. In some aspects, at least one or each antibody of the plurality of antibodies to membrane bound proteins binds a native form of its target membrane bound protein.

In some aspects, the plurality of antibodies comprises at least 50 different antibodies. In some aspects, the plurality of antibodies comprises at least 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 1000 different antibodies.

In some aspects, the plurality of antibodies binds at least 0.5% of the human membrane bound proteome or human proteome. In some aspects, the plurality of antibodies binds at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human membrane bound proteome or human proteome. In some aspects, at least one or each antibody of the plurality of antibodies to membrane bound proteins has a binding affinity for its target that can be within at least 20% of the binding affinity of another antibody of the plurality of antibodies to membrane bound proteins. In some aspects, at least one or each antibody of the plurality of antibodies to membrane bound proteins has a binding affinity for its target that can be within at least 1, 2, 3, 4, 5, 6, 7, 8, 9, 10, 11, 12, 13, 14, 15, 16, 17, 18, or 19% of the binding affinity of another antibody of the plurality of antibodies to membrane bound proteins. In some aspects, at least one or each antibody of the plurality of antibodies to membrane bound proteins. In some aspects, at least one or each antibody of the plurality of antibodies to membrane bound proteins can be an immunoprecipitating antibody. In some aspects, at least one or each antibody of the plurality of antibodies to membrane bound proteins can be an IgG antibody.

In some aspects, an array is provided comprising: a library of antibodies described herein is provided, wherein at least one or each antibody can be immobilized on a substrate. In some aspects, the substrate can be planar. In some aspects, the substrate can be a particle. In some aspects, the substrate comprises a solid material. In some aspects, the substrate comprises a porous material. In some aspects, the immobilization can be reversible. In some aspects, the immobilization can be irreversible.

In some aspects, a method of producing a library as described herein comprising: a) immunizing an animal one or more virions containing one or more membrane bound proteins or antigens of membrane bound proteins; b) isolating antibody-generating cells from the animal; c) isolating one or more antibodies from the antibody-generating cells; d) screening the one or more antibodies of step c) with a human proteome array or human membrane bound proteome array; and e) selecting an antibody that is monospecific for a single target on the a human proteome array or human membrane bound proteome array for the library is provided. In some aspects, the method further comprises pre-screening the one or more antibodies from the antibody-generating cells prior to antibody isolation. In some aspects, the pre-screening is by performing immunocytochemistry. In some aspects, the pre-screening is by determining binding of antibodies from the antibody-generating cells with a mixture comprising one or more target antigens. In some aspects, the mixture comprises a crude lysate, cell, protein, peptide, nucleic acid, or combination thereof. In some aspects, the mixture comprises a biological sample. In some aspects, the mixture comprises a mixture of virions. In some aspects, the one or more virions comprise a plurality of membrane bound proteins. In some aspects, the one or more virions comprise a plurality of antigens of membrane bound proteins. In some aspects, the one or more virions comprise at least 100 different membrane bound proteins or antigens from membrane bound proteins. In some aspects, the one or more virions comprise at least 200, 300, 400, 500, 600, 700, 800, 900, 1,000, 2,000, 3,000, 4,000, 5,000, 5,500, 5,600, or more different membrane bound proteins or antigens from membrane bound proteins. In some aspects, the one or more virions comprise at least 0.5% of the human proteome or human membrane bound proteome. In some aspects, the one or more virions comprises at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human proteome or human membrane bound proteome. In some aspects, the antibody-generating cells are B-cells. In some aspects, comprising immobilizing the antibody to a substrate. In some aspects, the substrate can be planar. In some aspects, the substrate can be a particle. In some aspects, the substrate comprises a solid material. In some aspects, the substrate comprises a porous material. In some aspects, the immobilization can be reversible. In some aspects, the immobilization can be irreversible. In some aspects, the one or more virions comprise any of the recombinant virions described herein.

In some aspects, a method of identifying an antibody monospecific for a human membrane bound protein comprising: contacting a plurality of antibodies with a human membrane bound proteome array or human proteome array comprising targets comprising human membrane bound proteins; determining binding between the plurality of antibodies and the targets present on the human membrane bound proteome array or human proteome array; and identifying an antibody as monospecific when the antibody binds to a single target on the human membrane bound proteome array or human proteome array, wherein the targets present on the human membrane bound proteome array or human proteome array are comprised in an envelope of a virion is provided. In some aspects, the human proteome array comprises at least 0.5% of the human proteome or human membrane bound proteome. In some aspects, the human proteome array comprises at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human proteome or human membrane bound proteome.

In some aspects, a method of identifying an antibody for a target comprising: contacting a target comprised in an envelope of a virion with a library of antibodies described herein; determining binding between the target comprised in an envelope of a virion and the plurality of antibodies; and identifying an antibody for the target when the target comprised in an envelope of a virion binds to an antibody of the library is provided.

In some aspects, a method of identifying an antibody for a target comprising: contacting a target comprised in an envelope of a virion with an array described herein; determining binding between the target comprised in an envelope of a virion and a plurality of antibodies; and identifying an antibody for the target when the target comprised in an envelope of a virion binds to an antibody of the array is provided.

In some aspects, a method of identifying a target comprising: contacting a target comprised in an envelope of a virion with a library of antibodies described herein; determining binding between the target comprised in an envelope of a virion and the plurality of antibodies; and identifying the target when the target comprised in an envelope of a virion binds to an antibody of the library is provided.

In some aspects, a method of identifying a target comprising: contacting a target comprised in an envelope of a virion with an array described herein; determining binding between the target comprised in an envelope of a virion and the plurality of antibodies; and identifying the target when the target comprised in an envelope of a virion binds to an antibody of the array is provided.

In some aspects, a method of identifying a ligand for a target membrane bound protein comprising: contacting a target membrane bound protein comprised in an envelope of a virion with a ligand; determining binding between the target comprised in an envelope of a virion and the ligand; and identifying the ligand as a target for the target when the target comprised in an envelope of a virion binds to the ligand is provided.

In some aspects, a method of identifying a ligand for a target membrane bound protein comprising: contacting an array described herein with a ligand; determining binding between the target comprised in an envelope of a virion and the ligand; and identifying the ligand as a target for the target when the target comprised in an envelope of a virion binds to the ligand. In some aspects, the ligand is selected from the group consisting of peptides, lipids, fatty acids, and small molecules. In some aspects, the ligand comprises a label. In some aspects, the label is selected from the group consisting of fluorescent dyes and radioisotopes. In some aspects, the label can be a fluorescent dye selected from the group consisting of Fluo8, DiBAC4, and ANG-2. In some aspects, the identifying further comprises contacting an antibody to the ligand after (a). In some aspects, the ligand induces a conformational change in the target when bound thereto. In some aspects, the method further comprises contacting one or more antibodies to the array. In some aspects, the method further comprises identifying an antibody of the one or more antibodies as an antibody to the target comprising the induced conformational change. In some aspects, the ligand can be a drug.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

INCORPORATION BY REFERENCE

All documents, or portions of documents, cited in the application including, but not limited to, publications, patents, patent applications, articles, books, manuals, and treatises are hereby expressly incorporated by reference in their entirety for any purpose to the same extent as if each individual document was specifically and individually indicated to be incorporated by reference.

For example, all publications and patents mentioned herein are incorporated herein by reference in their entirety for the purpose of describing and disclosing the kits, compositions, and methodologies that are described in the publications, which might be used in connection with the methods, kits, and compositions described herein. The documents discussed herein are provided solely for their disclosure prior to the filing date of the present application. Nothing herein is to be construed as an admission that the inventors described herein are not entitled to antedate such disclosure by virtue of prior invention or for any other reason.

BRIEF DESCRIPTION OF THE FIGURES

Figure 1:
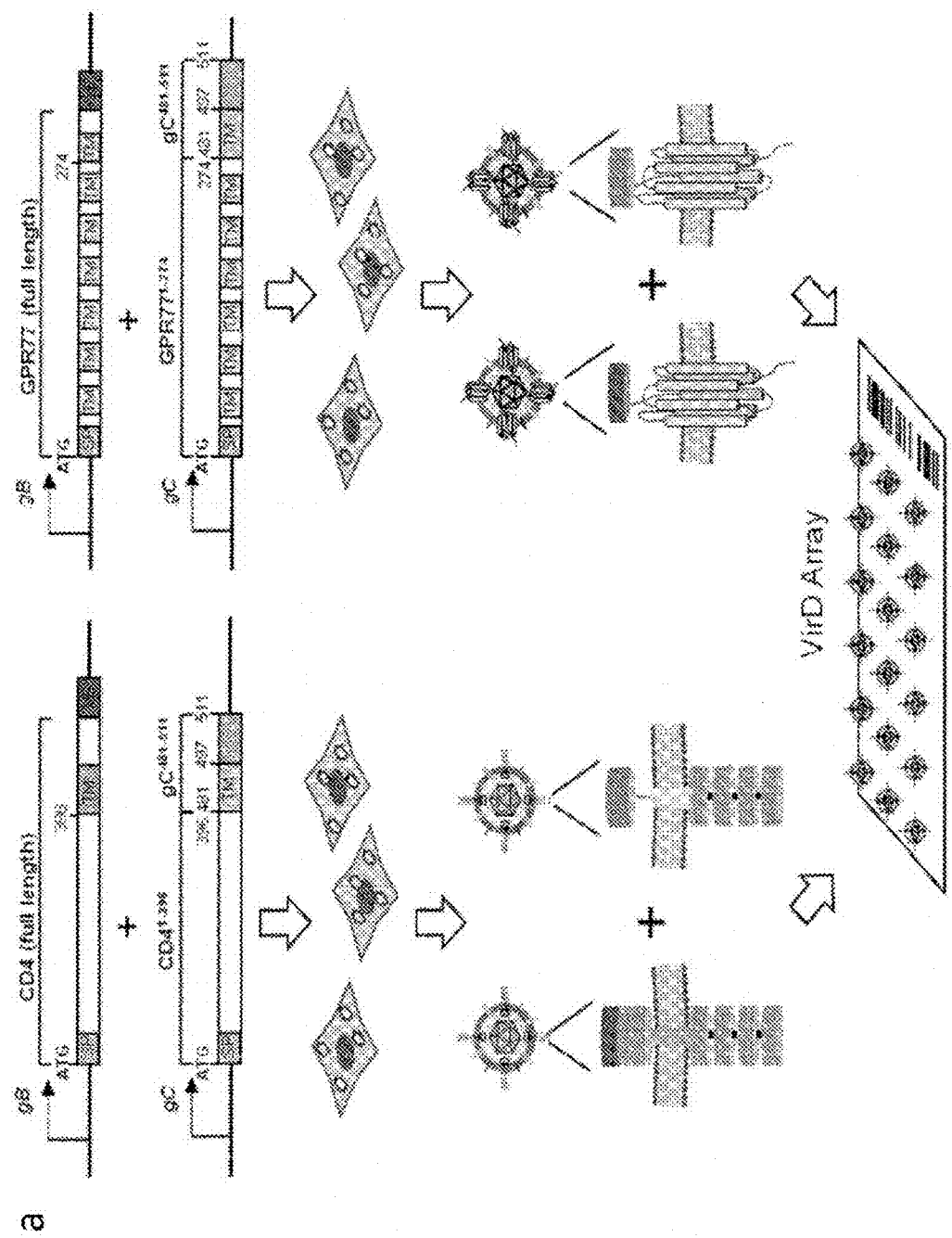
Figure 1:
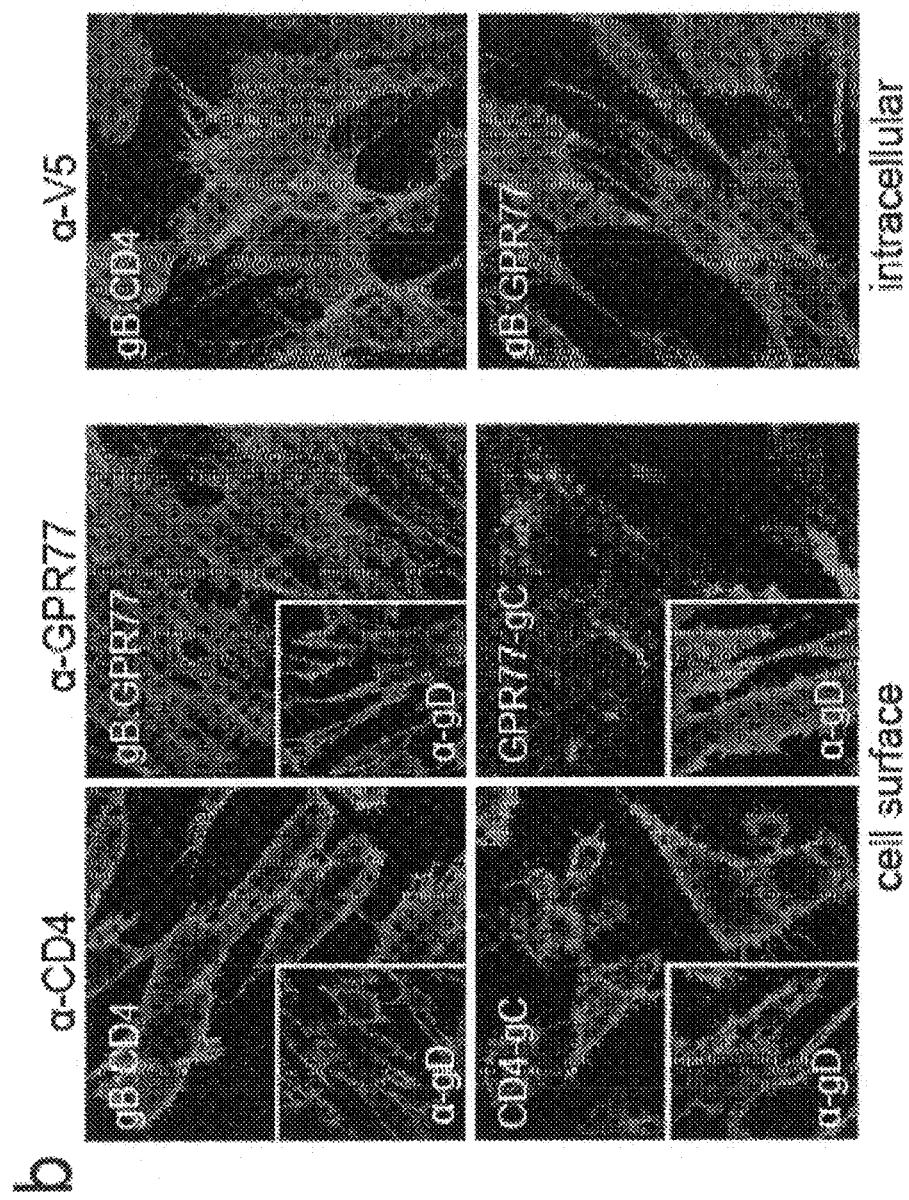
Figure 1:
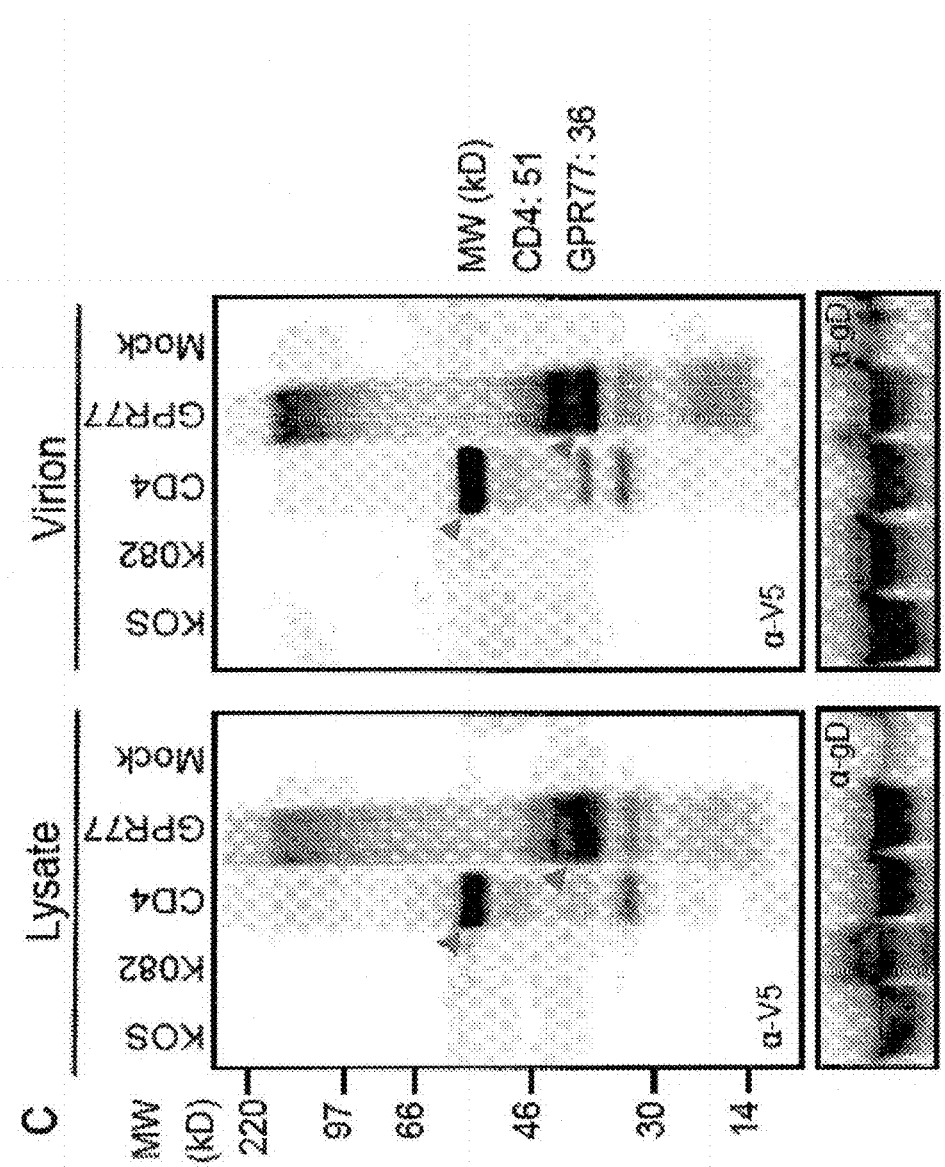
Figure 1:
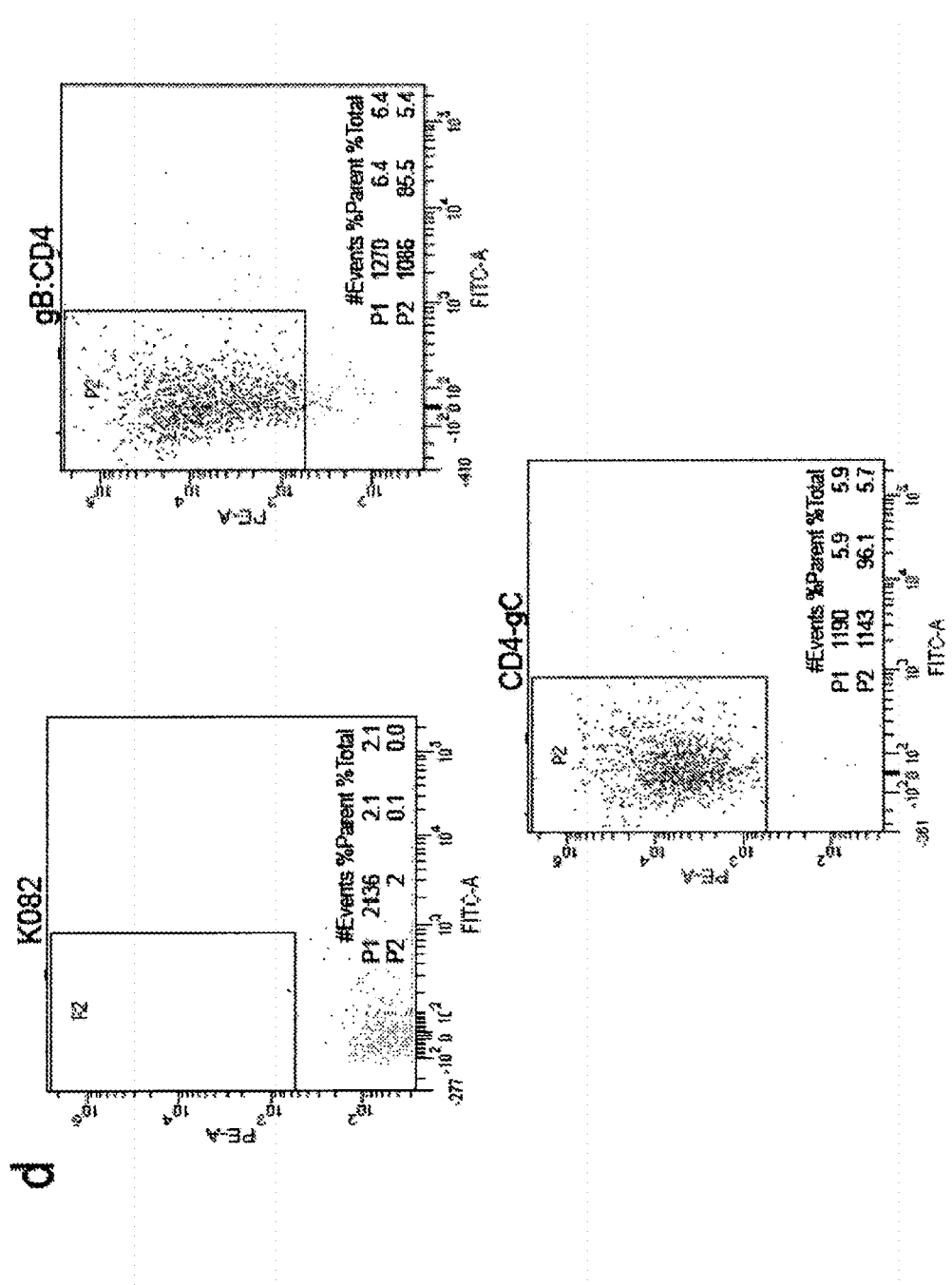

Having thus described the presently disclosed subject matter in general terms, reference will now be made to the accompanying Figures, which are not necessarily drawn to scale, and wherein:

FIG. 1 shows the development of a VirD Array. (A) Schematic of the two strategies used for the virion display system. The first utilizes expression of the CD4 or GPR77 molecule tagged with the V5 epitope from the gB promoter and the second uses a chimeric expression method by fusing the ectodomain of CD4 or GPR77 to the TM and C-terminus of glycoprotein C. The CD4 and GPR77 signal peptide (SP) is shown. Recombinant HSV-1 viruses expressing these engineered human genes were used to infect mammalian cells and the viruses released from these cells which would incorporate the human membrane protein in the virion envelope were purified and printed on FAST slides. (B) Confocal analysis of HFT cells infected with the recombinant viruses demonstrating cell surface expression of CD4 and GPR77. The cell surface expression of gD is shown for similar infected cells in the insets of each panel. Intracellular distribution of CD4 and GPR77 expressed from the gB promoter was visualized by staining with anti-V5 antibodies following permeabilization of cells. Magnification was 100×. (C) Expression of CD4 and GPR77 in infected cell lysates and incorporation of these proteins in mature virions was confirmed by western blot analysis using anti-V5 antibody. (D) The incorporation of CD4 and the conformation of the molecule in the virion was examined by labeling of purified virions with anti-CD4 (PE conjugated) antibodies followed by FACS analysis of the virions.

Figure 2:
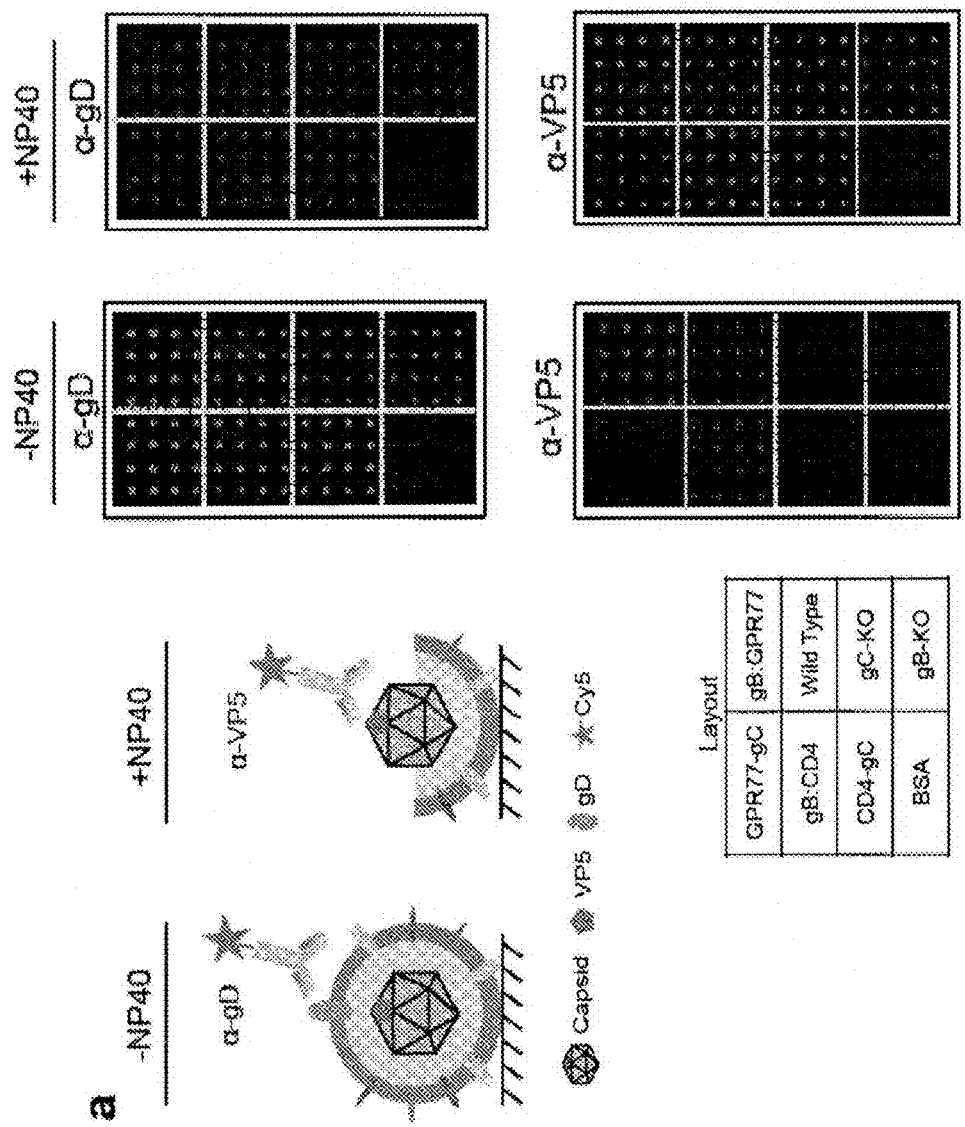
Figure 2:
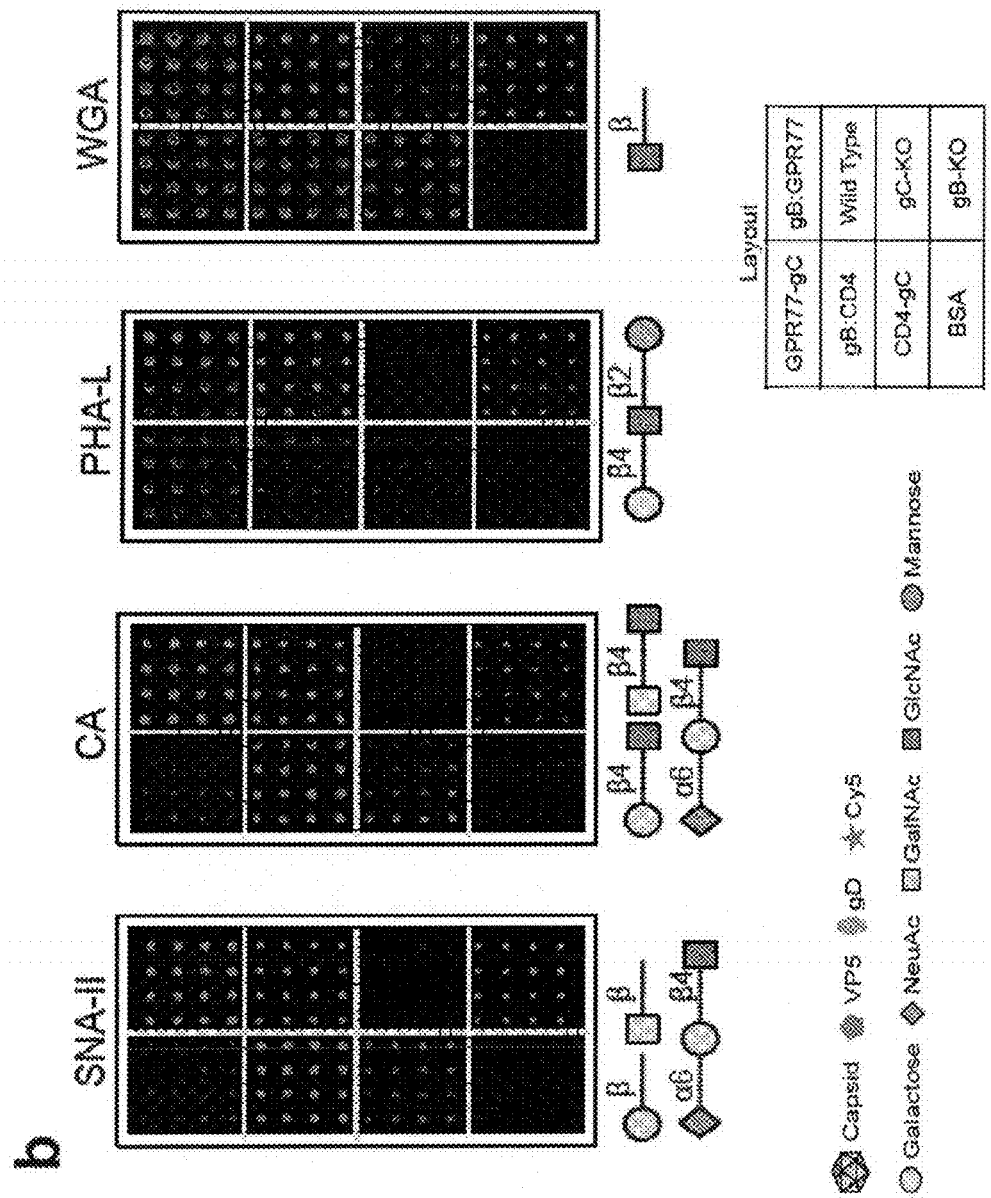
Figure 2:
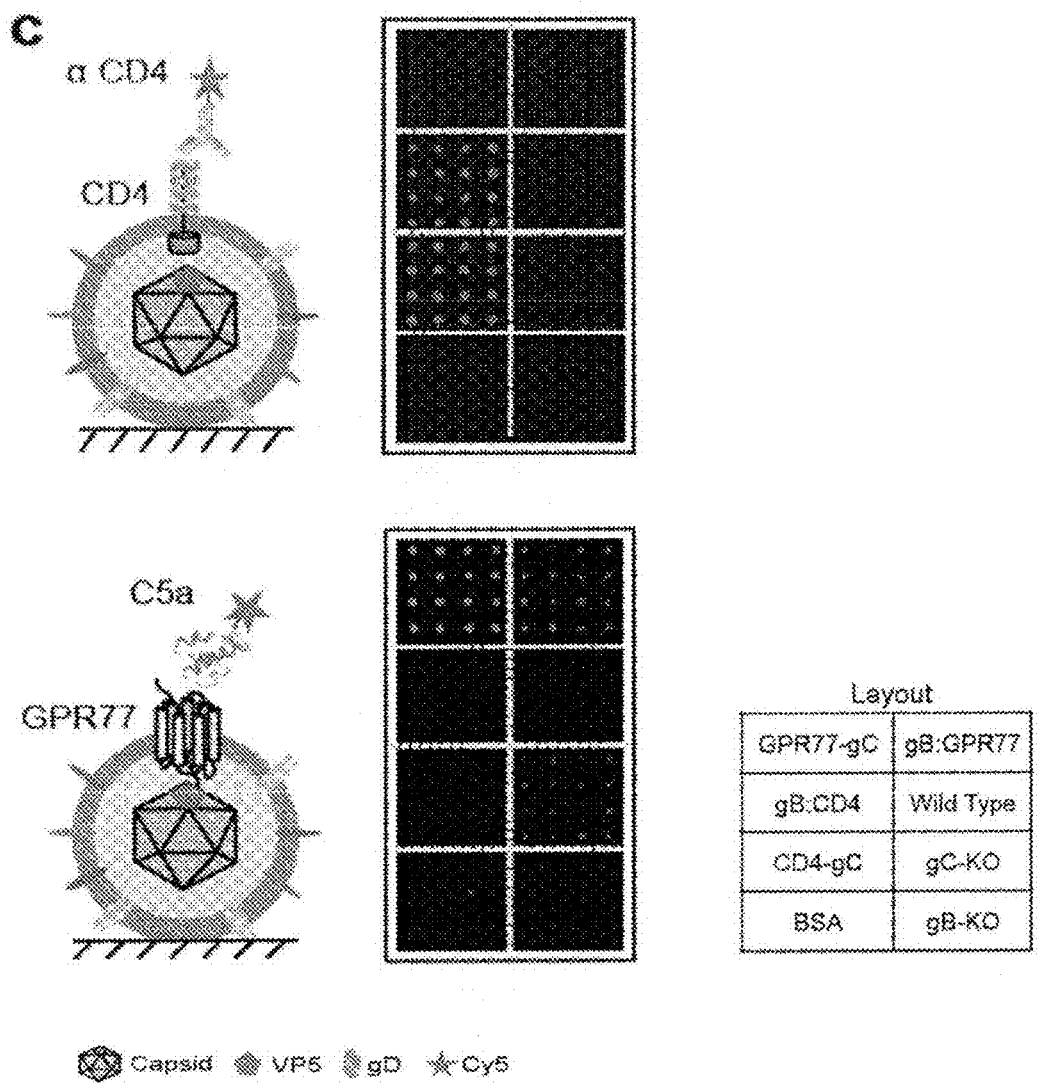
Figure 2:
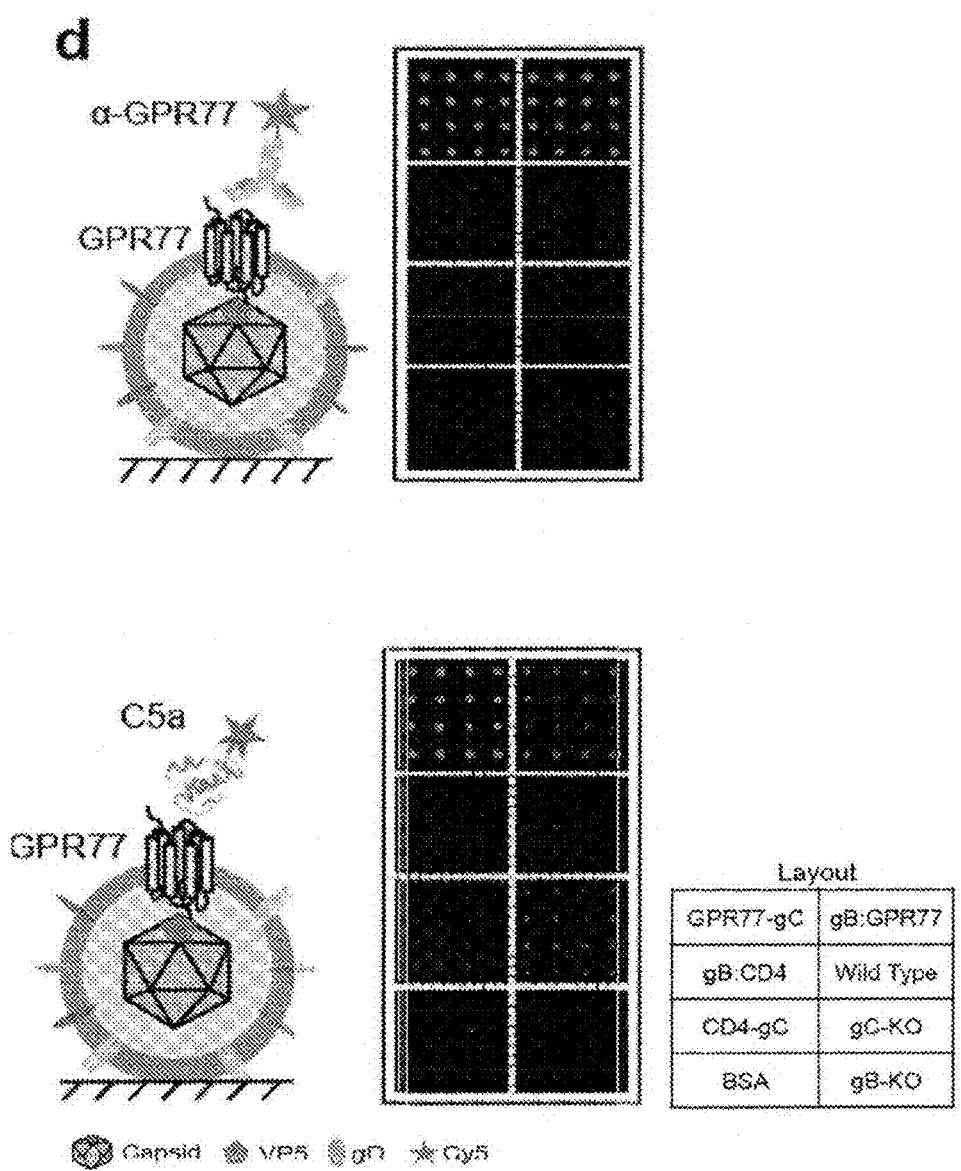

FIG. 2 shows functional and interaction assays on the VirD Arrays. The layout of the VirD Array is shown in the center of the figure. (A) Integrity of virions immobilized on VirD Arrays was confirmed by anti-gD and anti-VP5 antibodies. All seven virions showed strong anti-gD signals but much lower anti-VP5 signals. A mild detergent treatment using 1% NP40 significantly reduced the anti-gD signals and increased the anti-VP5 signals on the VirD Arrays. (B) Lectin-glycan interactions on VirD Arrays. Fluorescently labeled lectins (i.e., SNA-II, PHA-L, CA, and WGA) were probed to profile glycan structures on the VirD Arrays. (C) Anti-CD4 antibody staining. Strong and specific signals were observed on the gB:CD4 and CD4-gC virions. (D) Anti-GPR77 antibody staining and GPR77-C5a interaction. Strong and specific signals were observed on the gB:GPR77 and GPR77-gC virions, and Cy5-labeled C5a showed strong binding activity to the GPR77-gC virions and weaker binding signals to the gB:GPR77 virions but no detectable signals on other virions.

Figure 3:
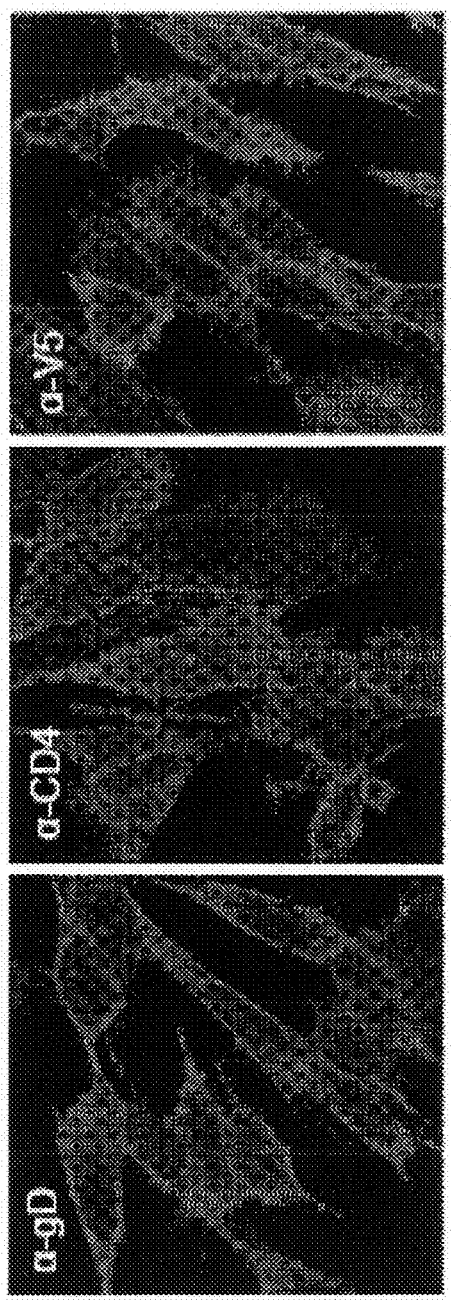

FIG. 3 shows confocal analysis of HFT cells infected with gB:CD4 showing intracellular distribution of gD and CD4. The CD4 staining was imaged using both anti-CD4 and anti-V5 antibodies demonstrating a similar distribution of CD4 within cells. Magnification was 100×.

Figure 4:
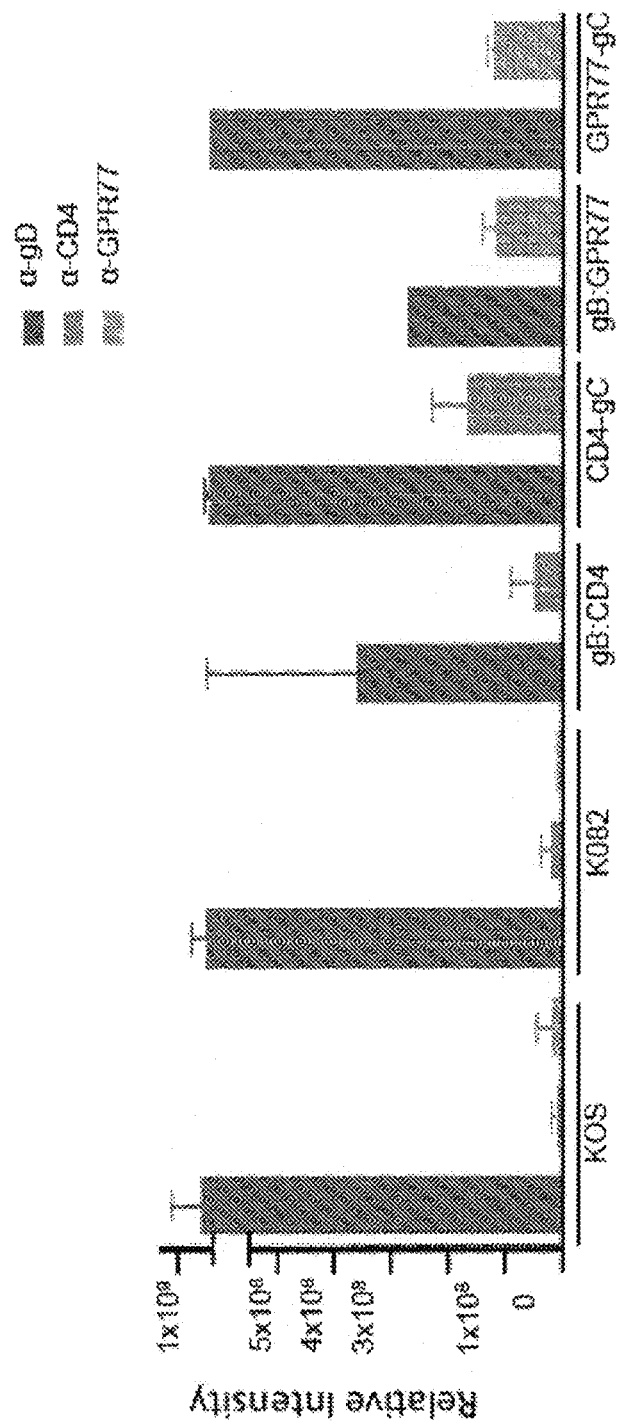

FIG. 4 shows ELISA experiments using antibodies to the ectodomain of CD4 and GPR77 was used to further demonstrate incorporation and correct display of these molecules in HSV virions.

Figure 5:
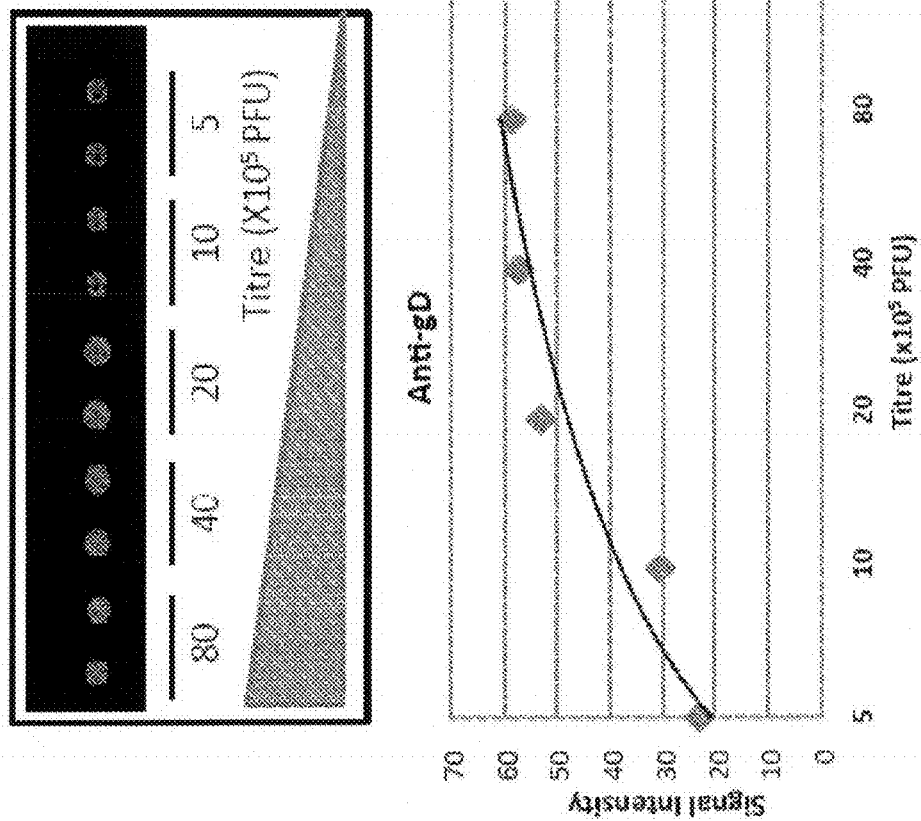

FIG. 5 shows that as low as 50,000 virions (KOS plaque forming units) per spot could be detected by anti-gD antibody on the VirD Arrays, and the anti-gD signals started to reach saturation after the titer increased to >400,000 virions.

Figure 6:
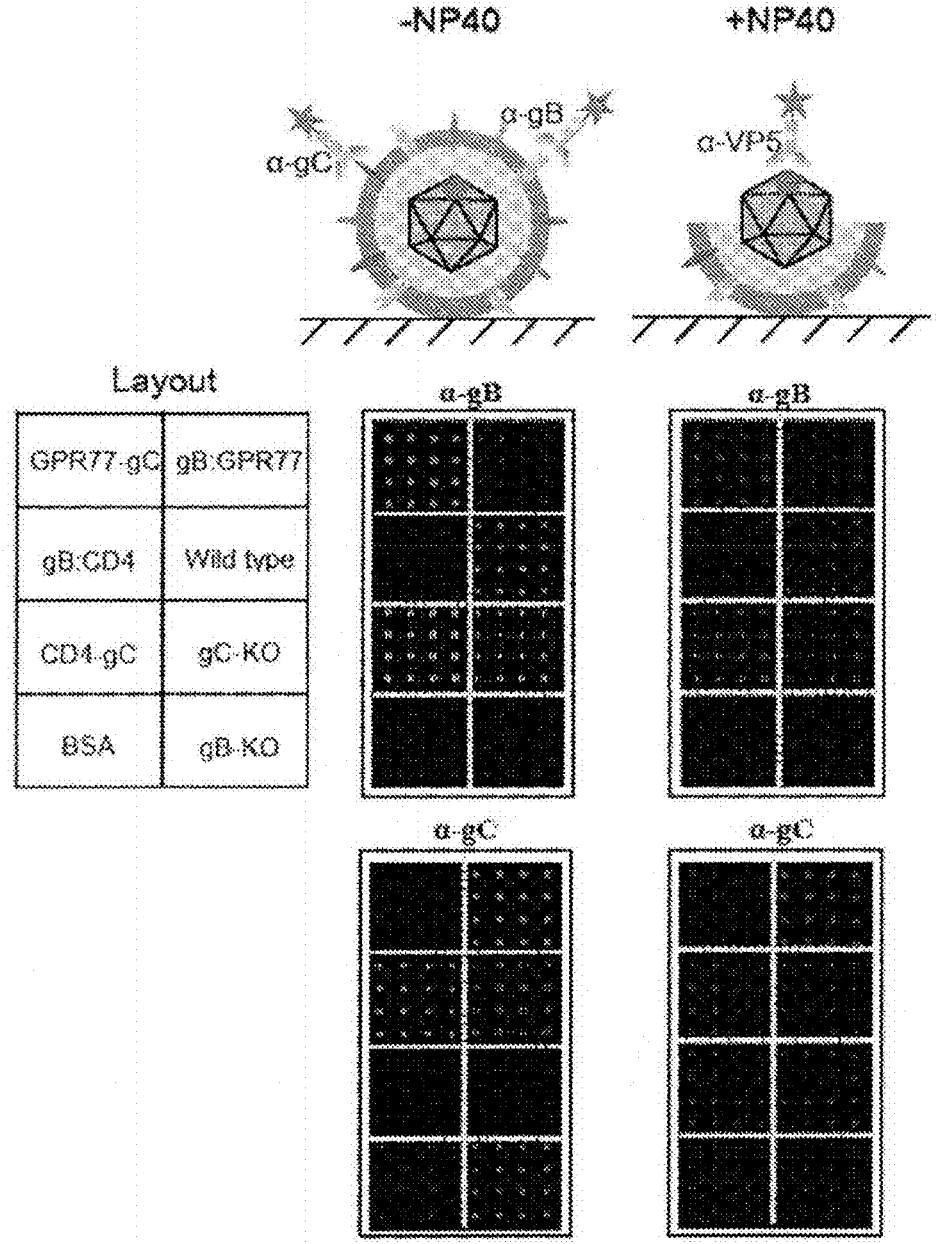

FIG. 6 shows anti-gB and anti-gC staining, confirming the absence of gB and gC proteins in gB:CD4/GPR77 and CD4/GPR77-gC virions, respectively. NP40 treatment greatly reduced the anti-gB and anti-gC signals.

Figure 7:
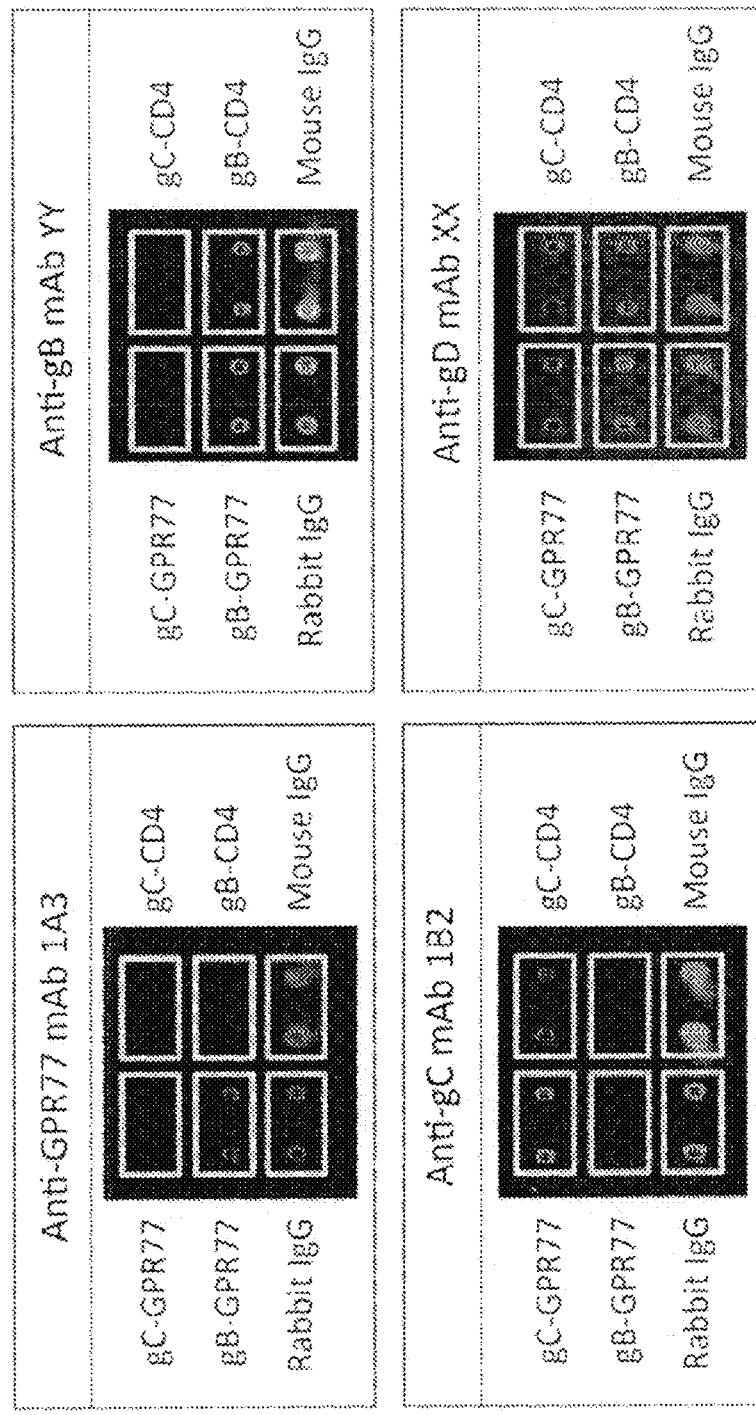

FIG. 7 shows antibodies generated against a human GPCR using recombinant HSV-1 viruses expressing the human GPCR as antigens to infect a host for antibody production.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The section headings used herein are for organizational purposes only and are not to be construed as limiting the subject matter described.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

Several aspects are described below with reference to example applications for illustration. It should be understood that numerous specific details, relationships, and methods are set forth to provide a full understanding of the features described herein. However, a person of ordinary skill in the relevant art, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting (in a manner similar to the term "comprising").

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, for example, with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

I. Recombinant Virion Arrays

The presently disclosed subject matter relates, at least in part, to the development of a novel microarray comprising human membrane proteins that retain their native conformations and/or interactions. As described more fully below, in certain aspects both single- and multiple-pass human membrane proteins may be engineered to be displayed in the envelope of virions, for example herpes simplex virions, and the purified virions may then be printed, for example, on glass slides, to form a high-density Virion Display (VirD) Array such that the displayed proteins retain their native conformations and/or interactions.

Accordingly, in one embodiment, the presently disclosed subject matter provides an array comprising a plurality of recombinant virion microspots stably associated with a surface of a substrate, wherein the recombinant virion microspots comprise a plurality of recombinant virions, wherein the recombinant virions comprise envelopes comprising a plurality of heterologous membrane bound proteins that retain their native conformations and/or interactions. In a particular embodiment, the heterologous membrane bound proteins are human membrane bound proteins.

Arrays

The arrays can each comprise at least one substrate comprising a surface having a plurality of recombinant virion microspots covering the surface. At least one or each recombinant virion microspot on the array comprises a plurality of recombinant virions, wherein the recombinant virions comprise envelopes comprising a plurality of heterologous membrane bound proteins that retain their native conformations and/or interactions, for example, human membrane bound proteins. The surface of the substrate of the array may also be covered by microspots that do not comprise a plurality of recombinant virions. For example, microspots may comprise reagents, proteins, nucleic acids, or other substances that serve as calibration spots, control spots, and the like.

The density of the all of the microspots on the surface of the substrate may be at least about $1/cm^2$ or at least about $10/cm^2$, up to about $1000/cm^2$ or up to about $500/cm^2$. In certain embodiments, the density of all the microspots on the surface of the substrate may be up to about $400/cm^2$, up to about $300/cm^2$, up to about $200/cm^2$, up to about $100/cm^2$, up to about $90/cm^2$, up to about $80/cm^2$, up to about $70/cm^2$, up to about $60/cm^2$, or up to about $50/cm^2$.

The microspots on the array may be any convenient shape, including circular, elliptoid, oval, annular, or some other analogously curved shape, where the shape may, in certain embodiments, be a result of the particular method employed to produce the array. The microspots may be arranged in any convenient pattern across or over the surface of the array, such as in rows and columns so as to form a grid, in a circular pattern, and the like, where generally the pattern of spots will be present in the form of a grid across the surface of the substrate.

In the arrays, the microspots can be stably associated with the surface of a substrate. By "stably associated" can be meant that the microspots maintain their position relative to the substrate under binding and/or washing conditions (e.g., the microspots remain in location and retain biological function when drawn through an air-water interface). Accordingly, recombinant virions or other substances comprised by the microspots can be non-covalently or covalently stably associated with the substrate surface. Examples of non-covalent association include non-specific adsorption, binding based on electrostatic (e.g. ion, ion pair interactions), hydrophobic interactions, hydrogen bonding interactions, surface hydration force and the like. Examples of covalent binding include covalent bonds formed between the recombinant virion microspot and a functional group present on the surface of the substrate (e.g. —$NH_2$) where the functional group may be naturally occurring or present as a member of an introduced coating material.

In one embodiment, only one type of heterologous membrane bound protein can be comprised by the recombinant virions in at least one or each microspot of the array. However, in certain embodiments, a single microspot may comprise recombinant virions comprising envelopes comprising multiple (i.e., two or more) different heterologous membrane bound proteins. For example, two different membrane bound proteins involved in a heterodimer pair may be included in the envelopes of recombinant virions in one microspot (see, e.g., heterodimerization of some GPCRs for their biological functions; Angers et al. (2000) *Proc. Natl. Acad. Sci. USA*, 97:3684-3689). In other embodiments, for functional activity of the heterologous membrane bound protein, the biological membrane microspot may include necessary co-effectors and/or adaptors (e.g., for GPCR activity).

Polynucleotides and Polypeptides

A "gene," as used herein, refers to a polynucleotide containing at least one open reading frame that is capable of encoding a particular protein after being transcribed and translated.

As used herein, a "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, can refer only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" can be a DNA molecule that has undergone a molecular biological manipulation.

A polynucleotide fragment refers to a nucleotide sequence of reduced length relative to the reference nucleic acid and comprising, over the common portion, a nucleotide sequence identical to the reference nucleic acid. Such a nucleic acid fragment according to the presently disclosed subject matter may be, where appropriate, included in a larger polynucleotide of which it can be a constituent. Such fragments comprise, or alternatively consist of, oligonucleotides ranging in length from at least about 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the presently disclosed subject matter.

The term "recombinant polynucleotide" can refer to polynucleotides that have been artificially designed and which comprise at least about two polynucleotide sequences that are not found as contiguous polypeptide sequences in their initial natural environment, or to refer to polypeptides which have been expressed from a recombinant polynucleotide.

The term "purified polynucleotide" or "purified polynucleotide vector" can describe a polynucleotide or polynucleotide vector which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide can be substantially pure when at least about 50%, preferably 60 to 75% of a sample exhibits a single polynucleotide sequence and conformation (linear versus covalently closed). A substantially pure polynucleotide typically comprises about 50%, preferably 60 to 90% weight/weight of a nucleic acid sample, more usually about 95%, and preferably is over about 99% pure. Polynucleotide purity or homogeneity can be indicated by a number of means well known in the art, such as agarose or polyacrylamide gel electrophoresis of a sample, followed by visualizing a single polynucleotide band upon staining the gel. For certain purposes, higher resolution can be provided by using high performance liquid chromatography (HPLC) or other means well known in the art.

The term "polypeptide" refers to a polymer of amino without regard to the length of the polymer; thus, peptides, oligopeptides, and proteins are included within the definition of polypeptide. This term also does not specify or exclude post-translation modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

The term "recombinant polypeptide" can refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified polypeptide" can describe a polypeptide that has been separated from other compounds including, but not limited to nucleic acids, lipids, carbohydrates and other proteins. A polypeptide can be substantially pure when a sample contains at least about 50%, preferably 60 to 75%, of a single polypeptide sequence. A substantially pure polypeptide typically comprises about 50%, preferably 60 to 90%, more preferably 95 to 99% weight/weight of a protein sample. Polypeptide purity or homogeneity can be indicated by a number of means well known in the art, such as agarose or polyacrylamide gel electrophoresis of a sample, followed by visualizing polypeptide bands upon staining the gel. For certain purposes, higher resolution can be provided by using HPLC or other means well known in the art.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotides could be part of a vector and/or such polynucleotide or polypeptide could be part of a composition, and still be isolated in that the vector or composition is not part of its natural environment.

The term "purified" does not require absolute purity; rather, it is intended as a relative definition. Purification of starting material or natural material to at least about one order of magnitude, preferably two or three orders, and more preferably four or five orders of magnitude is expressly contemplated. As an example, purification from 0.1% concentration to 10% concentration is two orders of magnitude.

A "purified polynucleotide" or "purified polynucleotide vector" can describe a polynucleotide or polynucleotide vector which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide can be substantially pure when at least about 50%, preferably 60 to 75% of a sample exhibits a single polynucleotide sequence and conformation (linear versus covalently closed). A substantially pure polynucleotide typically comprises about 50%, preferably 60 to 90% weight/weight of a nucleic acid sample, more usually about 95%, and preferably is over about 99% pure. Polynucleotide purity or homogeneity can be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

The term "purified polypeptide" can describe a polypeptide that has been separated from other compounds including, but not limited to nucleic acids, lipids, carbohydrates and other proteins. A polypeptide can be substantially pure when a sample contains at least about 50%, preferably 60 to 75%, of a single polypeptide sequence. A substantially pure polypeptide typically comprises about 50%, preferably 60 to 90%, more preferably 95 to 99% weight/weight of a protein sample. Polypeptide purity or homogeneity can be indicated by a number of means well known in the art, such as agarose or polyacrylamide gel electrophoresis of a sample, followed by visualizing polypeptide bands upon staining the gel. For certain purposes higher resolution can be provided by using HPLC or other means well known in the art.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e., the succession of letters chosen among the four base letters) that biochemically characterizes a specific DNA or RNA molecule.

As used interchangeably herein, the terms "nucleic acids," "oligonucleotides," and "polynucleotides" include RNA, DNA, or RNA/DNA hybrid sequences of more than one nucleotide in either single chain or duplex form. The term "nucleotide" can be used herein as an adjective to describe molecules comprising RNA, DNA, or RNA/DNA hybrid sequences of any length in single-stranded or duplex form. The term "nucleotide" can be also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide"

can be also used herein to encompass "modified nucleotides" which comprise at least one of the following modifications: (a) an alternative linking group, (b) an analogous form of purine, (c) an analogous form of pyrimidine, or (d) an analogous sugar. For examples of analogous linking groups, purine, pyrimidines, and sugars, see for example PCT Patent App. Pub. No. WO 95/04064. The polynucleotide sequences may be prepared by any known method, including synthetic, recombinant, ex vivo generation, or a combination thereof, as well as utilizing any purification methods known in the art.

The term "promoter" refers to a DNA sequence capable of controlling the expression of a coding sequence or functional RNA. In general, a coding sequence can be located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

A "promoter sequence" can be a DNA regulatory region capable of binding RNA polymerase in a cell and initiating transcription of a downstream (3' direction) coding sequence. For purposes of defining the presently disclosed subject matter, the promoter sequence can be bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence can be "under the control" of transcriptional and translational control sequences in a cell when RNA polymerase transcribes the coding sequence into mRNA, which can be then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "operably linked" refers to the association of nucleic acid sequences on a single nucleic acid fragment so that the function of one can be affected by the other. For example, a promoter can be operably linked with a coding sequence when it is capable of affecting the expression of that coding sequence (i.e., that the coding sequence can be under the transcriptional control of the promoter). Coding sequences can be operably linked to regulatory sequences in sense or antisense orientation.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

The term "primer" denotes a specific oligonucleotide sequence which can be complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment which can be used to identify a specific polynucleotide sequence present in samples, wherein the nucleic acid segment comprises a nucleotide sequence complementary to the specific polynucleotide sequence to be identified.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Berg et al. (2011) *Biochemistry*, $7^{th}$ revised international ed., ISBN-10:1429276355).

The terms "complementary" or "complement thereof" are used herein to refer to the sequences of polynucleotides that are capable of forming Watson & Crick base pairing with another specified polynucleotide throughout the entirety of the complementary region. For the purpose of the presently disclosed subject matter, a first polynucleotide is deemed to be complementary to a second polynucleotide when each base in the first polynucleotide is paired with its complementary base. Complementary bases are, generally, A and T (or A and U), or C and G. "Complement" can be used herein as a synonym from "complementary polynucleotide," "complementary nucleic acid" and "complementary nucleotide sequence". These terms are applied to pairs of polynucleotides based solely upon their sequences and not any particular set of conditions under which the two polynucleotides would actually bind.

The presently disclosed subject matter also relates to variants and fragments of the polynucleotides described herein. Variants of polynucleotides, as the term can be used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the presently disclosed subject matter include, without being limited to, nucleotide sequences which are at least about 70% identical, e.g., at least about 75%, 80%, 85%, 90%, 91%, 92%, 93%, 94%, 95%, 96%, 97%, 98%, or 99% identical to a reference polynucleotide or to any polynucleotide fragment of at least about 8 consecutive nucleotides of a reference polynucleotide, and preferably at least about 99.5% identical, and more preferably at least about 99.8% identical to a reference polynucleotide or to any polynucleotide fragment of at least about 8 consecutive nucleotides of a reference polynucleotide.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

Particularly preferred embodiments are those in which the polynucleotides encode polypeptides that retain substantially the same biological function and/or activity as the mature membrane bound protein.

A polynucleotide fragment refers to a nucleotide sequence of reduced length relative to the reference nucleic acid and comprising, over the common portion, a nucleotide sequence substantially identical to the reference nucleic acid. Such a nucleic acid fragment according to the presently disclosed subject matter may be, where appropriate, included in a larger polynucleotide of which it can be a constituent. Such fragments comprise, or alternatively consist of, oligonucleotides ranging in length from at least about 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the presently disclosed subject matter.

Such fragments may be "free-standing," i.e. not part of or fused to other polynucleotides, or they may be comprised within a single larger polynucleotide of which they form a part or region. Indeed, several of these fragments may be present within a single larger polynucleotide.

Optionally, such fragments may consist of, or consist essentially of a contiguous span of at least about 8, 10, 12, 15, 18, 20, 25, 35, 40, 50, 70, 80, 100, 250, 500 or 1000 nucleotides in length.

As described herein, isolated, purified, and recombinant polypeptides may comprise a contiguous span of at least about 6 amino acids, preferably at least about 8 to 10 amino acids, more preferably at least about 12, 15, 20, 25, 30, 40, 50, or 100 amino acids of a reference sequence. In other preferred embodiments the contiguous stretch of amino acids comprises the site of a mutation or functional mutation, including a deletion, addition, swap or truncation of the amino acids in a polypeptide sequence.

Polypeptides may be isolated from human or mammalian tissue samples or expressed from human or mammalian genes. Polypeptides may be made using routine expression methods known in the art. The polynucleotide encoding a desired polypeptide may be ligated into an expression vector suitable for any convenient host. Both eukaryotic and prokaryotic host systems are used in forming recombinant polypeptides, and a summary of some of the more common systems is provided herein. The polypeptide may then be isolated from lysed cells or from the culture medium and purified to the extent needed for its intended use. Purification may be by any technique known in the art, for example, differential extraction, salt fractionation, chromatography, centrifugation, and the like (See, for example, Abbondanzo et al. (1993) Methods in Enzymology, Academic Press, New York. pp. 803-823).

In addition, shorter protein fragments may be produced by chemical synthesis. Alternatively proteins are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis, for example.

Reference cDNA may be used to express polypeptides. The nucleic acid encoding the polypeptide to be expressed can be operably linked to a promoter in an expression vector using conventional cloning technology. For example, a membrane bound polypeptide in the expression vector may comprise the full coding sequence for the polypeptide or a portion thereof. For example, the insert may encode a polypeptide comprising at least about 10 consecutive amino acids of a membrane bound polypeptide.

The term "percent identity," as known in the art, can be a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters, including default parameters for pairwise alignments.

The term "sequence analysis software" refers to any computer algorithm or software program that can be useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al. (1990) *J. Mol. Biol.* 215:403-410, and DNASTAR (DNASTAR, Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Membrane Bound Proteins

The terms "membrane bound protein" and "membrane bound polypeptides" are used interchangeably herein to refer to both single- and multiple-pass membrane bound proteins, for example, human membrane bound proteins. Also forming part are polypeptides encoded by the polynucleotides, as well as fusion polypeptides comprising such polypeptides. The presently disclosed subject matter embodies membrane bound polypeptides from humans, including isolated or purified membrane bound polypeptides consisting of, consisting essentially of, or comprising a reference amino acid sequence for a given membrane bound polypeptide, or variants or fragments thereof.

In one embodiment, the membrane bound protein can be CD4, a classical type I membrane protein with a single TM domain. CD4 is a well-characterized membrane glycoprotein of T lymphocytes that interacts with major histocompatibility complex class II antigens and is also a receptor for the human immunodeficiency virus (Carr et al. (1989) *J. Biol. Chem.* 264:21286-95).

In another embodiment, the membrane bound protein can be GPR77, a multi-spanning, G-protein coupled receptor (GPCR) membrane protein. GPR77 is involved in the complement system of the innate immune response with a canonical ligand identified (i.e., complement component C5a) (Cain & Monk (2002) *J. Biol. Chem.* 277:7165-9).

Additional exemplary membrane bound proteins include, but are not limited to, GPCRs (e.g. the adrenergic receptor, angiotensin receptor, cholecystokinin receptor, muscarinic acetylcholine receptor, neurotensin receptor, galanin receptor, dopamine receptor, opioid receptor, erotonin receptor, somatostatin receptor, etc.), ion channels (nicotinic acetylcholine receptor, sodium and potassium channels, etc.), receptor tyrosine kinases, receptor serine/threonine kinases, receptor guanylate cyclases, receptors for growth factors and hormones (epidermal growth factor (EGF) receptor), and other membrane-bound proteins. Mutants or modifications of such proteins may also be used. For example, some single or multiple point mutations of GPCRs retain function and may be involved in disease (See, e.g., Stadel et al. (1997) *Trends in Pharmocological Review* 18:430-437).

In one embodiment, the envelopes of the plurality of recombinant virions within the recombinant virion array comprise only one type of heterologous membrane bound proteins that retain their native conformations and/or interactions. In another embodiment, the envelopes comprise more than one type of heterologous membrane bound proteins that retain their native conformations and/or interactions. For example, some GPCRs heterodimerize for their biological functions (Angers et al. (2000) *Proc. Natl. Acad. Sci. USA*, 97:3684-3689). In one embodiment, the membrane bound proteins comprised by the envelope of one or more of the plurality of recombinant virions in one location of the recombinant virion array differs from the membrane bound proteins comprised by the envelope of one or more of the plurality of recombinant virions in one or more separate locations of the recombinant virion array. Accordingly, in another embodiment, a plurality of different membrane bound proteins can be present at separate locations of the recombinant virion array. In some embodiments, the recombinant virion array comprises at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 different membrane bound proteins. In other embodiments, the recombinant virion array comprises more than about $10^3$ different membrane bound proteins or more than about $10^4$ different membrane bound proteins, and may even optionally comprise more than about $10^5$ different membrane bound proteins.

In another embodiment, although the envelopes may comprise more than one type of heterologous membrane bound proteins that retain their native conformations and/or interactions, the proteins are related. Accordingly, in one embodiment, two or more different membrane bound proteins comprised by the envelopes are members of the same protein family. The different membrane bound proteins may be either functionally related or just suspected of being functionally related. In another embodiment, the function of the immobilized membrane bound proteins may be unknown, with different membrane bound proteins at separate locations of the recombinant virion array sharing a similarity in structure or sequence or simply suspected of sharing a similarity in structure or sequence.

In another alternative embodiment, at least one or each of the microspots of the array comprises the same type of heterologous membrane bound protein of interest but in different versions, for example at least one or each of the microspots of the array comprises a different variant of the same protein of interest (i.e., with different point mutations, deletions, substitutions, and the like), for example, wherein at least one or each of the microspots of the array comprises a different variant of the same heterologous membrane bound protein. The resulting arrays can be used to systematically examine the structure and function relationship of the heterologous membrane bound protein.

In another embodiment, the array may comprise substantially identical microspots (e.g., microspots comprising the same type of heterologous membrane bound proteins) or a series of substantially identical microspots, but that in use are treated with a different analyte (target). For example, an array may include "subarrays," e.g. of 10, 15, 20, 25, 30, 35, 40, 45, 50 or more microspots, with at least one or each microspot comprising a different membrane bound protein, and wherein the subarray can be repeated multiple times as part of the larger array.

In another embodiment, although the heterologous membrane bound protein of one microspot can be different from that of another, the proteins can be related. For example, in one embodiment the two different heterologous membrane bound proteins are members of the same protein family. The different heterologous membrane bound proteins on the invention array may be either functionally related or just suspected of being functionally related. However, in another embodiment, the function of the heterologous membrane bound proteins may be unknown and the different heterologous membrane bound proteins on the different microspots of the array share a similarity in structure or sequence or are simply suspected of sharing a similarity in structure or sequence. Alternatively, the heterologous membrane bound proteins may be fragments of different members of a protein family. In a further embodiment, the heterologous membrane bound proteins share similarity in pharmacological and physiological distribution or roles.

Recombinant Virions

Recombinant virions for use within the can comprise envelopes comprising a plurality of heterologous membrane bound proteins that retain their native conformations and/or interactions. A virus can be a small infectious agent that can replicate only inside the living cells of an organism. Virus particles are known as virions typically comprise several parts: 1) genetic material made from either DNA or RNA; 2) a protein coat, typically called a capsid, that protects the genetic material; and, in some cases, 3) an envelope of lipids that surrounds the protein coat when they are outside of a cell.

For use within the array, recombinant virions can be made as set forth in the Examples or by other methods of making recombinant virions as described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Similar methods are used to introduce a heterologous gene of interest in methods of making the recombinant virions described herein. For example, recombinant virions can be constructed using homologous recombination after DNA co-transfection, in which cells may be co-transfected with at least two different viruses containing genes of interest and progeny virus plaque may be purified. Final verification of the correct genetic organization of recombinant virions can be verified by DNA hybridization studies using probes to the nucleic acids. The heterologous nucleic acid sequences encoding heterologous membrane bound proteins may be obtained using standard cloning and screening techniques, from natural sources such as genomic DNA libraries or can be synthesized using well known and commercially available techniques.

In one embodiment, the heterologous membrane bound proteins are human membrane bound proteins and the recombinant virions are recombinant Herpes Simplex Virus (HSV) virions, for example, Herpes simplex virus type 1 (HSV-1) or type 2 (HSV-2), for example, HSV-1. Herpesviridae can be the name of a family of enveloped, double-stranded DNA viruses with relatively large complex genomes that replicate in the nucleus of a wide range of vertebrate hosts, including humans, horses, cattle, mice, pigs, chickens, turtles, lizards, fish, and even in some invertebrates, such as oysters. All herpes virus virions have four structural elements: 1) a core of a single linear molecule of double stranded DNA; 2) a capsid protein coat; 3) a tegument comprising an amorphous and sometimes asymmetrical space between the DNA core and the protein capsid that comprises viral enzymes; and 4) an envelope that comprises an altered host membrane as well as a number of viral glycoproteins and other membrane proteins.

The HSV viral genome is well characterized as is its life cycle, and the functions of more than 80 native coding polynucleotides are largely defined. Because the HSV genome is so well characterized, it is readily manipulated for use as a gene transfer vector, a feature enhanced by the fact that HSV genes are generally contiguous linear sequences. Furthermore, as roughly half of its genes are dispensable for growth, the possibility exists of deleting large segments of the HSV genome to accommodate transgenic material (Glorioso et al. in Viral Vectors, Academic Press, New York (Kaplitt & Loewy, eds.) 1-23 (1995)).

Primary HSV infection begins by introducing the virus into a host cell, a process involving two distinct stages: attachment of the virus to the cell surface and fusion of the viral envelope with the cell membrane. Once the virus has entered a cell, it can be transported to the nucleus, whereupon the viral DNA can be released and transcribed in three distinct phases of lytic infection. The attachment and fusion steps of HSV infection are mediated primarily by components of the viral envelope, a membranous structure containing at least about 10 glycoproteins (gB, gC, gD, gE, gG, gH, gI, gJ, gL, and gM) and four non-glycosylated integral membrane proteins ($U_L20$, $U_L34$, $U_L45$, and $U_L49.5$). Of the glycoproteins, gB, gD, gH, and gL are essential for wild type herpes viruses to infect their host cells, while the remainder are dispensable for viral attachment or internalization. Prior to HSV-1 entry, virions are adsorbed to the cell surface through binding of gC and gB, to exposed glycosaminoglycans on the cell membrane. The entry process can be then initiated by the interaction of gD with one of its cognate receptors, such as herpes virus entry mediator (HVEM) or nectin-1. Receptor binding results in a conformational change in gD triggering activation of gB and a fourth envelope glycoprotein, gH, as the effectors of fusion between the viral envelope and cell membranes.

In one embodiment, the KOS strain of HSV-1 can be used as the wild-type virus.

In one embodiment, recombinant virions comprise one or more transgene expression cassettes (i.e., a polynucleotide for expression operably linked to a promoter, optionally including polyadenylation sequences or other processing sequences). Such transgene expression cassettes comprise a polynucleotide sequence encoding one or more heterologous membrane bound proteins.

In one embodiment, a recombinant HSV-1 virion for use within the recombinant virion array can be produced by cloning a polynucleotide sequence encoding a heterologous membrane bound protein into a locus of the HSV-1 genome that can be operably linked to an HSV-1 promoter sequence. For example, the polynucleotide sequence may be a full-length human open reading frame (ORF) encoding a heterologous membrane bound protein, and the ORF encoding a heterologous membrane bound protein may be cloned at the gB locus and expressed under the control of the strong gB promoter.

In another embodiment, a recombinant HSV-1 virion for use within the recombinant virion array can be produced by cloning a polynucleotide sequence encoding a fusion or chimeric protein into a locus of the HSV-1 genome that can be operably linked to an HSV-1 promoter sequence, wherein the fusion protein comprises a heterologous membrane bound protein fused (or attached) to an HSV-1 envelope protein or fragments thereof. For example, the polynucleotide sequence may comprise the full-length human ORF encoding a heterologous membrane bound protein fused (or attached) to a nucleotide sequence encoding the transmembrane (TM) and cytoplasmic domains of gC, and the polynucleotide sequence encoding the fusion protein nay be cloned at the gC locus and expressed under the control of the gC promoter (See, e.g., Dolter et al. (1993) *J. Virol.* 67:189-95; Kouvatsis et al. (2007) *Virus Res.* 123:40-9).

The terms "fusion" and "chimeric" or "chimera" are used interchangeably and refer to a polypeptide or protein created by joining two or more polypeptide sequences which are naturally not joined together, or a polynucleotide or gene created by joining two or more polynucleotide sequences which are naturally not joined together. For example, a fusion polypeptide may be expressed from a single fusion polynucleotide encoding the fusion polypeptide.

HSV-1 envelope glycoproteins are naturally positioned in the envelope suitably for contact with extraviral surfaces. Accordingly, chimeric envelope proteins for use within the recombinant virion array may preferably involve native glycoproteins. Because, gB, gC, and gD each mediate viral attachment to the cell surface, chimeric proteins for use within the recombinant virion array, for example, may include of gB, gC, and/or gD, or fragments thereof.

Chimeric proteins comprising a heterologous membrane bound protein may include other non-native elements as well. For example, the heterologous membrane bound protein may be incorporated into the chimeric protein attached to a linker or spacer polypeptide. Such a spacer may permit, for example, the heterologous membrane bound protein to be added to the protein without appreciably perturbing the overall protein structure.

The recombinant HSV virions can be modified to carry a heterologous gene, that is to say a gene other than one naturally present in the HSV genome. The term "heterologous gene" refers to any gene that is not native (i.e., foreign) to a cell or organism of interest, e.g., a gene that is not native to HSV. The heterologous gene may be any allelic variant of a wild-type gene, or it may be a mutant gene. Similarly, a "heterologous protein" or "heterologous polypeptide" can be any protein or polypeptide that is not native (i.e., foreign) to a cell or organism of interest, e.g., a protein or polypeptide that is not native to HSV.

The heterologous gene may be inserted into the HSV genome by homologous recombination of HSV strains with, for example, plasmid vectors carrying the heterologous gene flanked by HSV sequences. The heterologous gene may be introduced into a suitable plasmid vector and introduced into a host cell and the host cell can be infected with a virus to produce virion comprising a heterologous membrane protein. The heterologous gene may be introduced into a suitable plasmid vector comprising HSV sequences using cloning techniques well-known in the art. The heterologous gene may be inserted into the HSV genome at any location provided that the virus can still be propagated with its envelope comprising the heterologous protein. In a particular embodiment, the heterologous gene can be inserted at the locus of an endogenous gene and can be expressed under the control of the endogenous gene's promoter (e.g., cloned at the gB locus and expressed under the control of the gB promoter, or cloned at the gC locus and expressed under the control of the gC promoter).

The transcribed sequence of the heterologous gene can be preferably operably linked to a control sequence permitting expression of the heterologous gene, provided that the virus can still be propagated with its envelope comprising the heterologous protein. The control sequence comprises a promoter allowing expression of the heterologous gene and a signal for termination of transcription. The promoter can be selected from promoters which are functional in selected virions, e.g. promoters of HSV genes.

In some embodiments, an open reading frame (ORF) of interest can replace either a coding region of herpes virus gB or gC gene in the HSV genome. In some embodiments, expression of the ORF of interest can be tightly controlled by the gB or gC promoter. In some embodiments, the amount of the human proteins produced by at least one or each recombinant virus in a host can be about the same. Some viruses tightly control the copy number of their envelope proteins to be assembled to at least one or each virion. Therefore, a protein expressed by the virus can have roughly the same copy numbers per virion.

In some embodiments, the amount of protein present in a virion spotted on an array can be about equivalent to the amount of one or more other proteins in one or more other virions on the array. For example, the amount of protein present in a virion spotted on an array can be about 50%, 60%, 70%, 80%, 85%, 90%, 95%, 98%, or 99% of the amount of one or more other proteins in one or more other virions on the array.

The expression cassette can be constructed using routine cloning techniques known to persons skilled in the art (see, for example, Sambrook et al. (1989) Molecular Cloning—a laboratory manual; Cold Spring Harbor Press). Furthermore, the construction of particular recombinant HSV virions is described in the Examples.

In some embodiments, the expression of multiple genes may be advantageous. For such applications HSV is uniquely appropriate as it does not have the limited packaging capabilities of other viral vector systems. Thus multiple heterologous genes can be accommodated within its genome. There are, for example, at least two ways in which this could be achieved. For example, more than one heterologous gene and associated control sequences could be introduced into a particular HSV strain. It would also be possible to use pairs of promoters (the same or different promoters) facing in opposite orientations, these promoters each driving the expression of a heterologous gene (the same or different heterologous gene) as described above. Alternatively heterologous genes may be inserted at multiple sites within the HSV genome.

Many membrane proteins, such as GPCRs, function as heterodimers or hetromultimers. In some embodiments, virions displaying these types of molecules using combinatorial co-infection of cells with viruses expressing those particular membrane proteins can be used. These virions produced can display both membrane proteins, such as GPCRs, as a complex that can be produced during co-expression in the cell.

In some embodiments, multi-path membrane bound proteins, such as GPCRs and channels, can be engineered to reverse their topology based on the "positive-inside" rule. For example, a cytosolic domain of such an engineered membrane protein can be displayed as ectodomains on a recombinant virion surface. The resulting recombinant virus can be used to identify proteins or other biomolecules that interact with the cytosolic domains of these membrane proteins.

Mammalian, yeast, insect and bacterial expression systems are known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for expression in the organism in which the expression vector can be introduced, as explained by Hatfield, et al., U.S. Pat. No. 5,082,767.

In a preferred embodiment, the presently disclosed subject matter relates to a recombinant HSV-1 bacterial artificial chromosome (BAC) clone encoding a heterologous membrane polypeptide. The BAC cloning system (Shizuya et al. (1992) *Proc. Natl. Acad. Sci. U.S.A.* 89:8794-8797) has been developed to stably maintain large fragments of genomic DNA (100-300 kb).

In one embodiment, plasmid pKΔ4B (Cai et al. (1988) *J. Mol. Biol.* 201:575-88) may be used following engineering of linker-insertion mutants in the glycoprotein B gene, wherein DNA sequences encoding amino acids 43 through 711 of gB are deleted and a BglII restriction site added to maintain the protein reading frame (Cai et al. (1988) *J. Mol. Biol.* 201:575-88). The pKΔ4B plasmid may be digested, for example, with Xho1 and BglII, treated with antartic phosphatase (NEB) and ligated with an Xho1-BglII PCR fragment amplified from pKΔ4B which deletes all gB amino acids from 1-43 (gBΔSS) but retains the gB promoter sequences (referred to herein as plasmid pKgBΔSS). The sequence of gB amino acids spanning 711 to 796 may then be deleted from pKgBΔSS by cassette PCR mutagenesis, with the PCR fragment cloned as a BglII-BamH1 into pKgBΔSS and the resulting plasmid referred to herein as pKgBPR. Heterologous membrane bound proteins may then be amplified from the plasmids, for example from the Ultimate ORF collection (Life Technologies). The sequence encoding the V5 epitope may be included in the reverse primer. Sequence analysis of the final gB promoter driven gene plasmids may be done prior to introduction into the virus genome, and plasmids may be linearized with BamH1 for homologous recombination. A marker rescue and marker transfer assay may then be performed, for example the marker rescue of UL28 and marker transfer of the heterologous membrane bound protein operably linked gB promoter sequences using the method described in Desai et al. (Desai et al. (1994) *Virology* 204:312-22). A1.1 cell monolayers (UL27 and UL28 transformed cells; Tengelsen et al. (1993) *J. Virol.* 67:3470-80) may be co-transfected with infected cell DNA (KΔ4BX) and linearized plasmid DNA, for example using the calcium phosphate precipitation method. When plaques begin to appear, the cell monolayers may be harvested, and optionally freeze/thawed and sonicated, and total virus progeny titered. Recombinant virus may be isolated by single plaque purification on D6 cells (UL27 transformed; Cai et al. (1987) *J. Virol.* 61:714-21), and additional plaque purification may be carried out by limiting dilution on a D6 cell line.

In another embodiment, the KOS BAC37 genome (Gierasch et al. (2006) *J. Virol. Methods* 135:197-206) may be transferred into TOP10 cells (Stratagene), and chimeric fusion proteins comprising a heterologous membrane bound protein fused to an HSV-1 envelope protein or fragments thereof, e.g. gC, may be introduced into the virus genome used the Gene Bridges Red-ET method and the protocols provided (Zhang et al. (2000) *Nat. Biotechnol.* 18:1314-7). For example, the kanamycin cassette surrounded by gC homologous sequences may be amplified and the kanamycin gene introduced into KOS BAC37 replacing the gC gene. Colonies growing on kanamycin plates may be screened for streptomycin sensitivity, gC fusion genes may be made using Overlap PCR methods (e.g., using primers listed in Table 1), and gC fusion polynucleotides may be amplified using RedET primers (e.g. as listed in Table 1) and used to replace the kanamycin gene. Successful isolates carrying the correct fusion polynucleotides may be identified by PCR assays and the inserted gene in the BAC genome may be sequenced prior to reconstitution of infectious virus. The KOS Bacmids carrying glycoprotein C chimera gene fusions may be prepared using the PureLink nucleic acid purification kit (Life Technologies), and the Bacmid DNA transfected into Vero cells using Lipofectamine 2000 reagent (Life Technologies). Upon plaque formation, infected cell lysate may be used to amplify and prepare working stocks of recombinant HSV-1 viruses comprising gC fusion polypeptides.

Accordingly, purified recombinant HSV virions expressing heterologous genes, for example, recombinant HSV-1 virions, are used to infect host cells and recombinant HSV virions released from the host cells are then purified for use in the fabrication of the presently disclosed arrays as described elsewhere herein (e.g., for printing on FAST slides). The term "purified" does not require the material to be present in a form exhibiting absolute purity, exclusive of the presence of other compounds. Purification of starting material or natural material to at least about one order of magnitude, preferably two or three orders, and more preferably four or five orders of magnitude is expressly contemplated. As an example, purification from 0.1% concentration to 10% concentration is two orders of magnitude.

In one embodiment, the host cells are Vero cells, transformed Vero cell lines, or human foreskin fibroblast (HFT) cells. However, any host cell capable of propagation of HSV virions, for example, HSV-1 virions, may be used (e.g., brephic hamster kidney cells (BHK-21), human embryonic lung cells (HEL), human pharyngeal cancer epithelial cells (Hep-2), and the like).

Although recombinant HSV virions, for example, recombinant HSV-1 virions, may be preferred, other enveloped viruses may also be used within the recombinant virion array. As used herein, enveloped viruses have a viral envelope covering their protein capsids, and typically are comprised of phospholipids and proteins, including viral glycoproteins. In addition to HSV-1 and HSV-2, additional exemplary enveloped viruses for use within the recombinant virion array may include, but are not limited to, the following viral families and viruses: Retroviridae (i.e. Lentivirinae), such as human immunodeficiency virus (HIV); Flaviviridae, such as the Flaviviruses like Yellow fever virus (YFV) and Dengue virus, the Hepaciviruses like hepatitis C virus (HCV), and the Pestiviruses like Bovine viral diarrhea virus (BVDV); Varicella-zoster virus (VZV), Cytomegalovirus (CMV) or Human Herpes virus type 6 (HHV-6); Poxviridae, such as Vaccinia; Hepadnaviridae, such as hepatitis B virus (HBV); Coronaviridae, such as SARS-CoV; Orthomyxoviridae, such as influenza virus A, B and C; Togaviridae; Arenaviridae, such as Arenavirus; Bunyaviridae, such as Punta Toro; Paramyxoviridae, such as Respiratory syncytial virus (RSV) or Parainfluenza-3 virus; and Rhabdoviridae.

Substrate

The substrates of the arrays can comprise at least one surface on which a pattern of recombinant virion microspots can be present (i.e., a plurality of recombinant virion microspots stably associated with a surface of the substrate). In one embodiment, the substrate can be glass, for example, glass coated with nitrocellulose, for example, a nitrocellulose-coated slide (i.e., FAST slides).

In other embodiments, the substrate comprises a substance selected from the group consisting of a ceramic substance, a glass, a metal, a crystalline material, a plastic, a polymer or co-polymer, and combinations thereof. Such substrates include for example, but are not limited to, (semi) noble metals such as gold or silver; glass materials such as soda-lime glass, pyrex glass, vycor glass, quartz glass; metallic or non-metallic oxides; silicon, monoammonium phosphate, and other such crystalline materials; transition metals; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

The substrate may take a variety of configurations ranging from simple to complex, depending on the intended use of the array. Thus, the substrate could have an overall slide or plate configuration, such as a rectangular or disc configuration. A standard microplate configuration can be used. In certain embodiments, the substrate may have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.1 mm to 2 mm and more usually from about 0.2 to 1 mm.

In some embodiments, the surface may be smooth or substantially planar, or have irregularities, such as depressions or elevations. Further, the surface on which the pattern of microspots can be present may be modified with one or more different layers of compounds or coatings that serve to modify the properties of the surface in a desirable manner.

Accordingly, an array may further comprise a coating material on the whole or a portion of the surface of the substrate comprising the recombinant virion microspots. Preferably the coating material enhances the affinity of the recombinant virion microspot for the substrate.

In one embodiment, the coating material can be nitrocellulose. In other embodiments, the coating material can be a silane, thiol, disulfide, or a polymer. When the material can be a thiol, the substrate may comprise a gold-coated surface and/or the thiol comprises hydrophobic and hydrophilic moieties. When the coating material can be a silane, the substrate comprises glass and the silane may present terminal moieties including, for example, hydroxyl, carboxyl, phosphate, glycidoxy, sulfonate, isocyanato, thiol, or amino groups.

In an alternative embodiment, the coating material may be a derivatized monolayer or multilayer having covalently bonded linker moieties. The monolayer coating (e.g., comprising long chain hydrocarbon moieties) may have thiol (e.g., thioalkyl), disulfide or silane groups that produce a chemical or physicochemical bonding to the substrate. The attachment of the monolayer to the substrate may also be achieved by non-covalent interactions or by covalent reactions.

In one embodiment, the thiol can be a thioalkyl compound and is selected from the group consisting of a thioalkyl acid, thioalkyl alcohol, thioalkyl amine, and halogen containing thioalkyl compound. For example, the thioalkyl compound may be a thioalkyl acid, for example, 16-mercaptohexadecanoic acid.

After attachment to the substrate, the monolayer may comprise at least one reactive functional group. Examples of reactive functional groups on the monolayer coating include, but are not limited to, carboxyl, isocyanate, halogen, amine or hydroxyl groups. In one embodiment, these reactive functional groups on the monolayer coating may be activated by standard chemical techniques to corresponding activated functional groups on the monolayer coating (e.g., conversion of carboxyl groups to anhydrides or acid halides, etc.). The activated functional groups of the monolayer coating on the substrate may be, but not limited to, anhydrides, N-hydroxysuccinimide esters or other common activated esters or acid halides, for covalent coupling to terminal amino groups of the linker compound. In another embodiment, the activated functional groups on the monolayer coating may be, but not limited to, anhydride derivatives for coupling with a terminal hydroxyl group of the linker compound; hydrazine derivatives for coupling onto oxidized sugar residues of the linker compound; or maleimide derivatives for covalent attachment to thiol groups of the linker compound. To produce a derivatized monolayer coating, at least one terminal carboxyl group on the monolayer coating can be first activated to an anhydride group and then reacted with a linker compound. Alternatively, the reactive functional groups on the monolayer coating may be reacted with a linker compound having activated functional groups, for example, but not limited to, N-hydroxysuccinimide esters, acid halides, anhydrides, and isocyonates for covalent coupling to reactive amino groups on the monolayer coating.

In one embodiment, the linker compound has one terminal functional group, a spacer region and a membrane bound protein adhering region. The terminal functional groups for reacting with the activated functional groups on the activated monolayer coating are for example, but not limited to, halogen, amino, hydroxyl, or thiol groups. In certain embodiments, the terminal functional group is selected from the group consisting of a carboxylic acid, halogen, amine, thiol, alkene, acrylate, anhydride, ester, acid halide, isocyanate, hydrazine, maleimide and hydroxyl group.

The spacer region may include, but is not limited to, oligo/poly ethers, oligo/poly peptides, oligo/poly amides, oligo/poly amines, oligo/poly esters, oligo/poly saccharides, polyols, multiple charged species or any other combinations thereof. Examples include, but are not limited to, oligomers of ethylene glycols, peptides, glycerol, ethanolamine, serine, inositol, etc., and are such that membrane bound proteins freely adhere to the adhering region of the linker moiety. The spacer region may be hydrophilic in nature. In one embodiment, the spacer has n oxyethylene groups, where n can be between 2 and 25. In other embodiments the membrane adhering region or “hydrophobic tail” of the linker compound can be hydrophobic or amphiphilic with straight or branched chain alkyl, alkynyl, alkenyl, aryl, araalkyl, heteroalkyl, heteroalkynyl, heteroalkenyl, heteroaryl, or heteroarylalkyl. In another embodiment, the membrane bound protein adhering region comprises a $C_{10}$ to $C_{25}$ straight or branched chain alkyl or heteroalkyl hydrophobic tail. In the most preferred embodiment, the hydrophobic tail comprises a $C_{10}$ to $C_{20}$ straight or branched chain alkyl fragment.

In another embodiment, the linker compound has a terminal functional group on one end, a spacer, a linker/membrane bound protein adhering region and a hydrophilic group on another end. The hydrophilic group at one end of the linker compound may be a single group or a straight or branched chain of multiple hydrophilic groups, including but not limited to, a single hydroxyl group or a chain of multiple ethylene glycol units.

In some embodiments the present invention provides an array (or microarray) comprising a library of membrane bound protein antibodies and a substrate. In some embodiments the present invention provides an array (or microarray) comprising a library of virions expressing or containing membrane bound proteins and a substrate. In some embodiments, at least one or each membrane bound protein antibody or virion can be immobilized on a substrate. The membrane bound protein antibody or virion may be reversibly or irreversibly immobilized on the substrate. The substrate can be planar or a particle and can comprise a solid or porous material. The substrate may be either organic or inorganic, biological or non-biological, or any combination of these materials.

In one embodiment, the substrate can be transparent or translucent. The portion of the surface of the substrate on which the patches reside can be preferably flat and firm or semi-firm. Numerous materials are suitable for use as a substrate. The substrate can comprise silicon, silica, glass, or a polymer. For instance, the substrate can comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum, copper, titanium, and their alloys are also options for substrates of the array. In addition, many ceramics and polymers may also be used as substrates. Polymers which may be used as substrates include, but are not limited to, the following: polystyrene; poly(tetra)fluorethylene; (poly)vinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LIGA structures may also serve as substrates in the present invention.

In one embodiment, a microarray of distinct antibodies or virions can be bound on a glass slide coated with a polycationic polymer. A substrate can be formed according to another aspect of the invention, and intended for use in detecting binding of a target transmembrane molecule to one or more distinct membrane bound protein antibodies. In one embodiment, the substrate includes a glass substrate having formed on its surface, a coating of a polycationic polymer, preferably a cationic polypeptide, such as poly-lysine or poly-arginine. Formed on the polycationic coating can be a microarray of distinct biopolymers, each localized at known selected array regions, such as regions.

The slide may be coated by placing a uniform-thickness film of a polycationic polymer, e.g., poly-1-lysine, on the surface of a slide and drying the film to form a dried coating. The amount of polycationic polymer added can be sufficient to form at least a monolayer of polymers on the glass surface. The polymer film can be bound to surface via electrostatic binding between negative silyl-OH groups on the surface and charged amine groups in the polymers. Poly-1-lysine coated glass slides may be obtained commercially, e.g., from Sigma Chemical Co. (St. Louis, Mo.).

A suitable microarray substrate can be also made through chemical derivatization of glass. Silane compounds with appropriate leaving groups on a terminal Si will covalently bond to glass surfaces. A derivatization molecule can be designed to confer the desired chemistry to the surface of the glass substrate. An example of such a bifunctional reagent can be amino-propyl-tri(ethoxy)silane, which reacts with glass surfaces at the tri(ethoxy)silane portion of the molecule while leaving the amino portion of the molecule free. Surfaces having terminal amino groups are suitable for adsorption of biopolymers in the same manner as poly-lysine coated slides. The identity of the terminal surface group can be modified by further chemical reaction. For example, reaction of the terminal amine in the above example with glutaraldehyde results in a terminal aldehyde group. Further layers of modification may be applied to achieve the desired reactivity before spotting the microarray, such as by application of a Protein A or Protein G solution to the silynated glass. Additional surfaces that bind virions and/or polypeptides are nitrocellulose-coated glass slides, available commercially from Schleicher and Schuell, and virion/protein-binding plastics such as polystyrene.

The spotted antibodies or virions may be attached by either non-covalent bonding, or covalent bonding. Adsorption occurs through electrostatic, hydrophobic, Van der Waals, or hydrogen-bonding interactions between the spotted polypeptide and the array substrate. Simple application of the polypeptide or virion solution to the surface in an aqueous environment can be sufficient to adsorb the polypeptide or virion. Covalent attachment can be achieved by reaction of functional groups on the polypeptide or virion with a chemically activated surface. For example, if the surface has been activated with a highly reactive electrophilic group such as an aldehyde or succinimide group, unmodified polypeptides or polypeptides of virions react at amine groups, as at lysine residues or the terminal amine, to form a covalent bond.

When covalent surfaces are used, such as expoy- and aldehyde-grafted surfaces, a virion can be covalently cross-linked to the surface via primary amines (e.g., lysine residues) of the surface glycoproteins. When a nitrocellulose-coated surface (e.g., FAST slide) can be used, virions can be absorbed or adopted to the porous surface. HSV-1 virions can adsorb efficiently to any plastic or coated surface.

In some embodiments, covalent surface attachments may be useful for binding under stringent conditions. In some embodiments, covalent surface attachments may be more useful than non-covalent surface attachments for binding under stringent conditions. In some embodiments, a reduced amount of virions are covalently immobilized per spot on an array compared to the amount of virions non-covalently immobilized per spot on an array. In some embodiments, an increased amount of virions are non-covalently immobilized per spot on an array compared to the amount of virions covalently immobilized per spot on an array. In some embodiments, covalent surfaces can be used to maintain low background signals (e.g., Cy3 and other channels with shorter wavelength). In some embodiments, covalent surface attachments are employed for certain types of assays, such as phosphorylation. In some embodiments, non-covalent surfaces, such as FAST slide, can absorb more virions per spot than the number of virions absorbed per spot on a covalent surface. In some embodiments, non-covalent surfaces are better surfaces for detecting binding events of low affinity than covalent surfaces.

To form the microarray, defined volumes of distinct biopolymers are deposited on the polymer-coated slide using any suitable method known in the art. According to an important feature of the substrate, the deposited antibodies or virions remain bound to the coated slide surface non-covalently when an aqueous sample can be applied to the substrate under conditions that allow binding of labeled ligands in the sample to cognate binding partners in the substrate array.

In some embodiments, at least one or each microarray contains at least about 50, 60, 70, 80, 90, 100, 150, 200, 250, 300, 350, 400, 450, 500, 600, 700, 800, 900, or 1000 distinct antibodies per surface area of less than about 1 $cm^2$. In some embodiments, at least one or each microarray contains at least about 50, 60, 70, 80, 90, 100, 150, 200, 250, 300, 350, 400, 450, 500, 600, 700, 800, 900, or 1000 distinct virions per surface area of less than about 1 $cm^2$. In one embodiment, the microarray contains 50, 60, 70, 80, 90, 100, 150, 200, 250, 300, 350 or 400 regions in an area of about 16 $mm^2$, or $2.5 \times 10^3$ regions/$cm^2$. Also in a preferred embodiment, the antibodies in at least one or each microarray region are present in a defined amount between about 0.1 femtomoles and 100 nanomoles. Also in a preferred embodiment, the virions in at least one or each microarray region are present in a defined amount between about 0.1 femtomoles and 100 nanomoles.

Also in a preferred embodiment, the biopolymers have lengths of at least about about 50 units, e.g. amino acids, nucleotides, etc., i.e., substantially longer than polymers which can be formed in high-density arrays by various in situ synthesis schemes.

Fabrication Methods

The presently disclosed subject matter also relates, at least in part, to methods of fabricating arrays comprising a plurality of recombinant virion microspots stably associated with a surface of a substrate as disclosed herein. The arrays may be prepared using micro-patterning techniques well known in the art. Such techniques may include, for example, microstamping (U.S. Pat. No. 5,731,152), microcontact printing using PDMS stamps (Hovis et al. (2000) *Langmuir* 16:894-897), capillary dispensing devices (U.S. Pat. No. 5,807,522), and micropipetting devices (U.S. Pat. No. 5,601,980).

In one embodiment, the tip of a probe (also referred to as a "pin") can be immersed into a solution of recombinant virions. The tip can be removed from the solution to provide solution comprising recombinant virions adhered to the tip. The solution comprising recombinant virions can be contacted with the surface of a substrate to thereby transfer the solution comprising recombinant virions from the tip to the surface of the substrate.

A "pin" as used in the presently disclosed subject matter may be of any shape, size, and dimension. For example, the pin printing process may involve ring shaped pins, square pins, or point pins, and the like. In another embodiment, direct contact printing may involve single pinprinting or multiple pin printing (i.e., a single pin printing method involving a source plate or multiple pin-printing using a laid out array of multiple pins patterned in any format).

The printing apparatus may include a print head, plate, substrate handling unit, XY or XYZ positioning stage, environmental control, instrument control software, sample tracking software, etc. Such an apparatus includes, for example, a quill pin-printer sold by Cartesian Technologies, Inc.

For a high-density array, a typographical recombinant virion microspot array having a matrix of recombinant virion microspots comprising a plurality of recombinant virions may be used to align and fit at least one or each recombinant virion microspot from the matrix into a corresponding source well (e.g., a well of a microtiter plate).

II. Methods of Use

The presently disclosed subject matter also relates to methods of use for an array comprising a plurality of recombinant virion microspots stably associated with a surface of a substrate, wherein the recombinant virion microspots comprise a plurality of recombinant virions, wherein the recombinant virions comprise envelopes comprising a plurality of heterologous membrane bound proteins, for example, human membrane bound proteins that retain their native conformations and/or interactions. These methods of use include, but are not limited to, high-content, high-throughput assays for screening for ligands and/or drugs that bind membrane bound proteins, for example, human membrane bound proteins. Additional methods of use include medical diagnostic, proteomic, and biosensor assays.

For use within the methods, a sample can be typically delivered to the array, and the sample can be typically a fluid sample, for example, a solution comprising proteins, polypeptides, fragments thereof, or any other analyte (or "target") of interest to be bound by the heterologous membrane bound proteins in the recombinant virion microspots of the array. In certain embodiments, the sample may comprise a biological sample, as described further below.

The assays used with the arrays may be direct, noncompetitive assays or indirect, competitive assays. In the noncompetitive method, the affinity for binding sites on the heterologous membrane bound proteins in the recombinant virion microspots can be determined directly. In this method, the heterologous membrane bound proteins in the recombinant virion microspots are directly exposed to an analyte (or "target"). The analyte may be labeled or unlabeled. If the analyte can be labeled, the methods of detection could include fluorescence, luminescence, radioactivity, and the like. If the analyte is unlabeled, the detection of binding would be based on a change in some physical property at the surface of the heterologous membrane bound proteins in the recombinant virion microspots. Such physical properties could include, for example, a refractive index or electrical impedance. The detection of binding of unlabeled targets could include, for example, mass spectroscopy. In the competitive method, binding-site occupancy may be determined indirectly. In this method, the heterologous membrane bound proteins in the recombinant virion microspots of the array are exposed to a solution containing a cognate labeled target or ligand for the heterologous membrane bound proteins in the recombinant virion microspots of the array and an unlabeled target. The labeled cognate ligand and the unlabeled target compete for the binding sites on the heterologous membrane bound proteins in the recombinant virion microspots of the array. The affinity of the target for the heterologous membrane bound proteins in the recombinant virion microspots relative to the cognate ligand can be determined by the decrease in the amount of binding of the labeled ligand. The detection of binding of the target can also be carried out using sandwich assays, in which after the initial binding, the array can be incubated with a second solution containing molecules such as labeled antibodies that have an affinity for the bound target, and the amount of binding of the target can be determined based on the amount of binding of the labeled antibodies to the heterologous membrane bound proteins-target complex. The detection of binding of the target can be carried out using a displacement assay in which after the initial binding of labeled ligand, the array can be incubated with a second solution containing compounds of interest. The binding capability and the amount of binding of the target are determined based on the decrease in number of the pre-bound labeled ligands in the heterologous membrane bound proteins in the recombinant virion microspots of the array.

In one embodiment, the arrays may be used in a method for screening for ligands and/or drugs when a potential ligand and/or drug candidate can be screened directly for its ability to bind or otherwise interact with the plurality of heterologous membrane bound proteins on the array. Alternatively, a plurality of potential ligand and/or drug candidates may be screened in parallel for their ability to bind or otherwise interact with one or more types of heterologous membrane bound proteins on the array. The ligand and/or drug screening process may optionally involve assaying for the interaction, such as binding, of at least one analyte or component of a sample with one or more heterologous membrane bound proteins on the array, both in the presence and absence of the potential ligand and/or drug candidate. This allows for the potential ligand and/or drug candidate to be tested for its ability to act as an inhibitor of the interaction or interactions originally being assayed.

In another embodiment, the arrays may be used in a method for screening a plurality of proteins for their ability to bind a particular component of a target sample. This method comprises delivering the sample to an array comprising the heterologous membrane bound proteins in the recombinant virion microspots and detecting, either directly or indirectly, for the presence or amount of the particular component retained at at least one or each microspot. In a preferred embodiment, the method further comprises the intermediate step of washing the array to remove any unbound or nonspecifically bound components of the sample from the array before the detection step. In another embodiment, the method further comprises the additional step of further characterizing the particular component retained on at least one microspot.

In another embodiment, a method of assaying for protein-protein binding interactions is provided which comprises the following steps: first, delivering a sample comprising at least one protein to be assayed for binding to the recombinant virion array; and then detecting, either directly, or indirectly, for the presence or amount of the protein from the sample that can be retained at at least one or each microspot.

Another embodiment provides a method of assaying in parallel for the presence of a plurality of analytes in a sample which can react with one or more of the heterologous membrane bound proteins on the recombinant virion array. This method comprises delivering the sample to the array and detecting the interaction of the analyte with the heterologous membrane bound proteins at at least one or each recombinant virion microspot.

In yet another embodiment, a method of assaying in parallel for the presence of a plurality of analytes in a sample which can bind one or more of the heterologous membrane bound proteins on the recombinant virion array comprises delivering the fluid sample to the array and detecting, either directly or indirectly, for the presence or amount of analyte retained at at least one or each microspot. In a preferred embodiment, the method further comprises the step of washing the array to remove any unbound or non-specifically bound components of the sample from the array.

In another embodiment, the recombinant virion array may be used in a diagnostic manner when the plurality of analytes being assayed can be indicative of a disease condition or the presence of a pathogen in an organism. In such embodiments, the sample which can be delivered to the array will then typically comprise a biological sample. As used herein, the phrase "biological sample" encompasses a variety of sample types obtained from a subject and useful in the procedure. In one embodiment, the biological sample comprises whole blood, hemocytes, serum, or plasma. Where biological samples include solid tissue samples, liquid samples may be derived from the solid tissue by various means known in the art, including homogenization, digestion and/or extraction. Accordingly, biological tissue samples may comprise solid tissue samples, liquid tissue samples, biological fluids, aspirates, cells and cell fragments. Specific examples of biological samples include, but are not limited to, solid tissue samples obtained by surgical removal, pathology specimens, archived samples, or biopsy specimens, tissue cultures or cells derived therefrom and the progeny thereof, and sections or smears prepared from any of these sources. Non-limiting examples of biological samples include samples obtained from breast tissue, lymph nodes, and breast tumors. Biological samples also include any material derived from the body of a vertebrate animal, including, but not limited to, blood, cerebrospinal fluid, serum, plasma, urine, nipple aspirate, fine needle aspirate, tissue lavage such as ductal lavage, saliva, sputum, ascites fluid, liver, kidney, breast, bone, bone marrow, testes, brain, ovary, skin, lung, prostate, thyroid, pancreas, cervix, stomach, intestine, colorectal, brain, bladder, colon, nares, uterine, semen, lymph, vaginal pool, synovial fluid, spinal fluid, head and neck, nasopharynx tumors, amniotic fluid, breast milk, pulmonary sputum or surfactant, urine, fecal matter and other liquid samples of biologic origin.

A subject diagnosed by the presently disclosed methods in their many embodiments can be desirably a human subject, although it is to be understood that the methods described herein are effective with respect to all vertebrate species, which are intended to be included in the term "subject." Accordingly, a "subject" can include a human subject for medical purposes, such as for the diagnosis or treatment of an existing disease, disorder, condition or the prophylactic diagnosis or treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject can be a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

In general, delivery of samples wherein the samples comprise solutions containing proteins to be bound by the heterologous membrane bound proteins in the recombinant virion microspots of the array may optionally be preceded, followed, or accompanied by delivery of a blocking solution. A blocking solution contains protein or another moiety which will adhere to sites of non-specific binding on the array. For example, solutions of bovine serum albumin, milk powder, polyglutamic acid, DNA molecules or lectins may be used as blocking agents.

A range of detection methods are applicable to the methods. Detection may be either quantitative, semiquantitative, or qualitative. The presently disclosed array may be interfaced with optical detection methods such as absorption in the visible or infrared range, chemiluminescence, and fluorescence (including lifetime, polarization, fluorescence correlation spectroscopy (FCS), and fluorescence-resonance energy transfer (FRET)). Furthermore, other modes of detection such as those based on optical waveguides (PCT Publication WO96/26432 and U.S. Pat. No. 5,677,196), surface plasmon resonance, surface charge sensors, and surface force sensors are compatible with many embodiments.

In another embodiment, the presently disclosed subject matter is directed to methods of detecting antibodies that specifically bind heterologous membrane bound proteins in the recombinant virion microspots of the array. The term "specifically binds," refers to a molecule or compound that binds to a target (e.g., a protein) with at least about five-fold greater affinity as compared to any non-targets, e.g., at least about 10-, 20-, 50-, or 100-fold greater affinity. The recombinant virion array may be used to select antibodies from libraries of soluble antibodies or from phage-display or ribosome-display libraries. The recombinant virion array may also be used to analyze antibodies in small amounts of patient sera, as during infections or in autoimmune conditions.

As used herein, the term "antibody" refers to a polypeptide or group of polypeptides which are comprised of at least one binding domain, where an antibody binding domain can be formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments. As used herein, an "antigenic determinant" can be the portion of an antigen molecule, in this case a heterologous membrane bound polypeptide that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least about 6 such amino acids, and more usually at least about 8-10 such amino acids. Methods for determining the amino acids which make up an epitope include x-ray crystallography, 2-dimensional nuclear magnetic resonance, and epitope mapping (e.g. the Pepscan method described by H. Mario Geysen et al. (1984) *Proc. Natl. Acad. Sci. U.S.A.* 81:3998-4002; PCT Patent Pub. No. WO 84/03564; and PCT Patent Pub. No. WO 84/03506.

Antibodies and Antibody Libraries to Membrane Proteins

The present invention also relates to libraries of antibodies to membrane proteins, including methods and systems to produce, generate, characterize, and utilize antibodies. The antibodies can be highly specific to membrane proteins. The library can comprise of a plurality of different antibodies to membrane proteins, where the antibodies are produced by the same platform. The library can comprise plurality of different antibodies, wherein within the plurality or a subset of the plurality, each antibody can be a monospecific antibody to a membrane protein; binds a native form of its target membrane protein; can be a monoclonal antibody to a membrane protein; can be a membrane protein immunoprecipitating antibody; can be an IgG antibody to a membrane protein or antibody of IgG isotype antibody to a membrane protein; has a binding affinity for its target membrane protein that can be similar to that of another antibody of the plurality of antibodies, have a binding affinity of at least $10^{-7}$M ($K_D$) for its target membrane protein; or any combination thereof.

Platform

The library of antibodies can comprise a plurality of different antibodies to membrane proteins produced by the same platform. In one embodiment, the library of antibodies comprises a plurality of different antibodies to membrane proteins wherein at least about 10% of the plurality can be produced by the same platform. For example, the library can comprise a plurality of different antibodies to membrane proteins wherein at least about 20%, 30%, 40%, 50%, 60%, 70%, 80%, 90%, 95%, 99% or 100% of the plurality are antibodies to membrane proteins produced by the same platform.

Antibodies are considered to be produced by the same platform when a first antibody and second antibody can be produced from the same protocol. For example, the plurality of antibodies to membrane proteins can be produced by the platform. In one embodiment, an animal can be immunized with a plurality of virions expressing different membrane proteins as described herein. The animal can be a non-human animal, such as a bovine, avian, canine, equine, feline, ovine, porcine, or primate animal. The animal can be a mammal, such as a mouse, rat, rabbit, cat, dog monkey, or goat.

The plurality of virions expressing different membrane proteins can comprise isolated or non-isolated virions or fragments thereof, such as isolated virions expressing or containing one or more heterologous membrane bound proteins. In another embodiment, the plurality of virions can comprise non-isolated virions.

The plurality of virions can comprise a biological sample. For example, the plurality of virions can comprise a single virion or multiple virions produced by the methods described herein or from an organism or cell. The organism or cell can be a human or non-human. The non-human organism or cell can be a mammal or mammalian, such as a mouse, rat, rabbit, cat, dog, monkey, or goat. The biological sample can be a tissue, blood, sera, plasma, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool water, pancreatic juice, lavage fluid from sinus cavities, bronchopulmonary aspirate, blastocyl cavity fluid, or umbilical cord blood containing a virion. In one embodiment, the biological sample can be substantially depleted of a common serum protein, such as, but not limited to, albumin or IgG. Depletion can comprise filtration, fractionation, or affinity purification.

The biological sample can comprise a virion or a virus containing a heterologous membrane protein, such as a enveloped virus, for example, an immunodeficiency virus such as human immunodeficiency virus (HIV), a T lymphotrophic virus such as human T lymphotrophic virus (HTLV), simian immunodeficiency virus (SIV), a herpesvirus such as a herpes simplex virus (HSV), a measles virus, a papillomavirus (HPV), an adenovirus, a vaccinia virus, Retroviridae (e.g. human immunodeficiency viruses, such as HIV-1 (also referred to as HTLV-III, LAV or HTLV-III/LAV, or HIV-III); and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae; and unclassified viruses (e.g. the etiological agents of Spongiform encephalopathies, the agent of delta hepatitis; Norwalk and related viruses, astroviruses, or an influenza virus.

In a preferred embodiment, HSV-1 can be utilized to produce the recombinant virions described herein. However, other herpesviruses can also be used. HSV-1 does not normally go through latency when transfected into a host cell, making it convenient for virion production. The genetics of HSV-1 are superior to other viruses for engineering human genes. Other systems, such as those based on Baculovirus and retroviruses, have drawbacks which include, nonideal virion structure for making arrays (HSV-1 produces a spherical virion ideal for printing), incorrect post-translational modifications, lower efficiency or inability to incorporate host derived membrane proteins and lower numbers of incorporated molecules.

The number of human genes coding for a membrane protein with predicted alpha-helical transmembrane region(s) is estimated to be around 5,600, corresponding to approximately 26% of the human protein-coding genes. The largest fraction of these proteins has only one predicted transmembrane region, but there are also many proteins with seven predicted transmembrane regions, including the G-protein coupled receptors. The plurality of virions can comprise a plurality of membrane bound proteins with a transmembrane domain. For example, the transmembrane proteins can comprise at least about 100, membrane bound proteins with a transmembrane domain, such as at least about 200, 300, 400, 500, 600, 700, 800, 900, 1,000, 2,000, 3,000, 4,000, 5,000, 5,500, 5,600, or more different membrane bound proteins with a transmembrane domain.

A library of virions can comprise a plurality of membrane bound proteins with a transmembrane domain. For example, a library of virions can comprise at least about 100, membrane bound proteins with a transmembrane domain, such as at least about 200, 300, 400, 500, 600, 700, 800, 900, 1,000, 2,000, 3,000, 4,000, 5,000, 5,500, 5,600, or more different membrane bound proteins with a transmembrane domain. The library of virions can represent at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or 60% of an organism's proteome. The library of virions can represent at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or 60%, 70%, 80%, 90%, or 100% of an organism's membrane bound proteome. The library of virions can comprise a plurality of membrane bound proteins that represent a substantial portion or an entire organism's membrane bound proteome, such as a bacterial, viral, or fungal, proteome. The library of virions can comprise a plurality of membrane bound proteins that represent a substantial portion or an entire proteome of an insect or mammal, such as a mouse, rat, rabbit, cat, dog, monkey, goat, or human. The library or plurality of membrane bound proteins that can also comprise a fusion protein library that represents an organism's membrane bound proteome in unpurified form, such as a collection of overexpressing virions.

Probing can be performed by arraying the virions overexpressing or containing the heterologous membrane bound proteins, such as a fusion protein, and testing antibodies or hybridoma supernatants against the arrayed virions. Probing can also be performed by fluorescence flow cytometry and the membrane bound protein target identified by PCR or sequence analysis of recombinant DNA in the virion.

Antibodies can be selected and selected antibodies can be highly specific monoclonal antibodies that recognize only one transmembrane target and do not cross react with the other transmembrane or non-membrane protein targets in the proteome library of that organism. Cell lines produced that secrete these monoclonal antibodies can be expanded. The membrane bound protein antibodies produced by the same platform or protocol can be used to produce or form a library of membrane bound protein antibodies.

Membrane bound protein antibodies can also be produced by the same platform when the antibodies are produced by the same method or protocol, such as described further below, in methods of producing a library.

Monospecificity

The library of membrane bound protein antibodies can comprise a plurality of different membrane bound protein antibodies, at least one or each antibody having a particular binding specificity for its membrane bound protein target. For example, the library of membrane bound protein antibodies can comprise a plurality of different membrane bound protein antibodies, wherein the membrane bound protein antibodies are monospecific. In one embodiment, the library of membrane bound protein antibodies comprises a plurality of different membrane bound protein antibodies wherein at least about 10%, 20%, 30%, 40%, 50%, 60%, 70%, 80%, 90%, 95%, 99% or 100% of the plurality of membrane bound protein antibodies can be monospecific.

A membrane bound protein antibody can be monospecific if the membrane bound protein antibody has an A value of greater than 6 and an S value of greater than 3 for a membrane bound protein when incubated on array comprising a plurality of membrane bound proteins. A membrane bound protein antibody can be monospecific if the membrane bound protein antibody has an A value of greater than 6 and an S value of greater than 3 for a membrane bound protein when incubated on array comprising a plurality of non-membrane bound proteins. A membrane bound protein antibody can be monospecific if the membrane bound protein antibody has an A value of greater than 6 and an S value of greater than 3 for a membrane bound protein when incubated on array comprising a plurality of transmembrane and non-membrane bound proteins. The number of standard deviations above mean signal intensity across the entire array for a membrane bound protein antibody can be a value termed A. The difference between the top signal and the second-highest signal on the array when the signal intensities are rank ordered for the membrane bound protein antibody against the entire array can be the S value. For example, the A and S value can be calculated by combining individual supernatants from membrane bound protein antibody-producing cells or hybridomas into sets of 12×12 two-dimensional pools, and these pools are incubated on an array (such as a human membrane bound proteome microarray), and the membrane bound protein antibodies are labeled (such as by a Cy5-coupled anti-IgG secondary antibody, or any other method of detecting an antibody). Following washing and scanning, the signal intensity for at least one or each spot (representing membrane bound protein antibody binding to a protein or antigen on the array) as the ratio of foreground to background signal. The number of standard deviations above mean signal intensity across the entire array can be a value termed A. Duplicate spots (for each duplicate pair of proteins or antigens) for which A>3 are flagged and results deconvoluted to identify proteins or antigens that are present at the intersection of a single horizontal and single vertical pool, and thus recognized by an individual monoclonal antibody. Each candidate highly specific monoclonal membrane bound protein antibody (i.e. A>3) can be tested individually against the entire array, and A measured for each spotted protein. The signal intensities are then rank ordered and the difference between the top signal and the second-highest signal on the array can be calculated, giving the S value. Membrane bound protein monoclonal antibodies in which A>6 and S>3 are identified as monospecific membrane bound protein monoclonal antibodies (mMAbs). Dispecific membrane bound protein monoclonal antibodies (dMAbs) bind intensely to two different proteins on the array and have A>6 and S<3.

In some embodiments, the membrane bound protein mMAbs can have an A value of greater than 6, 7, 8, 9, 10, 20, 30, 40, 50, 60, 70, 80, 90, or 100 and/or an S value of greater than 3, 4, 5, 6, 7, 8, 9, 10, 20, 30, 40, 50, 60, 70, 80, 90, or 100.

In one embodiment, the array for determining the monospecificity of a membrane bound protein antibody comprises an organism's proteome library, such as at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's proteome. In one embodiment, the array for determining the monospecificity of a membrane bound protein antibody comprises an organism's membrane bound proteome library, such as at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's transmembrane proteome. The library of antigens can represent a substantial portion or an entire organism's proteome or transmembrane proteome, such as a bacterial, viral, fungal proteome. The library of antigens can represent a substantial portion or an entire proteome or transmembrane proteome of an insect or mammal, such as a mouse, rat, rabbit, cat, dog, monkey, goat, or human. For example, an organism's proteome library can comprise at least about 11,000, 12,000, 13,000, 14,000, 15,000, 16,000, 17,000, 18,000, 19,000, or 20,000 different antigens. For example, an organism's membrane bound proteome library can comprise at least about at least about 100, 200, 300, 400, 500, 600, 700, 800, 900, 1,000, 2,000, 3,000, 4,000, 5,000, 5,500, 5,600, or more different membrane proteins with a transmembrane domain.

Binding Affinity

The library of membrane bound protein antibodies can comprise a plurality of different membrane bound protein antibodies have a particular binding affinity its membrane bound protein target. For example, the library can comprise a plurality of different membrane bound protein antibodies wherein at least about 10%, 20%, 30%, 40%, 50%, 60%, 70%, 80%, 90%, 95%, 99% or 100% of the plurality has a particular binding affinity. For example, the plurality of membrane bound protein antibodies can have a binding affinity as determined by its dissociation constant ($K_D$), of at least about $10^{-7}$M, such as at least about $10^{-8}$M, $10^{-9}$M, $10^{-10}$M, $10^{-11}$M, $10^{-12}$M, $10^{-13}$M, $10^{-14}$M, $10^{-15}$M, or $10^{-16}$M, for its target membrane bound protein.

The plurality of membrane bound protein antibodies can have a binding affinity as measured by its association rate constant ($k_{on}$), wherein the plurality of antibodies have a binding affinity of at least about $10^4$ $M^{-1}s^{-1}$, at least about $5\times10^4$ $M^{-1}s^{-1}$, at least about $10^5$ $M^{-1}s^{-1}$, at least about $5\times10^5$ $M^{-1}s^{-1}$, at least about $10^6$ $M^{-1}s^{-1}$, at least about $5\times10^6$ $M^{-1}s^{-1}$, at least about $10^7$ $M^{-1}s^{-1}$, at least about $5\times10^7$ $M^{-1}s^{-1}$, or at least about $10^8$ $M^{-1}s^{-1}$. The plurality of antibodies can have a binding affinity as measured by its dissociation rate constant ($k_{off}$), wherein the plurality of antibodies have a binding affinity of less than $10^3$ M-1s-1, less than $5\times10^3$ M-1s-1, less than $10^4$ M-1s-1, less than $5\times10^4$ $M^{-1}s^{-1}$, less than $10^5$ $M^{-1}s^{-1}$, less than $5\times10^5$ $M^{-1}s^{-1}$, less than $10^6$ $M^{-1}s^{-1}$, less than $5\times10^6$ $M^{-1}s^{-1}$, less than $10^7$ $M^{-1}s^{-1}$, less than $5\times10^7$ $M^{-1}s^{-1}$, or less than $10^8$ $M^{-1}s^{-1}$, less than $5\times10^7$ $M^{-1}s^{-1}$, less than $10^8$ $M^{-1}s^{-1}$, less than $5\times10^8$ $M^{-1}s^{-1}$, less than $10^9$ $M^{-1}s^{-1}$, less than $5\times10^9$ $M^{-1}s^{-1}$, or less than $10^{10}$ $M^{-1}s^{-1}$.

The binding affinity can be determined by surface plasmon resonance, chromatography or any other methods known in the art. Binding affinity can also be determined by optically, such as by using real-time and/or label-free methods of detecting biomolecule interactions. In one embodiment, oblique-incidence reflectivity different (OIRD) can be used.

The library of membrane bound protein antibodies can comprise a plurality of different membrane bound protein antibodies that binds native form of its target membrane bound protein. For example, the library can comprise a plurality of different membrane bound protein antibodies wherein at least about 10%, 20%, 30%, 40%, 50%, 60%, 70%, 80%, 90%, 95%, 99% or 100% of the plurality binds a native form of its target membrane bound protein. In one embodiment, the plurality of membrane bound protein antibodies that binds a native form of its target membrane bound protein does not bind a denatured form of its target membrane bound protein under the same binding conditions.

The library of membrane bound protein antibodies can comprise a plurality of different membrane bound protein antibodies, wherein one or more antibodies of the library have a binding affinity for its target membrane bound protein that can be similar to the binding affinity of another membrane bound protein antibody of the plurality. For example, the library of membrane bound protein antibodies can comprise a first membrane bound protein antibody and a second membrane bound protein antibody, wherein the first membrane bound protein antibody has a binding affinity for a first membrane bound protein that similar to the binding affinity of the second membrane bound protein antibody to a second membrane bound protein. One membrane bound protein antibody of the library can have a binding affinity for its target membrane bound protein that can be within at least about 1%, 2%, 3%, 4%, 5%, 6%, 7%, 8%, 9%, 10%, 11%, 12%, 13%, 14%, 15%, 16%, 17%, 18%, 19%, or 20% of the binding affinity of one or more other membrane bound protein antibodies of the library. The first membrane bound protein antibody of the library can have a binding affinity for its target membrane bound protein that can be within at least about 20% of the binding affinity of one or more other membrane bound protein antibodies of the library. In one embodiment, the library of membrane bound protein antibodies can comprise a plurality of different membrane bound protein antibodies, wherein at least about 10%, 20%, 30%, 40%, 50%, 60%, 70%, 80%, 90%, 95%, 99% or 100% of the different membrane bound protein antibodies have a binding affinity for its target membrane bound proteins that can be within at least about 20% of the binding affinity of the rest of the plurality of different membrane bound protein antibodies to their respective target membrane bound protein.

Proteome

Also provided herein is a library of membrane bound protein antibodies can comprise a plurality of different antibodies that binds a portion of an organism's membrane bound proteome. The plurality of different membrane bound protein antibodies can bind at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's membrane bound proteome. For example, the plurality of different membrane bound protein antibodies can bind at least about 100, 200, 300, 400, 500, 600, 700, 800, 900, 1,000, 2,000, 3,000, 4,000, 5,000, 5,500, 5,600, or more membrane bound proteins of an organism. The membrane bound proteome can be a bacterial, viral, fungal proteome. The membrane bound proteome can be of an insect or mammal, such as a mouse, rat, rabbit, cat, dog, monkey, goat, or human. In some embodiments, the membrane bound proteome can be a human membrane bound proteome.

For example, the plurality of different membrane bound protein antibodies can bind at least about 0.5% of the human membrane bound proteome. In one embodiment, the plurality of different membrane bound protein antibodies can bind at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human membrane bound proteome.

Other Antibody Characteristics

The library of membrane bound protein antibodies can also comprise a plurality of different membrane bound protein antibodies, wherein the membrane bound protein antibodies are IgG antibodies (e.g. membrane bound protein antibodies of IgG isotype). For example, a library of membrane bound protein antibodies can comprise a plurality of different membrane bound protein antibodies, wherein at least about 10%, 20%, 30%, 40%, 50%, 60%, 70%, 80%, 90%, 95%, 99% or 100% of the membrane bound protein antibodies can be an IgG membrane bound protein antibody or membrane bound protein antibody of IgG isotype.

The library of membrane bound protein antibodies can also comprise a plurality of different membrane bound protein antibodies, wherein the membrane bound protein antibodies are immunoprecipitating membrane bound protein antibodies. For example, a library of membrane bound protein antibodies can comprise a plurality of different membrane bound protein antibodies, wherein at least about 10%, 20%, 30%, 40%, 50%, 60%, 70%, 80%, 90%, 95%, 99% or 100% of the antibodies can be a membrane bound protein immunoprecipitating antibody. An immunoprecipitating membrane bound protein membrane bound protein antibody can be a membrane bound protein antibody that can immunoprecipitate a target membrane bound protein from a cell homogenate as compared to a no antibody negative control and an anti-V5 antibody positive control. Detection of the immunoprecipitated target membrane bound protein can be by Western blot. The immunoprecipitation can be carried out with cleared cell lysate and approximately 2 μg of membrane bound protein antibody, followed by incubation for 2 hours at 4° C., then addition of a substrate to bind any membrane bound protein antibody-protein complex (such as protein-G Dynabead), and then incubation for an additional 2 hours at 4° C. After incubation the substrate can be washed, such as with ice cold TBST twice, the substrate transferred to a new reaction vessel, washed again with ice cold TBST, before being subjected to SDS-PAGE and Western blot analysis.

Membrane Bound Protein Classes

In one aspect, the present invention relates to a library of membrane bound protein antibodies comprising a plurality of membrane bound protein antibodies that are specific to membrane bound proteins of a particular class of membrane bound proteins. Membrane bound proteins belong to a class of membrane bound proteins when they share one or more attributes in common in a structural or topological feature, a collection that assigns defined characteristics to a set of structural or topological features. Membrane bound proteins belonging to a class of membrane bound proteins can be identified by searching for genes sharing one or more structural or topological features. The common attribute could be, for example, a common structural feature, a particular number of transmembrane spanning domains, a common topology, a common biological process or a common molecular function.

The wealth of information that exists in published, peer-reviewed literature concerning the function of human membrane bound protein genes and transmembrane proteins have been organized and curated. Of the approximately 40,000 transcribed units in the human genome, approximately 5,600 of those code for annotated membrane bound proteins.

In some embodiments, proteins belonging to a class of proteins are membrane bound proteins.

In some embodiments, membrane bound proteins belonging to a class of membrane bound proteins are membrane bound proteins which contain a particular number of transmembrane spanning domains.

In some embodiments, membrane bound proteins belonging to a class of membrane bound proteins are membrane bound proteins which contain a single transmembrane spanning domain.

In some embodiments, membrane bound proteins belonging to a class of membrane bound proteins are membrane bound proteins which contain two or more transmembrane spanning domains. In some embodiments, membrane bound proteins belonging to a class of membrane bound proteins are membrane bound proteins which contain three or more transmembrane spanning domains. In some embodiments, membrane bound proteins belonging to a class of membrane bound proteins are membrane bound proteins which contain four or more transmembrane spanning domains. In some embodiments, membrane bound proteins belonging to a class of membrane bound proteins are membrane bound proteins which contain five or more transmembrane spanning domains. In some embodiments, membrane bound proteins belonging to a class of membrane bound proteins are membrane bound proteins which contain six or more transmembrane spanning domains. In some embodiments, membrane bound proteins belonging to a class of membrane bound proteins are membrane bound proteins which contain seven or more transmembrane spanning domains.

In some embodiments, membrane bound proteins belonging to a class of membrane bound proteins are membrane bound proteins which contain a particular number of subunits that make up the functional membrane bound protein.

In some embodiments, membrane bound proteins belonging to a class of membrane bound proteins are membrane bound proteins which contain a single subunit that makes up the functional membrane bound protein.

In some embodiments, membrane bound proteins belonging to a class of membrane bound proteins are membrane bound proteins which contain two or more subunits that make up the functional membrane bound protein.

In some embodiments, membrane bound proteins belonging to a class of membrane bound proteins are membrane bound proteins which contain three or more subunits that make up the functional membrane bound protein. In some embodiments, membrane bound proteins belonging to a class of membrane bound proteins are membrane bound proteins which contain four or more subunits that make up the functional membrane bound protein. In some embodiments, membrane bound proteins belonging to a class of membrane bound proteins are membrane bound proteins which contain five or more subunits that make up the functional membrane bound protein. In some embodiments, membrane bound proteins belonging to a class of membrane bound proteins are membrane bound proteins which contain six or more subunits that make up the functional membrane bound protein. In some embodiments, membrane bound proteins belonging to a class of membrane bound proteins are membrane bound proteins which contain seven or more subunits that make up the functional membrane bound protein. In some embodiments, membrane bound proteins belonging to a class of membrane bound proteins are membrane bound proteins which contain eight or more subunits that make up the functional membrane bound protein.

In some embodiments, membrane bound proteins belonging to a class of membrane bound proteins are membrane bound proteins that have a single TM stretch of hydrophobic residues, with the portion of the polypeptide on the $NH_2$-terminal side of the TM domain exposed on the exterior side of the membrane and the COOH-terminal portion exposed on the cytoplasmic side, for example, type I membrane bound proteins. In some embodiments, the membrane bound proteins are subdivided into types Ia (cleavable signal sequences) and Ib (without cleavable signal sequence).

In some embodiments, membrane bound proteins belonging to a class of membrane bound proteins are membrane bound proteins that have a single TM stretch of hydrophobic residues, with the portion of the polypeptide on the COOH-terminal side of the TM domain exposed on the exterior side of the membrane and the $NH_2$-terminal portion exposed on the cytoplasmic side, for example, type I membrane bound proteins.

In some embodiments, membrane bound proteins belonging to a class of membrane bound proteins are membrane bound proteins that have multiple transmembrane domains in a single polypeptide chain, for example, type III membrane bound proteins. In some embodiments, the membrane bound proteins are subdivided into a and b: type IIIa molecules can have cleavable signal sequences while type IIIb can have their amino termini exposed on the exterior surface of the membrane, but do not have a cleavable signal sequences.

In some embodiments, membrane bound proteins belonging to a class of membrane bound proteins are membrane bound proteins that have multiple homologous domains which make up an assembly that spans the membrane multiple times, for example, type IV membrane bound proteins. In some embodiments, the domains reside on a single polypeptide chain. In some embodiments, the domains reside on more than one individual chain.

In some embodiments, membrane bound proteins belonging to a class of membrane bound proteins are alpha-helical membrane bound proteins. In some embodiments, membrane bound proteins belonging to a class of membrane bound proteins are beta-barrel membrane bound proteins.

In some embodiments, membrane bound proteins belonging to a class of membrane bound proteins are light absorption-driven transporters, for example, bacteriorhodopsin-like proteins including rhodopsin, bacterial photosynthetic reaction centers and photosystems I and II, and light-harvesting complexes from bacteria and chloroplasts.

In some embodiments, membrane bound proteins belonging to a class of membrane bound proteins are oxidoreduction-driven transporters, for example, transmembrane cytochrome b-like proteins: coenzyme Q-cytochrome c reductase (cytochrome bc1); cytochrome b6f complex; formate dehydrogenase, respiratory nitrate reductase; succinate-coenzyme Q reductase (fumarate reductase); and succinate dehydrogenase; or cytochrome c oxidases from bacteria and mitochondria.

In some embodiments, membrane bound proteins belonging to a class of membrane bound proteins are electrochemical potential-driven transporters, for example, proton or sodium translocating F-type and V-type ATPases.

In some embodiments, membrane bound proteins belonging to a class of membrane bound proteins are P—P-bond hydrolysis-driven transporters, for example, P-type calcium ATPase, calcium ATPase regulators phospholamban and sarcolipin. ABC transporters: BtuCD, multidrug transporter, and molybdate uptake transporters, and general secretory pathway translocases.

In some embodiments, membrane bound proteins belonging to a class of membrane bound proteins are porters (uniporters, symporters, antiporters), for example, mitochondrial carrier proteins; Major Facilitator Superfamily (Glycerol-3-phosphate transporter, Lactose permease, and Multidrug transporter EmrD); resistance-nodulation-cell division (multidrug efflux transporter AcrB); dicarboxylate/amino acid:cation symporter (proton glutamate symporter); monovalent cation/proton antiporter (Sodium/proton antiporter 1 NhaA); neurotransmitter sodium symporter; ammonia transporters; and drug/metabolite transporter (small multidrug resistance transporter EmrE).

In some embodiments, membrane bound proteins belonging to a class of membrane bound proteins are alpha-helical channels including ion channels, for example, voltage-gated ion channel like, including potassium channels KcsA and KvAP, and inward-rectifier potassium ion channel Kirbac; large-conductance mechanosensitive channel, MscL; small-conductance mechanosensitive ion channel (MscS); corA metal ion transporters; ligand-gated ion channel of neurotransmitter receptors (acetylcholine receptor); aquaporins; chloride channels; and outer membrane auxiliary proteins (polysaccharide transporter) and α-helical membrane bound proteins from the outer bacterial membrane In some embodiments, membrane bound proteins belonging to a class of membrane bound proteins are enzymes, for example methane monooxygenase; rhomboid protease, and disulfide bond formation protein (DsbA-DsbB complex).

In some embodiments, membrane bound proteins belonging to a class of membrane bound proteins are proteins with alpha-helical transmembrane anchors, for example, T cell receptor transmembrane dimerization domain, cytochrome c nitrite reductase complex, steryl-sulfate sulfohydrolase, stannin, glycophorin A dimer, inovirus (filamentous phage) major coat protein, pilin, pulmonary surfactant-associated protein, monoamine oxidases A and B, fatty acid amide hydrolase, cytochrome P450 oxidases, corticosteroid 11β-dehydrogenases, signal peptide peptidase, and membrane protease specific for a stomatin homolog.

In some embodiments, membrane bound proteins belonging to a class of membrane bound proteins are beta-barrels composed of a single polypeptide chain, for example, beta barrels from eight beta-strands and with shear number of ten: ompA-like transmembrane domain (OmpA), virulence-related outer membrane protein family (OmpX), outer membrane protein W family (OmpW), antimicrobial peptide resistance and lipid A acylation protein family (PagP), lipid A deacylase PagL, and opacity family porins (NspA); autotransporter domain; fadL outer membrane protein transport family, including Fatty acid transporter FadL; general bacterial porin family, known as trimeric porins; maltoporin, or sugar porins; nucleoside-specific porin; outer membrane phospholipase A1; tonB-dependent receptors and their plug domain. They are ligand-gated outer membrane channels; outer membrane protein OpcA family; and outer membrane protein G porin family.

In some embodiments, membrane bound proteins belonging to a class of membrane bound proteins are beta-barrels composed of several polypeptide chains, for example, trimeric autotransporter, outer membrane efflux proteins, also known as trimeric outer membrane factors including TolC and multidrug resistance proteins, and mspA porin and α-hemolysin.

In some embodiments, membrane bound proteins belonging to a class of membrane bound proteins are integral membrane proteins. In some embodiments, membrane bound proteins belonging to a class of membrane bound proteins are ipid-linked proteins. In some embodiments, membrane bound proteins belonging to a class of membrane bound proteins are peripheral membrane proteins.

In some embodiments, membrane bound proteins belonging to a class of membrane bound proteins are in an open confirmation. In some embodiments, membrane bound proteins belonging to a class of membrane bound proteins are in an closed confirmation.

In some embodiments, membrane bound proteins belonging to a class of membrane bound proteins are plasma membrane bound proteins. In some embodiments, membrane bound proteins belonging to a class of membrane bound proteins are nuclear membrane bound proteins. In some embodiments, membrane bound proteins belonging to a class of membrane bound proteins are in the outer nuclear membrane bound proteins. In some embodiments, membrane bound proteins belonging to a class of membrane bound proteins are inner nuclear membrane bound proteins. In some embodiments, membrane bound proteins belonging to a class of membrane bound proteins are mitochondrial membrane bound proteins. In some embodiments, membrane bound proteins belonging to a class of membrane bound proteins are outer mitochondrial membrane bound proteins. In some embodiments, membrane bound proteins belonging to a class of membrane bound proteins are inner mitochondrial membrane bound proteins. In some embodiments, membrane bound proteins belonging to a class of membrane bound proteins are endoplasmic reticulum membrane bound proteins. In some embodiments, membrane bound proteins belonging to a class of membrane bound proteins are Golgi complex membrane bound proteins. In some embodiments, membrane bound proteins belonging to a class of membrane bound proteins are endosome membrane bound proteins. In some embodiments, membrane bound proteins belonging to a class of membrane bound proteins are peroxisome membrane bound proteins. In some embodiments, membrane bound proteins belonging to a class of membrane bound proteins are lysosome membrane bound proteins.

The present invention also provides a library comprising a plurality of membrane bound protein antibodies specific to a plurality of membrane bound protein s in which at least about 5%, 10%, 20%, 30%, 40%, 50%, 60%, 70%, 80%, 90%, 99% or 100% of the membrane bound proteins are in a particular class, such as any of those described above.

Method of Producing a Library of Antibodies

Also provided herein are methods of producing a library of antibodies. In one embodiment, the method comprises (a) immunizing an animal with a virion or plurality of virions expressing or containing one or more membrane bound proteins; (b) isolating membrane bound protein antibody-generating cells from the animal; (c) isolating one or a plurality of membrane bound protein antibodies from the membrane bound protein antibody-generating cells; (d) screening the one or plurality of membrane bound protein antibodies of step c) with a protein array (such as a human proteome array or human membrane bound proteome array); and (e) selecting a membrane bound protein antibody that can be monospecific for a single target on the proteome array. In one embodiment, the method can further comprise pre-screening the one or plurality of membrane bound protein antibodies from the membrane bound protein antibody-generating cells prior to step c).

The animal can be a non-human animal, such as a bovine, avian, canine, equine, feline, ovine, porcine, or primate animal. The animal can be a mammal, such as a mouse, rat, rabbit, cat, dog monkey, or goat.

The animal can be immunized with one or a plurality of membrane bound proteins, wherein the membrane bound proteins are contained within a virion, for example are contained within the envelope of the virion.

A library of antibodies can comprise a plurality of antibodies, wherein at least one or each antibody of the plurality of antibodies can specifically bind a plurality of membrane bound proteins. In some embodiments, at least about 1% to 100% of the plurality of antibodies can be antibodies produced or validated by the any of the methods described herein. In some embodiments, at least about 1% to 100% of the plurality of antibodies are antibodies produced by a method other than the methods described herein. A method of validating one or more antibodies, or at least about 1% to 100% of the antibodies, in any of the libraries or pluralities of antibodies described herein can comprise analyzing the one or more antibodies by a method selected from the group comprising immunoprecipitation (IP), immunohistochemistry (IHC), Western Blot (WB), Enzyme Linked Immunosorbant Assay (ELISA), immunofluorescence (IF), immunocytochemistry (ICC), siRNA knockdown, or any combination thereof.

In some embodiments, at least one or each antibody of the plurality of antibodies can be monospecific. In some embodiments at least about 1% to 100% of the plurality of antibodies can be monospecific. At least one of the antibodies in the library can be monospecific. At least about 1% of the antibodies in the library can be monospecific. For example, at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the antibodies in the library can be monospecific. In one embodiment, at least one or each of the antibodies in the library or plurality of antibodies can be monospecific. At least about one of the antibodies in the array can be monospecific. For example, at least about 2, 3, 4, 5, 6, 7, 8, 9, 10, 11, 12, 13, 14, 15, 16, 17, 18, 19, 20, 25, 30, 35, 40, 45, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 1,000, 2,000, 3,000, 4,000, 5,000, 5,500, 5,600, or more of the antibodies in the array can be monospecific.

In some embodiments, at least one or each antibody of the plurality of antibodies has a binding affinity of at least about $10^{-7}$M ($K_D$) for a membrane bound protein. In some embodiments, at least about 1% to 100% of the plurality of antibodies has a binding affinity of at least about $10^{-7}$M ($K_D$) for a membrane bound protein. At least about one of the antibodies in the library can have a binding affinity of at least about $10^{-7}$M ($K_D$), such as at least about $10^{-8}$M, $10^{-9}$M, $10^{-10}$M, $10^{-11}$M, $10^{-12}$M, $10^{-13}$M, $10^{-14}$M, $10^{-15}$M, or $10^{-16}$M, for its target. At least about 1% of the antibodies in the library can be monospecific and at least about one of the antibodies in the library can have a binding affinity of at least about $10^{-7}$M ($K_D$). For example, at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the antibodies in the library can be monospecific and at least about one of the antibodies in the library can have a binding affinity of at least about at least about $10^{-8}$M, $10^{-9}$M, $10^{-10}$M, $10^{-11}$M, $10^{-12}$M, $10^{-13}$M, $10^{-14}$M, $10^{-15}$M, or $10^{-16}$M.

The plurality of antibodies can comprise at least about 50 different antibodies. For example, the plurality of antibodies can comprise at least about 100, 200, 300, 400, 500, 600, 700, 800, 900, 1,000, 2,000, 3,000, 4,000, 5,000, 5,500, 5,600, or more different antibodies. For example, a library of antibodies can comprise at least about 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 1000 antibodies.

In some embodiments, a library of antibodies can comprise at least about 2 of the same one or more antibodies. For example, a library of antibodies can comprise at least about 3, 4, 5, 6, 7, 8, 9, 10, 11, 12, 13, 14, 15, 16, 17, 18, 19, 20, 25, 30, 35, 40, 45, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 1000 of the same one or more antibodies.

The library of virions containing the one or more membrane bound proteins. For example, a library of virions can comprise at least about 100, membrane proteins with a transmembrane domain, such as at least about 200, 300, 400, 500, 600, 700, 800, 900, 1,000, 2,000, 3,000, 4,000, 5,000, 5,500, 5,600, or more different membrane proteins with a transmembrane domain. The library of virions can represent at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or 60% of an organism's proteome. The library of virions can represent at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or 60%, 70%, 80%, 90%, or 100% of an organism's membrane bound proteome. The library of virions can comprise a plurality of membrane bound proteins that represent a substantial portion or an entire organism's membrane bound proteome, such as a bacterial, viral, or fungal, proteome. The library of virions can comprise a plurality of membrane bound proteins that represent a substantial portion or an entire proteome of an insect or mammal, such as a mouse, rat, rabbit, cat, dog, monkey, goat, or human. The library of virions containing or expressing the plurality of membrane bound proteins that can also comprise a fusion protein library that represents an organism's membrane bound proteome in unpurified form, such as a collection of overexpressing virions.

The membrane bound protein antibody-generating cells from the animal can be lymphoid cells, such as B-cells. The membrane bound protein antibody-generating cell can be used to generate a hybridoma, for example, fused to an immortal cell such as a myeloma cell, to create a hybridoma.

In one embodiment, a pre-screening step can be performed, wherein a plurality of membrane bound protein antibodies from the membrane bound protein antibody-generating cells are screened prior to isolating a plurality of membrane bound protein antibodies from the membrane bound protein antibody-generating cells. Pre-screening can be performed by using the serum or supernatant of the membrane bound protein antibody-producing cells to determine binding of membrane bound protein antibodies from the membrane bound protein antibody-generating cells with a mixture comprising one or more target membrane bound proteins, such as native membrane bound proteins. The pre-screening can be performed using immunohistochemistry, immunocytochemistry, ELISA, chromatography, or any other suitable methods known in the art to determine binding. Pre-screening can be used to select the membrane bound protein antibody-generating cells (which can include membrane bound protein antibody-secreting cells that have been fused to immortalized cells, such as hybridomas), for further screening, such as by a proteome array or membrane bound proteome array as described herein.

A plurality of membrane bound protein antibodies from the membrane bound protein antibody-generating cells can be isolated, with or without a previous pre-screening step, before being subjected to a screening with an entire, or portion of, a proteome or membrane bound proteome of an organism. For example, the isolated membrane bound protein antibodies can be screened with at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's proteome. For example, the isolated membrane bound protein antibodies can be screened with at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's membrane bound proteome. For example, the isolated antibodies can be screened with at least about 11,000, 12,000, 13,000, 14,000, 15,000, 16,000, 17,000, 18,000, 19,000, or 20,000 proteins of an organism. For example, the isolated antibodies can be screened with at least about 100, 200, 300, 400, 500, 600, 700, 800, 900, 1,000, 2,000, 3,000, 4,000, 5,000, 5,500, or 5,600, membrane bound proteins of an organism. The proteome or membrane bound proteome can be a bacterial, viral, fungal proteome. The proteome or membrane bound proteome can be of an insect or mammal, such as a mouse, rat, rabbit, cat, dog, monkey, goat, or human. In some embodiments, the proteome or membrane bound proteome can be of a human.

For example, the isolated membrane bound protein antibodies can be screened with at least about 0.5% of the human proteome. In one embodiment, the isolated antibodies can be screened with at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human proteome. For example, the isolated membrane bound protein antibodies can be screened with at least about 0.5% of the human membrane bound proteome. In one embodiment, the isolated antibodies can be screened with at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human membrane bound proteome. The proteome, membrane bound proteome, or portions thereof, which are used to screen the membrane bound protein antibodies can be present on an array.

After screening, a membrane bound protein antibody can be selected based on its binding profile. For example, a membrane bound protein antibody can be selected if it binds to a single target of the proteome or membrane bound proteome, such as to a single target of a human proteome array, for a library described herein.

The method can be used to perform high-throughput production of membrane bound protein antibodies. For example virions to immunize mice can be produced in a high-throughput manner. This can be done by: 1) directed production of virions containing heterologous membrane bound proteins from a gene expression library, where membrane bound proteins of interest can be expressed in the virions as needed. The virions containing membrane bound proteins for injection can include subcellular components, such as cell and intracellular membranes, organelles, particles, or protein complexes and may be prepared using differential centrifugation or other well-known methods. These immunizations with complex mixtures of membrane bound proteins in lipid bilayers may eventually produce membrane bound protein antibodies against the most highly immunogenic membrane bound proteins; in this event, the virion sources can be immunodepleted using previously isolated antibodies to remove any especially antigenic membrane bound proteins. In addition, membrane proteins can be chromatographed in their native or denatured state(s), by size-exclusion, ion-exchange, hydrophobic or affinity chromatography or by using individually collected small fractions to immunize with dozens to hundreds rather than thousands of membrane bound proteins. Specific techniques to target specific classes of membrane bound proteins can be used. For example, virions containing membrane bound proteins involved in SNO signaling may be purified by Immobilized Metal Affinity Chromatography (IMAC) and eluted metal-free virions containing the membrane bound proteins may then be used as antigens for immunization, or virions containing transmembrane phosphoproteins may be bound to TiO2 affinity matrices and thereby greatly enriched. Native proteins isolated or obtained directly from living or fixed virions can be preferred sources of immunogens.

The high-throughput methods can also comprise a short timescale immunization to produce membrane bound protein antibody-secreting lymphoid cells. For example, animals can be immunized with multiple virions containing multiple membrane bound proteins and adjuvant preparations by way of the rear footpads. Popliteal lymph nodes are collected from 7 to 21 days post-immunization. Lymph nodes in immunized animals are directly revealed by injection with Evans blue at the footpad.

The high-throughput method can also comprise generating the membrane bound protein antibodies in fusion tag-tolerant mice. Since many membrane bound proteins are expressed as tagged fusions, a line of fusion tag-expressing mice (mice that actively express a fusion tag) can be used to increase the yield of specific membrane bound protein antibodies raised against the non-fusion tag components of the fusion membrane bound proteins and eliminate generation of anti-fusion tag antibody.

A high-throughput method for producing membrane bound protein antibodies can also comprise creation of cell fusions/hybridomas for membrane bound protein antibody production. Primed lymphoid cells and myeloma cells are fused and fusion products are either plated onto semisolid medium (methylcellulose) containing fluorescently tagged membrane bound protein antibodies that recognize the desired subclass of immunoglobulin molecules, or into semisolid media containing fluorescently tagged virions containing heterologous membrane bound proteins that will mark colonies secreting the desired membrane bound protein antibodies. A combination of the above methods may also be used. Fluorescently marked colonies are rescued from semisolid medium to liquid medium, using an inverted fluorescence microscope in combination with hand-picking using Drummond microcapillary and Drummond WireTrol devices, followed by outgrowth of the individual clones.

Any suitable method may be used to generate the antibodies disclosed herein. For example, a virion, comprising a heterologous membrane bound protein or a plurality of heterologous membrane bound proteins, can be produced in vitro, such as by any recombinant methods known in the arts. The virion composition can further comprise a suitable carrier or diluent and can be administered to the animal under conditions that permit the production of antibodies. For enhancing the antibody production capability of the animal, complete or incomplete Freund's adjuvant can also be administered. The virion composition can be administered once a day or one or more times a week, such as one a week, twice a week, thrice a week, four times a week, five times a week, six times a week, or seven times a week, or every 2 to 4 weeks, such as every 2 weeks, 3 weeks, 4 weeks, 5 weeks, 6 weeks, 7 weeks, 8 weeks, or more. The virion composition can be administered once, or a total of about 2 times to about 10 times. The virion composition can be administered 2, 3, 4, 5, 6, 7, 8, 9, 10 or more times. Administration can be by any method known in the art, such as, but not limited to, administration subcutaneously, intraperitoneally, intravenously, via foot pad, and the like.

For preparing monoclonal antibody-producing cells, an individual animal whose antibody titer has been confirmed can be selected, and after the final immunization, such as from 2 to 5 days after, its spleen or lymph node can be harvested and antibody-producing cells contained therein can be fused with myeloma cells to prepare the desired monoclonal antibody producer hybridoma.

Hybridomas can be generated by fusing two cell types, for example, immune B cells and a culture-stable myeloma cell line. This can be carried out in the presence of a fusogenic compound such as PEG. The desired hybrid cell products can be selected from among the unfused cells by taking advantage of the presence of two metabolic routes of pyrimidine/purine synthesis, the de novo and scavenging pathways. The myeloma cell lines commonly used are deficient in the salvage pathway, as they have been selected for resistance to 8-azaguanine or 6-thioguanine and are thus hypoxanthine-guanine phosphoribosyl transferase (HGPRT) deficient. Without the salvage pathway for viability, these cells require the de novo pathway, which, however, can be blocked with aminopterin. B cell myeloma hybrids can grow in the presence of aminopterin because the immune B cell donates a wild-type HPRT enzyme that supports processing of scavenged hypoxanthine (H) and thymidine (T). Fusion reactions can thus be plated in HAT medium to eliminate unfused immune cells and myeloma cells but can be permissive for hybridoma outgrowth. The most useful myeloma cell lines are those such as X63-Ag8.653, NSW and Sp2/0-Ag-14, which do not secrete their own immunoglobulin heavy or light chains that would contaminate the product contributed by the B cell. Examples of myeloma cells include, but are not limited to, NS-1, P3U1, SP2/0, AP-1 and the like cells. The cell fusion can be carried out according to known methods.

Measurement of the antibody titer in antiserum can be carried out, for example, by reacting the labeled protein and antiserum and then measuring the activity of the labeling agent bound to the antibody. The proportion of the number of antibody producer cells (spleen cells) and the number of myeloma cells to be used can be optimized and performed by methods known in the art. The proportion of the number of antibody producer cells (spleen cells) and the number of myeloma cells to be used can be about 1:1 to about 20:1, for example about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1 ratio can be used. PEG, such as PEG 1000-PEG 6000 can be added in a concentration of about 10% to about 80%, for example 10%, 15%, 20%, 25%, 30%, 35%, 40%, 45%, 50%, 55%, 60%, 65%, 70%, 75%, or 80%. Cell fusion can be carried out efficiently by incubating a mixture of both cells at about 20° C. to about 40° C., such as about 30° C. to about 37° C. for about 1 minute to 10 minutes. For example, a mixture of both cells can be can be incubated at about 20° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. for about 1, 2, 3, 4, 5, 6, 7, 8, 9, or 10 minutes.

Various methods can be used for screening for a hybridoma producing the antibody against the heterologous protein, e.g., a heterologous membrane bound protein of a virion, as known in the arts. For example, a supernatant of the hybridoma can be added to a solid phase (e.g., microplate) to which antibody can be adsorbed directly or together with a carrier and then an anti-immunoglobulin antibody (for example, if mouse cells are used in cell fusion, anti-mouse immunoglobulin antibody can be used) or Protein A or Protein G labeled with a radioactive substance or an enzyme can be added to detect a monoclonal antibody against the membrane bound protein of the virion bound to the solid phase. Alternately, a supernatant of the hybridoma can be added to a solid phase to which an anti-immunoglobulin antibody or Protein A can be adsorbed and then the protein labeled with a radioactive substance or an enzyme can be added to detect a monoclonal antibody against the membrane bound protein of the virion bound to the solid phase.

Selection of a monoclonal antibody can be carried out according to any known method or its modification. A medium for animal cells to which HAT (hypoxanthine, aminopterin, and thymidine) are added can be employed. Any selection and growth medium can be employed as long as the hybridoma can grow. For example, RPMI 1640 medium or GIT medium containing about 1% to 20%, such as 1%, 2%, 3%, 4%, 5%, 6%, 7%, 8%, 9%, 10%, 11%, 12%, 13%, 14%, 15%, 16%, 17%, 18%, 19%, or 20% fetal bovine or fetal calf serum, a serum free medium for cultivation of a hybridoma (SFM-101, Nisei Seiyaku), and the like can be used. The cultivation can be carried out at 20° C. to 40° C., such as about 20° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. for about 5 days to 3 weeks, such as about 5 days, 6 days, 1 week, 2 weeks, or three weeks under about 1-10% $CO_2$ gas, such as about 1%, 2%, 3%, 4%, 5%, 6%, 7%, 8%, 9%, or 10% $CO_2$ gas. An antibody titer of the supernatant of a hybridoma culture can be measured according to the same manner as described above with respect to the antibody titer of the anti-protein in the antiserum.

Separation and purification of a monoclonal antibody to a biomarker can be carried out according to the same manner as those of conventional polyclonal antibodies, such as separation and purification of immunoglobulins, ((for example, salting-out, alcoholic precipitation, isoelectric point precipitation, electrophoresis, adsorption and desorption with ion exchangers) (e.g., DEAE)), ultracentrifugation, gel filtration, or a specific purification method wherein an antibody can be collected with an active adsorbent such as an antigen-binding solid phase, Protein A, or Protein G, and dissociating the binding to obtain an antibody.

Polyclonal antibodies may be prepared by any known method or modifications of these methods. For example, a biomarker composition comprising a biomarker and a carrier protein can be prepared and the animal can be immunized by the virion composition as described. A material containing the antibody against the membrane bound protein of the virion can be recovered from the immunized animal and the antibody can be separated and purified.

For the monoclonal membrane bound protein antibodies generated in the high-throughput method, using the virions described herein, the responsible membrane bound protein antigen can be identified by protein microarray deconvolution. Single-step deconvolution can be performed.

For example, multiple virions containing multiple membrane bound proteins are used to generate hybridomas, a two-dimensional pooling strategy can be employed to reveal identity of membrane bound protein antigens that at least one or each monoclonal membrane bound protein antibody would recognize. Supernatants of hybridomas are arrayed in two-dimensional grids and pooled both horizontally and vertically in 3-by-3 to 100-by-100 pool sizes. Three-dimensional pooling strategies can also be performed in which hybridomas are arrayed in plate sets to generate plate pools and horizontal and vertical pools in 3-by-3-by-3 to 100-by-100-by-100 format. The resulting pools are hybridized individually to the protein microarrays and scored using microarray analysis software. The shared positives (hits) of each horizontal and vertical pair or those at each 3-way intersection of plate, horizontal and vertical pools (called a trio) in two- and three-dimensional designs, respectively, are identified as the membrane bound protein antigens recognized by the monoclonal membrane bound protein antibody at the intersection of the same pairs or trios. When necessary, the identified membrane bound protein antigens are validated by probing the microarrays with the corresponding membrane bound protein antibodies. The pooling strategy can reduce the cost of characterizing or producing membrane bound protein antibodies because the cost of the arrays can be high, and use of a e.g. 10 by 10 pool reduces the number of arrays needed to analyze 100 clones from 100 to 20; for a 20×20 pool it reduces the number of arrays needed from 400 to 40. The 3-dimensional pools, for example, can screen a pool of 4096 hybridomas, while a 16-by-16-by-16 3-D strategy requires only 48 arrays. Using the 10-by-10 strategy, 820 arrays can be used.

Characterization of the monoclonal membrane bound protein antibodies generated in the high-throughput method can be performed using whole proteome or whole membrane bound proteome microarrays. The microarrays can be used to determine the specific membrane bound protein antigens to which a given monoclonal membrane bound protein antibody binds. Critical quality information about monoclonal membrane bound protein antibody affinity, potential cross reactivity or lack of crossreactivity with other antigens or membrane bound protein antigens are all provided by an array analysis.

Production of monoclonal membrane bound protein antibodies in the high-throughput method can be from fusion clones. Monoclonal membrane bound protein antibodies are produced in vitro or in vivo in the desired quantities. These can be purified using various well-established methods.

On the basis of the characterization of monoclonal membrane bound protein antibodies using protein microarrays, monoclonal membrane bound protein antibodies of high quality (e.g., high affinity and low cross reactivity) can be selected and used to produce antibody arrays. The membrane bound protein antibodies are selected and their concentrations normalized to a similar titer. They can be arrayed in a multiwell format (e.g. 96- 384- or 1562-well) with proper positive (e.g., diluted human IgG) and negative (e.g., human Gimp and BSA) controls to fabricate antibody microarrays using a microarray robot (e.g., Nan print, Array It, Inc.). The arrangement of the monoclonal membrane bound protein antibodies in different microarray configurations may be customized to facilitate a range of proteome-wide or membrane bound proteome-wide studies.

Method of Using a Library of Membrane Protein Antibodies

Also provided herein is a method of identifying a membrane bound protein antibody for a membrane bound protein target comprising contacting a virion containing a membrane bound protein target with a library of antibodies, determining binding between the membrane bound protein target in the virion and the plurality of membrane bound protein antibodies; and identifying a membrane bound protein antibody for the membrane bound protein of the virion when the membrane bound protein of the virion binds to a membrane bound protein antibody of the library. A method of identifying a membrane bound protein target comprising contacting a virion containing a membrane bound protein target with a library of membrane bound protein antibodies, determining binding between the membrane bound protein target of the virion and the plurality of membrane bound protein antibodies; and identifying the membrane bound protein target antibody when the membrane bound protein target of the virion binds to a membrane bound protein antibody of the library, is also provided. The library of membrane bound protein antibodies can be attached to a substrate such that the membrane bound protein target can be contacted with an array comprising the library of membrane bound protein antibodies.

The library can comprise of a plurality of different membrane bound protein antibodies, such as described above. For example, the library of membrane bound protein antibodies can comprise membrane bound protein antibodies that are produced by the same platform. The library can comprise a plurality of different membrane bound protein antibodies, wherein within the plurality or a subset of the plurality (such as at least about 10%, 20%, 30%, 40%, 50%, 60%, 70%, 80%, 90%, 95%, 99% or 100% of the plurality), the membrane bound protein antibodies are produced by the same platform, are monospecific, bind a native form of its target membrane bound protein; are monoclonal; are immunoprecipitating membrane bound protein antibodies; are IgG membrane bound protein antibodies (e.g. membrane bound protein antibodies of IgG isotype); have a binding affinity for its membrane bound protein target that can be similar to that of another membrane bound protein antibody of the plurality of membrane bound protein antibodies (for example, within at least about 1, 2, 3, 4, 5, 6, 7, 8, 9, 10, 11, 12, 13, 14, 15, 16, 17, 18, 19, or 20%); at least one or each membrane bound protein antibody has a binding affinity of at least about $10^{-7}$M ($K_D$) (for example, such as at least about $10^{-8}$M, $10^{-9}$M, $10^{-10}$M, $10^{-11}$M, $10^{-12}$M, $10^{-13}$M, $10^{-14}$M, $10^{-15}$M, or $10^{-16}$M) for its membrane bound protein target; or any combination thereof. The library may comprise at least about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 1000 different monoclonal membrane bound protein antibodies, bind at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's proteome (e.g. a human proteome), bind at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's membrane bound proteome, or any combination thereof.

Also provided herein is a method of identifying a membrane bound protein antibody monospecific for a membrane bound protein, such as a human membrane bound protein, comprising: contacting a plurality of membrane bound protein antibodies with a proteome or membrane bound proteome array, such as a human proteome or membrane bound proteome array; determining binding between the plurality of membrane bound protein antibodies and the targets present on the proteome array; and identifying a membrane bound protein antibody as monospecific. The array can comprise a plurality of proteins that comprise at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's proteome. For example, the proteome array can comprise at least about 11,000, 12,000, 13,000, 14,000, 15,000, 16,000, 17,000, 18,000, 19,000, or 20,000 proteins of an organism. The array can comprise a plurality of membrane bound protein antigens or membrane bound proteins that comprise at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's membrane bound proteome. For example, the proteome array can comprise at least about 200, 300, 400, 500, 600, 700, 800, 900, 1,000, 2,000, 3,000, 4,000, 5,000, 5,500, or 5,600 membrane bound proteins of an organism. The organism can be a bacterium, virus, or fungus. The organism can be of an insect or mammal, such as a mouse, rat, rabbit, cat, dog, monkey, goat, or human. For example, the proteome can comprise at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human proteome. For example, the membrane bound proteome can comprise at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the human membrane bound proteome.

Binding can be detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays.

Antibody binding can be detected by detecting a label on the primary antibody. Alternatively, the primary antibody can be detected by detecting binding of a secondary antibody or reagent to the primary antibody. For example, the secondary antibody can be labeled. In some embodiments, an automated detection assay or high-throughput system can be utilized. For example, in a capture micro-enzyme-linked immunosorbent assay (ELISA), an antibody/antigen reaction can be made measurable by immobilization of the antibody and subsequent direct or indirect colorimetric, fluorescent, luminescent or radioactive detection of bound, labeled antigens. For example, the antigen can be labeled by biotin or other labels, which will allow downstream detection.

The immobilized membrane bound protein antibodies will generally bind to a single antigenic determinant present. The antigenic determinant can be labeled, such as through labeling of the biomarker comprising the antigenic determinant. The specificity of this reaction will permit quantification in the ELISA measurements. The ELISA reaction can be used in a high throughput format to screen all hybridoma supernatants via the following steps. Screening assays built on other principles than an ELISA can be deployed (e.g., antibody microarrays, high-throughput screening based on MALDI/MS and/or multi-channel capillary electrophoresis). ELISA or microarray data are evaluated, e.g., by published methods. The goal of the data analysis process can be the selection of hybridoma supernatants that show the best collection with an important clinical parameter and are specific to one of the analyte groups.

Uses of the Microarrays

The microarrays of the invention can be used in medical diagnostics, drug discovery, molecular biology, immunology and toxicology.

Microarrays of immobilized antibodies or virions prepared in accordance with the invention can be used for large scale binding assays in numerous diagnostic and screening applications. The multiplexed measurement of quantitative variation in levels of large numbers of targets (e.g. membrane bound proteins) allows the recognition of patterns defined by several to many different targets (e.g., membrane bound proteins). One can simultaneously assess many physiological parameters and disease-specific patterns.

Arrays of immobilized virions can also be used to identify ligands for example, peptides, lipids, fatty acids, small molecules, etc., for receptor proteins, such as GPCRs, channels, receptor tyrosine kinase, and transporters. Fluorescent dyes and/or radioisotopes can be used to label these ligands for detecting binding activity and specificity of the ligands. Antibodies that specifically recognize those ligands can also be used as detection reagents to determine ligand-receptor binding activities on the arrays of immobilized virions. Coupled with a reporter molecule, for example, fluorescent dyes (e.g., Fluo8, DiBAC4, and ANG-2), arrays of immobilized virions can also be used to screen drug screens against membrane proteins, for example, channel proteins. For instance, multiple virion species that at least one or each displays a particular human ion channel can be arrayed into 96-, 384-, 1536-well format dishes such that one drug can be assayed against multiple (e.g., 2-200) channel proteins simultaneously. For example, a known ligand can be preincubated on an array of immobilized virions, followed by antibody binding assays. In this way, antibodies specifically recognizing a particular conformation of a membrane protein due to binding to its ligand can be readily identified.

Arrays of immobilized virions can also be used to screen antibodies that can specifically recognize the ectodomains of membrane bound proteins. For example, monoclonal antibodies generated by immunizing mice with recombinant virions can be incubated on an array of immobilized virions, followed by a detection step with labeled secondary antibodies.

Arrays of immobilized virions can also be used to screen for antibodies, ligands, and binding partners that can specifically recognize or interact with the intracellular-domains of membrane bound proteins. For example, monoclonal antibodies generated by immunizing mice with recombinant virions can be incubated on an array of immobilized virions, wherein the virions display one or more of the intracellular-domains of a heterologous membrane bound protein, followed by a detection step with labeled secondary antibodies. For example, a given multi-pass membrane bound protein in an $N_{out}$-$C_{in}$ topology can be engineered to remove positive charges from its cytoplasmic loops, and one or more positive charged residues (e.g., lysine and arginine) can be added to its N-terminal loop region that is normally displayed on the outside of the cell. For example, when such an exemplary engineered multi-pass membrane bound protein is translated in the ER, the positively charged N-terminal loop will be kept facing the cytosol, resulting a $N_{in}$-$C_{out}$ topology. Therefore, the endodomains of the engineered multi-pass protein can be displayed on the outside of the virions.

One embodiment involves the separation, identification and characterization of membrane bound proteins present in a biological sample. For example, by comparison of disease and control samples, it can be possible to identify "disease specific membrane bound proteins". These membrane bound proteins may be used as targets for drug development or as molecular markers of disease.

Antibody arrays can be used to monitor the expression levels of membrane bound proteins in a sample where such samples may include biopsy of a tissue of interest, cultured cells, microbial cell populations, biological fluids, including blood, plasma, lymph, synovial fluid, cerebrospinal fluid, cell lysates, culture supernatants, amniotic fluid, etc., and derivatives thereof. Of particular interest are clinical samples of biological fluids, including blood and derivatives thereof, cerebrospinal fluid, urine, saliva, lymph, synovial fluids, etc. Such measurements may be quantitative, semi-quantitative, or qualitative. Where the assay is to be quantitative or semi-quantitative, it will preferably comprise a competition-type format, for example between labeled and unlabeled samples, or between samples that are differentially labeled.

Assays to detect the presence of target molecules to the immobilized transmembrane polypeptides may be performed as follows, although the methods need not be limited to those set forth herein and include any suitable method known in the art.

Samples, fractions or aliquots thereof are added to a microarray comprising the antibodies. Samples may comprise a wide variety of biological fluids or extracts as described above. Preferably, a series of standards, containing known concentrations of control ligand(s) can be assayed in parallel with the samples or aliquots thereof to serve as controls. The incubation time should be sufficient for target molecules to bind the polypeptides. Generally, from about 0.1 to 3 hr, usually 1 hr, but could be as long as one day or longer.

After incubation, the insoluble support can be generally washed of non-bound components. Generally, a dilute non-ionic detergent medium at an appropriate pH, generally 7-8, can be used as a wash medium. From one to six washes may be employed, with sufficient volume to thoroughly wash non-specifically bound proteins present in the sample.

In order to detect the presence of bound target, a variety of methods may be used. These fall into three general groups. The target itself may be labeled with a detectable label, and the amount of bound label directly measured. Alternatively, the labeled sample may be mixed with a differentially labeled, or unlabeled sample in a competition assay. In yet another embodiment, the sample itself can be not labeled, but a second stage labeled reagent can be added in order to quantitate the amount of ligand present.

Examples of labels that permit direct measurement of ligand binding include radiolabels, such as $^3$H or $^{125}$I, fluorescers, dyes, beads, chemilumninescers, colloidal particles, and the like. Suitable fluorescent dyes are known in the art, including fluorescein isothiocyanate (FITC); rhodamine and rhodamine derivatives; Texas Red; phycoerythrin; allophycocyanin; 6-carboxyfluorescein (6-FAM); 2',7'-dimethoxy-4',5'-dichloro-6-carboxyfluorescein (JOE); 6-carboxy-X-rhodamine (ROX); 6-carboxy-2',4',7',4,7-hexachlorofluorescein (HEX); 5-carboxyfluorescein (5-FAM); N,N,N',N'-tetramethyl-6-carboxyrhodamine (TAMRA); sulfonated rhodamine; Cy3; Cy5; etc. Preferably the compound to be labeled can be combined with an activated dye that reacts with a group present on the ligand, e.g. amine groups, thiol groups, aldehyde groups, etc.

Where a second stage detection can be performed, for example by the addition of labeled transmembrane antibodies that recognize the transmembrane target, the label can be a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The second stage binding reagent may be any compound that binds the transmembrane target molecules with sufficient specificity such that it can be distinguished from other components present. In a preferred embodiment, second stage binding reagents are antibodies specific for the ligand, either monoclonal or polyclonal sera, e.g. mouse anti-human antibodies, etc.

For an amplification of signal, the ligand may be labeled with an agent such as biotin, digoxigenin, etc., where the second stage reagent will comprise avidin, streptavidin, anti-digoxigenin antibodies, etc. as appropriate for the label.

Microarrays can be scanned to detect binding of the ligands, e.g. by using a scanning laser microscope, by fluorimetry, a modified ELISA plate reader, etc. For example, a scanning laser microscope may perform a separate scan, using the appropriate excitation line, for each of the fluorophores used. The digital images generated from the scan are then combined for subsequent analysis. For any particular array element, the ratio of the fluorescent signal with one label can be compared to the fluorescent signal from the other label DNA, and the relative abundance determined.

The microarrays and methods of detecting target transmembrane molecules may be used for a number of screening, investigative and diagnostic assays. In one application, an array of transmembrane antibodies can be bound to total protein from an organism to monitor membrane bound protein expression for research or diagnostic purposes. Labeling total protein from a normal cell with one color fluorophore and total protein from a diseased cell with another color fluorophore and simultaneously binding the two samples to the same array allows for differential membrane bound protein expression to be measured as the ratio of the two fluorophore intensities. This two-color experiment can be used to monitor expression in different tissue types, disease states, response to drugs, or response to environmental factors.

In screening assays, for example to determine whether a membrane bound protein or membrane bound proteins are implicated in a disease pathway or are correlated with a disease-specific phenotype, measurements may be made from cultured cells. Such cells may be experimentally manipulated by the addition of pharmacologically active agents that act on a target or pathway of interest. This application can be important for elucidation of biological function or discovery of therapeutic targets.

For many diagnostic and investigative purposes it can be useful to measurement levels of target transmembrane molecules, e.g. membrane bound proteins, in blood or serum. This application can be important for the discovery and diagnosis of clinically useful transmembrane markers that correlate with a particular diagnosis or prognosis. For example, by monitoring a range of antibody or T cell receptor specificities in parallel, one may determine the levels and kinetics of transmembrane antibodies during the course of autoimmune disease, during infection, through graft rejection, etc. Alternatively, novel membrane bound protein markers associated with a disease of interest may be developed through comparisons of normal and diseased blood samples, or by comparing clinical samples at different stages of disease.

Information on the membrane bound protein expression in a genome of an organism can have a wide variety of applications, including but not limited to diagnosis and treatment of diseases in a personalized manner (also known as "personalized medicine") by association with phenotype such as onset, development of disease, disease resistance, disease susceptibility or drug response. Identification and characterization of the membrane bound proteins relevant to biological pathways in a genome of an organism in terms of cell- or tissue-specificity can also aid in the design of transgenic expression constructs for therapy with enhanced therapeutic efficacy and reduced side effects. Identification and characterization of membrane bound protein expression in terms of cell- or tissue-specificity can also aid in the development of function markers for diagnosis, prevention and treatment of diseases. "Disease" includes but is not limited to any condition, trait or characteristic of an organism that it can be desirable to change. For example, the condition may be physical, physiological or psychological and may be symptomatic or asymptomatic.

In another embodiment of the invention, the antibody arrays are used to detect post-translational modifications in membrane bound proteins, which can be important in studying signaling pathways and cellular regulation. Post-translational modifications can be detected using antibodies specific for a particular state of a protein, such as phosphorylated, glycosylated, farnesylated, etc.

The detection of these interactions between ligands and transmembrane polypeptides can lead to a medical diagnosis. For example, the identity of a pathogenic microorganism can be established unambiguously by binding a sample of the unknown pathogen to an array containing many types of transmembrane antibodies specific for known pathogenic transmembrane antigens.

Kits

In one embodiment, a kit comprising a library of transmembrane antibodies is provided. In one embodiment, a kit comprising a library of virions containing or expressing membrane bound proteins is provided. In some embodiments the library of transmembrane antibodies or virions can be arrayed in a support, e.g., 96 or 384 wells. In one embodiment, a kit comprises a microarray of transmembrane antibodies. In one embodiment, a kit comprises a microarray of virions containing or expressing membrane bound proteins. The kit may further include: reporter assay substrates; reagents for induction or repression of a particular biological pathway (cytokines or other purified proteins, small molecules, cDNAs, siRNAs, etc.), and/or data analysis software.

In addition, kits are provided which comprise reagents and instructions for performing methods of the present invention, or for performing tests or assays utilizing any of the compositions, libraries, arrays, or assemblies of articles of the present invention. The kits may further comprise buffers, enzymes, adaptors, labels, secondary antibodies and instructions necessary for use of the kits, optionally including troubleshooting information.

In yet another embodiment, the kit may comprise a library of transmembrane antibodies, such as described herein, and a library of virions containing or expressing membrane bound proteins, such as a proteome or membrane bound proteome of an organism. The kit may comprise at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's proteome. The kit may comprise at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of an organism's membrane bound proteome. The library of virions containing or expressing membrane bound proteins can represent a substantial portion or an entire organism's proteome, such as a bacterial, viral, fungal proteome. The library of virions containing or expressing membrane bound proteins can represent a substantial portion or an entire proteome or membrane bound proteome of an insect or mammal, such as a mouse, rat, rabbit, cat, dog, monkey, goat, or human. For example, an organism's proteome library can comprise at least about 11,000, 12,000, 13,000, 14,000, 15,000, 16,000, 17,000, 18,000, 19,000, or 20,000 different antigens. For example, an organism's proteome library can comprise at least about 100, 200, 300, 400, 500, 600, 700, 800, 900, 1,000, 2,000, 3,000, 4,000, 5,000, 5,500, or 5,600 membrane bound proteins.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-9119102); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

EXAMPLES

The following Examples have been included to provide guidance to one of ordinary skill in the art for practicing representative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

To develop a new, high-throughput platform that displays human membrane proteins in their native conformation, herpesvirus virions were utilized as a vehicle to fabricate a Virion Display microarray, dubbed VirD Array. Herpesviruses, for example herpes simplex virus type 1 (HSV-1), produce large membrane-enveloped virions that contain high copies of the viral glycoproteins, such as the three major glycoproteins gB, gC, and gD, that are distributed regularly in the circular virion structure. In addition, the DNA genome of this virus can be genetically manipulated to express foreign proteins in their native configuration or as fusions with the viral proteins. Two strategies were explored for the VirD array: 1) Clone a full-length human open reading frame (ORF) at the gB locus and express the gene under control of the strong gB promoter; 2) Fuse a human ORF to the transmembrane (TM) and cytoplasmic domains of gC and express this chimeric gene at the gC locus under the control of the gC promoter (FIG. 1a). Previous studies also utilized a gC chimera approach (hepatitis C virus glycoprotein E2) as well as expression from the gC locus (CD4) to incorporate foreign proteins in HSV-1 virions (Dolter et al. (1993) J. Virol. 67:189-95; Kouvatsis et al. (2007) Virus Res. 123:40-9). The absence of either gB or gC does not affect the ability of the virus to assemble mature enveloped virions in infected cells (Cai et al. (1987) J. Virol. 61:714-21; Holland et al. (1984) J. Virol. 52:566-74; Homa et al. (1986) J. Virol. 58:281-9). To test the feasibility of the two approaches, CD4 was chosen as a classical type I membrane protein with a single TM domain and GPR77 as a representative of the multi-spanning, G-protein coupled receptor membrane protein. CD4 is a well-characterized membrane glycoprotein of T lymphocytes that interacts with major histocompatibility complex class II antigens and is also a receptor for the human immunodeficiency virus (Carr et al. (1989) J. Biol. Chem. 264:21286-95). GPR77 is involved in the complement system of the innate immune response with a canonical ligand identified (i.e., complement component C5a) (Cain & Monk (2002) J. Biol. Chem. 277:7165-9). Both strategies were employed to express and display these two human membrane proteins in HSV-1 virions. One goal was to examine the expression and incorporation of these human membrane proteins into HSV-1 virions and to determine whether these human membrane proteins are maintained in their native form in purified virions immobilized on a glass surface at high density.

Recombinant methods were used to generate four viruses (see Supplemental Materials and Methods below for details). The recombinant viruses, gB:CD4 and gB:GPR77, express the full-length human membrane proteins at the gB locus under the control of native gB promoter. A V5 epitope tag was also incorporated at the C-termini of both proteins for biochemical detection purposes. Viruses labeled as CD4-gC and GPR77-gC, express human membrane proteins fused to the gC C-terminal domain (i.e., 497 to 511 aa), which contains the TM and a short cytosolic domain required for anchoring to the virus tegument. Like the human genes cloned at the gB locus, the gC chimeras were cloned at the gC locus under the control of native gC promoter.

To examine whether CD4 and GPR77 were expressed and correctly processed through the secretory pathway, human fibroblasts infected with the recombinant and parental viruses were stained for cell surface localization with antibodies against the ectodomains of CD4, GPR77, and HSV-1 gD (FIG. 1b). gD was detected on the surfaces of infected cells (FIG. 1b; insets). CD4 expressed either from the gB promoter or as a gC-chimeric protein showed a similar strong signal on the cell surface. GPR77 was detected on the cell surface, but had a different distribution dependent on whether it was expressed from the gB promoter or as a gC-chimera. These results show that CD4 and GPR77, like gD, expressed off the HSV-1 genome were delivered to the surface of the plasma membrane via the canonical secretory pathway. CD4 and GPR77 also display the expected intracellular distribution as judged by staining with V5 antibody (FIG. 1b; right panel). The intracellular distribution of CD4 was similar when stained with anti-CD4 or anti-V5 antibodies (FIG. 3).

Further biochemical evidence for the expression of at least the V5-tagged human proteins was obtained using immunoblot analysis of total infected cell lysates (FIG. 1c; left panel). Virion incorporation of these human membrane proteins was also examined. Wild type and gB null (K082) virions (Cai et al. (1987) J. Virol. 61:714-21), as well as gB:CD4, gB:GPR77 virions, were purified and subjected to the same immunoblot analysis with anti-V5 antibodies. Both gB:CD4 and gB:GPR77 virions showed strong anti-V5 reactivity at the expected molecular weights of CD4 and GPR77, while no detectable signals were observed in the other virions (FIG. 1c; right panel). Anti-gD antibodies were used as a loading control. Together, these data confirmed that both CD4 and GPR77 were synthesized and incorporated into virions produced in infected human cells.

To demonstrate that human proteins could be displayed in the correct orientation after virion incorporation, flow cytometry analysis of purified virions stained with PE-labeled antibodies that recognize the ectodomain of CD4 was performed (FIG. 1d). An HSV-1 recombinant virus that incorporates the Venus fluorescent protein in the capsid was used to identify and gate purified virions (see Supplemental Materials and Methods below). K082 virions were used as a negative control for antibody binding specificity. Judging from the amounts of PE fluorescence detected within the gated virion populations, 85.5% of gB:CD4 virions were labeled with PE antibody and slightly more, 96.1% of CD4-gC virions were bound to PE antibody. These results were consistent with data from different virion preparations using similar experimental conditions. This observation was further confirmed using a standard ELISA analysis using chemiluminescent substrates for detection (FIG. 4). All virion preparations were stained with anti-gD antibodies as expected. Virions expressing CD4 or GPR77 were stained with the respective antibodies. There was little or no reactivity of the CD4 and GPR77 antibodies with the KOS or K082 virions. The signal observed with anti-gD antibodies was significantly higher because of the higher affinity of this monoclonal antibody for its antigen. Taken together, these results demonstrated that human membrane proteins were incorporated in the correct orientation that could be recognized by antibodies that recognize the extracellular domains of these proteins, showing that they were embedded in the virion envelope in their native conformation.

To test whether these recombinant virions could be immobilized in a microarray format at high density, while maintaining their functional integrity, the recombinant virions were spotted on different glass surfaces at various titers. Using anti-gD antibodies, it was determined that nitrocellulose-coated slides (i.e., FAST) provided the optimal detection as low as 50,000 virions (KOS plaque forming units) per spot and the anti-gD signals started to reach saturation after the titer was increased to >400,000 virions (FIG. 5). Therefore, it was decided that the VirD Array would be constructed with seven different virus preparations at a titer of 800,000 virions (KOS plaque forming units) per spot in a 4×4 format.

To visualize and examine the integrity of immobilized virions on glass, these arrays were stained with anti-gD ectodomain and anti-VP5 antibodies, the latter of which recognizes the major capsid protein, VP5. All seven virions showed strong anti-gD signals but much lower anti-VP5 signals, indicating that the vast majority of the immobilized virions were intact (FIG. 2a; left panel). This conclusion was further supported by the observation that the anti-gD signals were greatly reduced on the VirD Arrays after the virion envelopes were stripped with a mild detergent treatment using NP40 (FIG. 2a; right panel). In contrast, strong anti-VP5 signals were seen in all seven virions following this treatment. Moreover, staining the VirD Arrays with anti-gB and -gC antibodies confirmed the absence of gB and gC proteins in gB:CD4/GPR77 and CD4/GPR77-gC, respectively (FIG. 6).

Because glycosylation is important for human membrane protein activity, fluorescently labeled lectins were employed (i.e., SNA-II, PHA-L, CA, and WGA) to profile glycan structures on the VirD Arrays (Tao et al. (2008) *Glycobiology* 18:761-9; Kung et al. (2009) *Mol. Syst. Biol.* 5:308). Comparison of the lectin staining patterns between wild type, gB-KO (K082) and gC-KO (gCΔ39) (Homa et al. (1986) *J. Virol.* 58:281-9) virions showed that gC is more heavily glycosylated than gB, because all four lectins showed much weaker binding signals to gC-KO virions (FIG. 2b). A more careful analysis of lectin CA staining patterns, which recognizes Galβ(1-4)GlcNAc, GalNAcβ(1-4)GlcNAc, or NeuAcα(2-6)Galβ(1-4)GlcNAc, revealed that CD4 was very likely glycosylated. This is because CD4-gC (i.e., gC-) virions showed significantly higher signals than both gC-KO and GPR77-gC (i.e., gC-) virions. This observation is further supported by the same SNA-II (recognizing terminal Galβ, GalNAcβ, or NeuAcα(2-6)Galβ(1-4)GlcNAc) staining pattern because it is known that SNA-II should recognize the same glycan structures or partial glycan structures as CA does based on the database of lectin specificity at the Consortium for Functional Glycomics (CFG) Gateway (ISSN:1752-184X) (FIG. 2b). Interestingly, a very similar glycan structure NeuAcα(2-3)Galβ(1-4)GlcNAc was previously identified on mouse CD4 expressed in CHO cells using a mass spectrometry approach, indirectly supporting the present observation (Carr et al. (1989) *J. Biol. Chem.* 264:21286-95). Therefore, human CD4 is very likely to be glycosylated with NeuAcα(2-6)Galβ(1-4)GlcNAc. However, specific glycan structures associated with GPR77 could not definitively be determined, probably due to a limited number of lectins used in this study. Regardless, the above results suggest that virion-displayed human membrane proteins showed expected glycosylation.

To determine whether human CD4 and GPR77 proteins displayed on the surface of virions immobilized on a glass surface were in the correct orientation, the VirD Arrays were stained with antibodies that each recognize the ectodomains of CD4 or GPR77 (FIGS. 2c and 2d). Strong and specific staining signals were observed in the gB:CD4 and CD4-gC, gB:GPR77 and GPR77-gC virions, respectively, indicating that these proteins were in the correct orientation and both membrane protein display strategies worked.

Finally, to demonstrate that virion-displayed human membrane proteins were in active conformation, the VirD Arrays were probed with a fluorescently labeled canonical ligand, complement anaphylatoxin C5a, of GPR77 (see Supplemental Materials and Methods below for more details). As shown in the right panel in FIG. 2d, Cy5-labled C5a showed strong binding activity to the GPR77-gC virions on the array, albeit weaker binding signals to the gB:GPR77 virions. No detectable signals were observed in other virions, suggesting the interaction between C5a and GPR77 on the VirD Array was highly specific. Taken together, these results demonstrated that GPR77 was displayed correctly on the virions and maintained its functional conformation on the VirD Array.

Display of soluble peptides or protein in various formats has been effective using different carrier systems (Li (2000) *Nat. Biotechnol.* 18:1251-6). In this study, fabrication of a VirD Array that displays human membrane proteins on the envelopes of engineered HSV-1 virions immobilized at high density on solid glass surfaces was demonstrated. Using antibodies and lectins it was shown that two human membrane proteins, CD4 and GPR77, were in the right orientation and potentially glycosylated. It was further demonstrated that virion-displayed GPR77 was in its active conformation via a binding assay with its cognate ligand C5a. The VirD Array approach has advantages that include, but are not limited to: 1) Displayed human membrane proteins are embedded in human cell membranes, a more physiologically relevant environment that can help maintain their native conformation; 2) As demonstrated with GPR77, membrane proteins with multiple TM domains are likely to be folded correctly in the virion envelopes; 3) Since the virus exploits the human secretory pathways, the displayed human proteins are likely to maintain their canonical posttranslational modifications (PTMs) as they are transported through the secretory pathways; this was demonstrated via lectin binding assays; and 4) The VirD Array is expected to be readily transformed to a high-content platform that can display virtually all of the human membrane proteins close to their native conformation on a single glass slide. Once such a high-throughput platform is established, it will allow for performance of high-throughput screens for novel drug target identification against membrane proteins, to identify ligands of various types of receptors, and to profile PTM of membrane proteins.

Supplemental Materials and Methods

Cells and Viruses. Vero cells, transformed Vero cell lines and human foreskin fibroblasts (HFT) were grown in minimum essential medium—alpha medium supplemented with 10% fetal calf serum (Gibco-Invitrogen) and passaged as described by Desai et al. (Desai et al. (1998) *Virology* 247:115-24). HFT is an immortalized cell line that is transduced with a retrovirus expressing human telomerase (Hahn et al. (1999) *Nature* 400:464-8). D6 (UL27 transformed) was used as the host cell for growth of the recombinant viruses that expressed genes from the gB locus (Cai et al. (1987) *J. Virol.* 61:714-21). The A1.1 (UL27 and UL28 transformed) cell line (Tengelsen et al. (1993) *J. Virol.* 67:3470-80) was used for the marker-rescue/marker-transfer method to introduce the human genes cloned into the gB loci (Desai et al. (1994) *Virology* 204:312-22) and was a kind gift from Fred Homa of the University of Pittsburgh. Stocks of the parental wild-type virus strain KOS (HSV-1) and the mutant and recombinant viruses were prepared as previously described (Desai et al. (1998) *Virology* 247:115-24).

Antibodies. Antibodies reactive to human CD4 and GPR77 were purchased from Santa Cruz Biotechnology and Sigma-Aldrich. PE-conjugated anti-CD4 antibody used for flow cytometry analysis was obtained from BD Biosciences. The V5 monoclonal antibody was purchased from Invitrogen Life Technologies. Anti-HSV-1 gB antibody clone B6 and anti-gC antibodies were a kind gift from Joseph Glorioso (University of Pittsburgh). Anti-HSV-1 gD antibody DL6 was a generous gift from David Johnson (OHSC) and Gary Cohen and Roz Eisenberg (Penn University). The VP5 antibody LP12 was kindly provided by Tony Minson (University of Cambridge, UK).

Plasmids. Plasmid pKΔ4B was derived by Cai et al. (Cai et al. (1988) *J. Mol. Biol.* 201:575-88) following engineering of linker-insertion mutants in the glycoprotein B gene. DNA sequences encoding amino acids 43 through 711 of gB were deleted and a BglII restriction site added to maintain the protein reading frame. (Cai et al. (1988) *J. Mol. Biol.* 201:575-88). pKΔ4B was digested with Xho1 and BglII, treated with antartic phosphatase (NEB) and ligated with an Xho1-BglII PCR fragment amplified from pKΔ4B which deletes all gB amino acids from 1-43 (gBΔSS) but retains the gB promoter sequences (Table 1). This plasmid was designated pKgBΔSS. The sequence of gB amino acids spanning 711 to 796 were deleted from pKgBΔSS by cassette PCR mutagenesis. The PCR fragment was cloned as a BglII-BamH1 into pKgBΔSS and the resulting plasmid was labeled pKgBPR. The human CD4 and GPR77 sequences were amplified from the plasmids from the Ultimate ORF collection (Life Technologies). The sequence encoding the V5 epitope was included in the reverse primer (Table 1). The final gB promoter driven gene plasmids were labeled pKgB:CD4 and pKgB:GPCR77. Sequence analysis of the different plasmids was done prior to introduction into the virus genome. Plasmids were linearized with BamH1 for homologous recombination.

TABLE 1

Primer Sequences.

| Primer | Sequence (5'-3') |
|---|---|
| UL28-XhoI-F | CTTTGCCTCGGTCTACCGGTGCGGGG (SEQ ID NO: 1) |
| gBΔSS-BglII-R | GGGAGATCTGAGGCGGGACTACGGGGCCCGTCG (SEQ ID NO: 2) |
| gB-797-BglII-F | GGGAGATCTGGGTGGAGGTGGAGGTTACGTCATGCGGCTG CAGAGCAAC (SEQ ID NO: 3) |
| gB-nc-BamHI-R | GGGATCCCAACCGGAGGCATCCAAC (SEQ ID NO: 4) |
| gB-CD4-BglII-F | GGCAGATCTACCATGAACCGGGGAGTCCCTTTTAGG (SEQ ID NO: 5) |
| gB-CD4V5-BglII-R | CCCAGATCTCTACGTAGAATCTAGACCGAGGAGAGGGTTA GGGATAGGCTTACCAATGGGCTACATGTCTTCTGAAA (SEQ ID NO: 6) |
| gB-GPR77-BglII-F | GGCAGATCTACCATGGGGAACGATTCTGTCAGCTAC (SEQ ID NO: 7) |
| gB-GPR77V5-BglII-R | CCCAGATCTCTACGTAGAATCTAGACCGAGGAGAGGGTTA GGGATAGGCTTACCAATGGGCTACATGTCTTCTGAAA (SEQ ID NO: 8) |
| gC-KAN-F | GGGGGGACCAAACTATATAGATATTAAAAAGGTAACGGGGG GGTCTTGCGTTACCGCCGATGACGCTGCCGCGA (SEQ ID NO: 9) |
| gC-KAN-R | GGGGGGACCAAACTATATAGATATTAAAAAGGTAACGGGGG GTCTTGCGTTACCGCCGATGACGCTGCCGCGA (SEQ ID NO: 10) |
| CD4-F | GGAATTCAACATGAACCGGGGAGTCCCTTTTAGG (SEQ ID NO: 11) |
| CD4-R-Overlap | CCCGATTCCAATTGGCTGCACCGGGGTGGACCATGT (SEQ ID NO: 12) |

TABLE 1-continued

Primer Sequences.

| Primer | Sequence (5'-3') |
|---|---|
| gC-F-Overlap | CCGGTGCAGCCAATTGGAATCGGGGTTCTCGCGGCG (SEQ ID NO: 13) |
| gC-R | GGGGATCCTTACCGCCGATGACGCTGCCGCGA (SEQ ID NO: 14) |
| GPR77-F | GGAATTCACCATGGGGAACGATTCTGTCAGCTAC (SEQ ID NO: 15) |
| GPR77-R-Overlap | CCCGATTCCAATGGGTTCAGCCCGCAGGGCCCTGGC (SEQ ID NO: 16) |
| gC-F-Overlap | CGGGCTGAACCCATTGGAATCGGGGTTCTCGCGGCG (SEQ ID NO: 17) |
| gC-RedET (CD4)-F | CGCTTTGCCGGGAACGCTAGCCGATCCCTCGCGAGGGGA GGCGTCGGGCACCATGAACCGGGGAGTCCCTTTTAGG (SEQ ID NO: 18) |
| gC-RedET (GPR77)-F | CGCTTTGCCGGGAACGCTAGCCGATCCCTCGCGAGGGGA GGCGTCGGGCACCATGGGGAACGATTCTGTCAGCTAC (SEQ ID NO: 19) |
| gC-RedET-R | GGGGGGACCAAACTATATAGATATTAAAAAGGTAACGGGGG GTCTTGCGTTACCGCCGATGACGCTGCCGCGA (SEQ ID NO: 20) |

Marker-rescue/marker-transfer assays. The marker rescue of UL28 and marker transfer of the gB:human ORF gene was accomplished using the method described in Desai et al. (Desai et al. (1994) *Virology* 204:312-22). A1.1 cell monolayers (1×10$^6$) in 60 mm petri dishes were co-transfected with 25 μl of infected cell DNA (KΔ4BX) and 0.1-0.05 μg linearized plasmid DNA using the calcium phosphate precipitation method. When plaques began to appear (72 h after transfection) the cell monolayers were harvested, freeze/thawed once, sonicated and total virus progeny titered. The recombinant virus was isolated by single plaque purification on D6 cells. Additional plaque purification was carried out by limiting dilution on the D6 cell line.

Red-ET recombination. The KOS BAC37 genome (Gierasch et al. (2006) *J. Virol. Methods* 135:197-206) was transferred into TOP10 cells (Stratagene) for this method. KOS BAC37 was kindly provided by David Leib, Dartmouth University, NH. The procedure to engineer gC chimera fusions into the virus genome used the Gene Bridges Red-ET method and the protocols provided (Zhang et al. (2000) *Nat. Biotechnol.* 18:1314-7). The kanamycin cassette surrounded by gC homologous sequences was amplified using gC-Kan-F and gC-Kan-R primers and pRPSL-neo as a template. This kanamycin gene was introduced into KOS BAC37 replacing the gC gene. Colonies that grew on kanamycin plates were screened for streptomycin sensitivity before the next step. The CD4-gC and GPR77-gC fusion genes were made using Overlap PCR methods using the primers listed in Table 1. The CD4-gC and GPR77-gC chimera fusions were amplified using the RedET primers listed in Table 1 and were used to replace the kanamycin gene. Successful isolates carrying the correct chimeric genes were identified by PCR assays and the inserted gene in the BAC genome was sequenced prior to reconstitution of infectious virus.

Transfection of Bacmid DNA to re-constitute infectious virus. The KOS Bacmids carrying the glycoprotein C chimera gene fusions were prepared using the PureLink nucleic acid purification kit (Life Technologies). The Bacmid DNA was transfected into Vero cells (5×10⁵) in 12 well trays using Lipofectamine 2000 reagent (Life Technologies). Plaques generally began to appear after 3 days and this infected cell lysate was used to amplify and prepare working stocks of each of the gC chimera viruses.

Western blot analysis. Infected cell extracts were resolved by SDS-PAGE in MES buffer and transferred to iBlot membranes (Life Technologies) using an iBlot apparatus (Life Technologies) according to the manufacturer's protocol. The transferred membranes were blocked with blocking buffer (TBS with 5% non-fat milk) at room temperature for an hour with gentle shaking, and then incubated with primary antibodies (1:5000 dilution in blocking buffer) at room temperature for an hour with gentle shaking. The membranes were washed for 5 min with TBS+0.1% Tween20 (TBST) buffer for 3 times with shaking. HRP-conjugated anti-mouse antibodies (GE Healthcare) were incubated on the membranes at 5,000-fold dilution in blocking buffer for an hour with gentle shaking. The membranes were washed for 5 min with TBST buffer for 3 times with shaking and incubated with ECL Plus Western Blotting detection reagents (GE Healthcare) for 5 min before signals were visualized by ImageQuant LAS 4000 imaging system (GE Healthcare).

Immunofluorescence and Confocal Analysis. HFT cells in LabTek (#1 borosilicate glass) four well chamber slides (6×10⁵ cells) were infected at a multiplicity of infection (MOI) of 10 plaque forming units (PFU) per cell. Infected cells were washed 2× with DPBS (Dulbecco's phosphate buffered saline), fixed with 4% paraformaldehyde in DPBS for 25 min; washed 2× with DPBS and permeabilized with 0.25% triton X-100 in DPBS for 30 min. After permeabilization, the cells were washed 2× with 3% BSA in DPBS and non-specific reactivity was blocked for 30 min in the same buffer. For cell surface labeling the detergent permeabilization step was omitted and the cells incubated with blocking buffer. Primary antibody was diluted in 3% BSA/DPBS and 250 µl added to each chamber well for 60 min (room temperature). Subsequently the cells were washed 3× with 3% BSA/DPBS and then incubated with Cy3-labeled secondary antibody (Jackson Laboratories) for 45 min (room temperature). The cells were then washed 3× with 3% BSA/DPBS and then incubated in Fluormount G (EMS) prior to imaging. The stained infected cells were analyzed in a Zeiss LSM 510 confocal microscope. Most images were collected with a pinhole set at 1 Airy units.

Virion preparation. Extracellular virions were prepared from HFT cells. Generally 8.6×10⁶ cells in 100 mm petri dishes were infected at an MOI of 10 PFU/cell. The culture medium was harvested at 72 h post-infection, clarified by centrifugation at 3500 rpm for 30 min at 4° C. The supernatant was layered on a 20% sucrose cushion (W/V in growth medium) and centrifuged in a Beckman SW41 (39 K for 30 min) or SW32 (24 K for 60 min). The virion pellet was resuspended in PBS at 4° C. overnight and then used for subsequent analyzes. For VirD Array printing the virion preparations were resuspended in PBS plus 35% glycerol.

Flow-Cytometry. Extracellular virions (150 µl volumes) were incubated with PE-conjugated flow antibodies (20 µl) and incubated at room temperature (tube rocker) for one hour in the dark. The virions (volume adjusted to 500 µl with PBS) were then sedimented through 20% sucrose cushion (250 µl) in an eppendorf tube at 16000 g for 60 min. The supernatant was discarded and the virus pellet resuspended in 200 µl PBS. The labeled virions were analyzed in a BD FACSARIA II instrument using the DIVA software (version 6.1.3).

Enzyme-linked immunosorbent assay (ELISA). Serial dilutions of virions were incubated in Nunc MaxiSorp flat-bottom 96 well white plates. The sealed plates were incubated at 4° C. for 2 days. The wells were washed with PBS+0.02% Tween-20 (PBS+T20) 3× for 5 min each time on a platform shaker and then blocked with 2% BSA in PBS+T20 for 60 min at room temperature. Primary antibody dilutions were made in blocking buffer generally 1:2000 to 1:250 and incubated for 60 min. Secondary HRP conjugated mouse antibody was used at a 1:1000 concentration. The plates were washed 3× with PBS+T20 for 5 min each wash after both primary and secondary antibody binding. The reaction was quantitated using SuperSignal ELISA Pico (Pierce) chemiluminescent substrate according to the manufacturer's procedure and the plate read in a Glomax luminometer to determine relative light units (425 nm).

VirD Array fabrication. Purified virions were arrayed in a 384-well plate and spotted on FAST slides (Whatman) in a 4×4 pattern along with BSA as a negative control. The printed arrays were stored at −80° C.

Antibody assays on VirD Arrays. VirD Arrays were blocked with blocking buffer (TBS with 3% BSA) at room temperature for an hour with gentle shaking, then incubated with primary antibodies (1:1000 dilution in blocking buffer) at room temperature for an hour with gentle shaking. The arrays were washed for 5 min with TBS+0.1% Tween20 (TBST) buffer for 3 times with shaking. To visualize the presence of human or viral proteins, Cy5-labeled anti-mouse antibodies (The Jackson Laboratory) were incubated on the arrays at 1,000-fold dilution in blocking buffer. The arrays were washed for 5 min with TBST buffer for 3 times with shaking, briefly rinsed with water, and dried by spinning. The slides were finally scanned with a GenePix 4000B scanner (MDS Analytical Technologies).

Ligand binding assay on VirD Array. The VirD Array was blocked in TBST with 1% BSA for 1 h at room temperature with gentle shaking. C5a (Abcam) was labeled with Cy5 NHS Easter (GE Healthcare) and incubated on the VirD Array at 1 µM in ligand binding buffer (1 mM MgCl₂, 2 mM CaCl₂, 0.2% BSA, and 25 mM HEPES, pH 7.4) at room temperature for 1 h with gentle shaking. The array was washed for 5 mM in ice-cold washing buffer (0.5 M NaCl in 10 mM HEPES, pH 7.4) for 3 times with shaking, dried by spinning, and scanned as described above.

Lectin binding assays on VirD Arrays. VirD Arrays were blocked in PBS with 1% BSA for 1 h with gentle shaking. Lectins (EY Laboratories) were labeled with Cy5 NHS Easter (GE Healthcare) and incubated on the VirD Array at 1 µg/ml in PBS with 0.5 mM CaCl₂ and 1% BSA at room temperature for 1 h with gentle shaking. The array was washed for 5 min in PBST for 3 times with shaking, dried by spinning, and scanned as described above.

Example 2

Subcloning Human ORFs Encoding Membrane Bound Proteins into an Expression Vectors.

For highly efficient subcloning of libraries of human ORFs encoding membrane bound proteins into a wide variety of destination vectors, all in frame, without the use of restriction enzymes, GATEWAY™ technology is utilized based on phage lambda integration proteins (FIG. 20). A collection representing human ORFs encoding membrane bound proteins is cloned in the Gateway™ Entry vector, which allows for convenient subcloning the inserts into various Gateway™. Destination vectors are used for expression and functional analysis of the target protein in a variety of hosts, including virions, *E. coli* (FIG. 24), yeast, baculovirus, CHO cells, and mammalian cell lines, as well as cell-free transcription and translation coupling systems. After attaining the library a human membrane bound protein expression library is subcloned into virions, enabling construction of a near-complete human membrane bound proteome microarray (Hu-MBPM).

Subsequently, all human ORFs encoding membrane bound proteins (about 5,600) are subcloned and a success rate is confirmed by restriction digestion. All starting clones used to generate the virions or expression vectors from which the proteins are expressed have their ORFs completely sequenced. Spot sequencing of 200 randomly selected virion clones show 100% correct assignment to wells i.e., providing very high confidence in collection quality. The 5' junctions of that entire collection are sequenced as a validation step. Three replicates of the collection are prepared, from one of which the entry plasmid DNAs are extracted, and the quality of this plasmid DNA is determined on agarose gels. The resulting recombinants are then transformed into bacteria and single colonies are selected on Amp-containing LB-agar plates. For each recombination, four single colonies are picked to generate glycerol stocks, two of which are further processed to extract plasmid DNAs in a 96-well format. The extracted plasmid DNAs are digested with a restriction enzyme to release the inserts, and run on agarose gels to examine the vector and insert sizes as an indicator of successful subcloning. Each restriction digest is scored based on expected insert sizes and the success rate is determined. Validation is performed on over 200 randomly selected LR clones by sequencing. The confirmed LR constructs are rearrayed to generate a master set of expression clones for virions. Similar large scale cloning is completed in a bacterial expression vector. This experiment is repeated with a human expression vector, complete with 5' junction sequencing of the entire human membrane bound protein expression library.

---

We claim:

1. An array comprising:
   (a) a substrate; and
   (b) a plurality of recombinant herpesviridae virion microspots associated with a surface of the substrate, wherein the recombinant herpesviridae virion microspots comprise a plurality of recombinant herpesviridae virions, wherein the recombinant herpesviridae virions comprise envelopes comprising a plurality of human heterologous membrane bound proteins that retain their native conformations, interactions, or both, and wherein the human heterologous membrane bound proteins are encoded by the genomes of the recombinant herpesviridae virions.

2. The array of claim 1, wherein the recombinant herpesviridae virions comprise recombinant Herpes simplex virus (HSV) virions.

3. The array of claim 2, wherein the recombinant HSV virions comprise Herpes simplex virus 1 (HSV-1) virions.

4. The array of claim 1, wherein the plurality of human heterologous membrane bound proteins comprises a classical type I membrane protein with a single transmembrane domain.

5. The array of claim 4, wherein the classical type I membrane protein with a single transmembrane domain comprises CD4.

6. The array of claim 1, wherein the human heterologous membrane bound proteins comprise a multi-spanning G-protein coupled receptor (GPCR) membrane protein.

7. The array of claim 6, wherein the multi-spanning GPCR membrane protein comprises GPR77.

8. The array of claim 1, wherein the plurality of human heterologous membrane bound proteins comprises a protein selected from the group consisting of an ion channel, a receptor tyrosine kinase, a receptor serine/threonine kinase, a receptor guanylate cyclase, a growth factor receptor, a hormone receptor, and combinations thereof.

9. The array of claim 1, wherein a density of the plurality of recombinant herpesviridae virion microspots associated with the surface of the substrate ranges from 1/cm$^2$ to 50/cm$^2$.

10. A method for producing an array comprising a substrate, the method comprising:
    (a) contacting a solution comprising recombinant herpesviridae virions to a surface of the substrate, wherein the recombinant herpesviridae virions comprise envelopes comprising a plurality of human heterologous membrane bound proteins, wherein the plurality of human heterologous membrane bound proteins retain their native conformations, interactions, or both, and wherein the human heterologous membrane bound proteins are encoded by the genomes of the recombinant herpesviridae virions; and
    (b) repeating the contacting to provide a recombinant herpesviridae virion microspots pattern on the surface of the substrate.

11. The method of claim 10, wherein the recombinant herpesviridae virions comprise recombinant Herpes simplex virus (HSV) virions.

12. The method of claim 11, wherein the recombinant HSV virions comprise Herpes simplex virus 1 (HSV-1) virions.

13. The method of claim 10, wherein the human heterologous membrane bound proteins comprise a classical type I membrane protein with a single transmembrane domain.

14. The method of claim 13, wherein the classical type I membrane protein with a single transmembrane domain comprises CD4.

15. The method of claim 10, wherein the human heterologous membrane bound proteins comprise a multi-spanning G-protein coupled receptor (GPCR) membrane protein.

16. The method of claim 15, wherein the multi-spanning GPCR mebrane protein comprises GPR77.

17. The method of claim 10, wherein at least one or each of the human heterologous membrane bound proteins is selected from the group consisting of an ion channel, a receptor tyrosine kinase, a receptor serine/threonine kinase, a receptor guanylate cyclase, a growth factor receptor, a hormone receptor, and combinations thereof.

18. A method for detecting a binding event between a human heterologous membrane bound protein and a target, the method comprising:
   (a) contacting a sample with the array of claim 1, wherein the sample comprises a solution comprising the target; and
   (b) detecting a binding event between the human heterologous membrane bound protein and the target.

19. The method of claim 18, wherein the target is labeled and the detecting comprises detecting the presence of the label.

20. The method of claim 19, wherein the detecting is by optical detection methods comprising absorption in the visible or infrared range, chemoluminescence, fluorescence, optical waveguides, surface plasmon resonance, surface charge sensors, surface force sensors, or combinations thereof.

21. A method of identifying a ligand as a target for a membrane bound protein, the method comprising:
   (a) contacting the array of claim 1 with a ligand;
   (b) determining binding between a human heterologous membrane bound protein and the ligand; and
   (c) identifying the ligand as a target for the membrane bound protein when the human heterologous membrane bound protein binds to the ligand.

22. The method of claim 21, wherein the ligand is selected from the group consisting of peptides, lipids, fatty acids, carbohydrates, small molecules, and combinations thereof.

23. The method of claim 21, wherein the ligand comprises a label.

24. The method of claim 23, wherein the label is selected from the group consisting of fluorescent dyes and radioisotopes.

25. The method of claim 23, wherein the label is a fluorescent dye selected from the group consisting of Fluo8, DiBAC4, and ANG-2.

* * * * *

SEQUENCE LISTING

```
<160> NUMBER OF SEQ ID NOS: 20

<210> SEQ ID NO 1
<211> LENGTH: 26
<212> TYPE: DNA
<213> ORGANISM: Artificial Sequence
<220> FEATURE:
<223> OTHER INFORMATION: UL28-Xho1-F primer

<400> SEQUENCE: 1
ctttgcctcg gtctaccggt gcgggg                                         26

<210> SEQ ID NO 2
<211> LENGTH: 34
<212> TYPE: DNA
<213> ORGANISM: Artificial Sequence
<220> FEATURE:
<223> OTHER INFORMATION: gB(triangle)SS-Bg111-R primer

<400> SEQUENCE: 2
gggagatctg aggcgggact acgggggccc gtcg                                34

<210> SEQ ID NO 3
<211> LENGTH: 49
<212> TYPE: DNA
<213> ORGANISM: Artificial Sequence
<220> FEATURE:
<223> OTHER INFORMATION: gB-797-Bg111-F primer

<400> SEQUENCE: 3
gggagatctg ggtggaggtg gaggttacgt catgcggctg cagagcaac                49

<210> SEQ ID NO 4
<211> LENGTH: 25
<212> TYPE: DNA
<213> ORGANISM: Artificial Sequence
<220> FEATURE:
<223> OTHER INFORMATION: gB-nc-BamH1-R primer

<400> SEQUENCE: 4
gggatcccaa ccggaggcat ccaac                                          25

<210> SEQ ID NO 5
<211> LENGTH: 36
<212> TYPE: DNA
<213> ORGANISM: Artificial Sequence
```

```
<220> FEATURE:
<223> OTHER INFORMATION: gB-CD4-BglII-F primer

<400> SEQUENCE: 5
ggcagatcta ccatgaaccg gggagtccct tttagg                              36

<210> SEQ ID NO 6
<211> LENGTH: 78
<212> TYPE: DNA
<213> ORGANISM: Artificial Sequence
<220> FEATURE:
<223> OTHER INFORMATION: gB-CD4V5-BglII-R primer

<400> SEQUENCE: 6
cccagatctc tacgtagaat ctagaccgag gagagggtta gggataggct taccaatggg   60
gctacatgtc ttctgaaa                                                 78

<210> SEQ ID NO 7
<211> LENGTH: 36
<212> TYPE: DNA
<213> ORGANISM: Artificial Sequence
<220> FEATURE:
<223> OTHER INFORMATION: gB-GPR77-BglII-F primer

<400> SEQUENCE: 7
ggcagatcta ccatggggaa cgattctgtc agctac                              36

<210> SEQ ID NO 8
<211> LENGTH: 78
<212> TYPE: DNA
<213> ORGANISM: Artificial Sequence
<220> FEATURE:
<223> OTHER INFORMATION: gB-GPR77V5-BglII-R primer

<400> SEQUENCE: 8
cccagatctc tacgtagaat ctagaccgag gagagggtta gggataggct taccaatggg   60
gctacatgtc ttctgaaa                                                 78

<210> SEQ ID NO 9
<211> LENGTH: 74
<212> TYPE: DNA
<213> ORGANISM: Artificial Sequence
<220> FEATURE:
<223> OTHER INFORMATION: gC-KAN-F primer

<400> SEQUENCE: 9 gggggggacca aactatatag atattaaaaa ggtaacgggg gggtcttgcg ttaccgccga   60
tgacgctgcc gcga                                                     74

<210> SEQ ID NO 10
<211> LENGTH: 74
<212> TYPE: DNA
<213> ORGANISM: Artificial Sequence
<220> FEATURE:
<223> OTHER INFORMATION: gC-KAN-R primer

<400> SEQUENCE: 10 gggggggacca aactatatag atattaaaaa ggtaacgggg gggtcttgcg ttaccgccga   60
tgacgctgcc gcga                                                     74

<210> SEQ ID NO 11
<211> LENGTH: 34
<212> TYPE: DNA
```

<213> ORGANISM: Artificial Sequence
<220> FEATURE:
<223> OTHER INFORMATION: CD4-F primer

<400> SEQUENCE: 11
ggaattcaac atgaaccggg gagtcccttt tagg        34

<210> SEQ ID NO 12
<211> LENGTH: 36
<212> TYPE: DNA
<213> ORGANISM: Artificial Sequence
<220> FEATURE:
<223> OTHER INFORMATION: CD4-R-Overlap primer

<400> SEQUENCE: 12
cccgattcca attggctgca ccggggtgga ccatgt      36

<210> SEQ ID NO 13
<211> LENGTH: 36
<212> TYPE: DNA
<213> ORGANISM: Artificial Sequence
<220> FEATURE:
<223> OTHER INFORMATION: gC-F-Overlap

<400> SEQUENCE: 13
ccggtgcagc caattggaat cggggttctc gcggcg      36

<210> SEQ ID NO 14
<211> LENGTH: 32
<212> TYPE: DNA
<213> ORGANISM: Artificial Sequence
<220> FEATURE:
<223> OTHER INFORMATION: gC-R primer

<400> SEQUENCE: 14
ggggatcctt accgccgatg acgctgccgc ga          32

<210> SEQ ID NO 15
<211> LENGTH: 34
<212> TYPE: DNA
<213> ORGANISM: Artificial Sequence
<220> FEATURE:
<223> OTHER INFORMATION: GPR77-F primer

<400> SEQUENCE: 15
ggaattcacc atggggaacg attctgtcag ctac        34

<210> SEQ ID NO 16
<211> LENGTH: 36
<212> TYPE: DNA
<213> ORGANISM: Artificial Sequence
<220> FEATURE:
<223> OTHER INFORMATION: GPR77-R-Overlap primer

<400> SEQUENCE: 16
cccgattcca atgggttcag cccgcagggc cctggc      36

<210> SEQ ID NO 17
<211> LENGTH: 36
<212> TYPE: DNA
<213> ORGANISM: Artificial Sequence
<220> FEATURE:
<223> OTHER INFORMATION: gC-F-Overlap primer

<400> SEQUENCE: 17
cgggctgaac ccattggaat cggggttctc gcggcg      36

```
<210> SEQ ID NO 18
<211> LENGTH: 77
<212> TYPE: DNA
<213> ORGANISM: Artificial Sequence
<220> FEATURE:
<223> OTHER INFORMATION: gC-RedET(CD4)-F primer

<400> SEQUENCE: 18
cgctttgccg ggaacgctag ccgatccctc gcgaggggga ggcgtcgggc accatgaacc      60
ggggagtccc ttttagg                                                    77

<210> SEQ ID NO 19
<211> LENGTH: 77
<212> TYPE: DNA
<213> ORGANISM: Artificial Sequence
<220> FEATURE:
<223> OTHER INFORMATION: gC-RedET(GPR77)-F primer

<400> SEQUENCE: 19
cgctttgccg ggaacgctag ccgatccctc gcgaggggga ggcgtcgggc accatgggga      60
acgattctgt cagctac                                                    77

<210> SEQ ID NO 20
<211> LENGTH: 74
<212> TYPE: DNA
<213> ORGANISM: Artificial Sequence
<220> FEATURE:
<223> OTHER INFORMATION: gC-RedET-R primer

<400> SEQUENCE: 20 gggggggacca aactatatag atattaaaaa ggtaacgggg gggtcttgcg ttaccgccga      60
tgacgctgcc gcga                                                       74
```